(12) United States Patent
Zhou et al.

(10) Patent No.: US 10,253,007 B2
(45) Date of Patent: Apr. 9, 2019

(54) TAXANES COMPOUNDS, PREPARATION METHOD THEREFOR, AND USES THEREOF

(71) Applicant: Jiangsu Tasly Diyi Pharmaceutical Co., Ltd., Huai'an, Jiangsu (CN)

(72) Inventors: Wei Zhou, Tianjin (CN); Yunrong Jing, Tianjin (CN); Yongfeng Wang, Tianjin (CN); Guocheng Wang, Tianjin (CN)

(73) Assignee: Jiangsu Tasly Diyi Pharmaceutical Co., Ltd., Huai'an, Jiangsu (CN)

( * ) Notice: Subject to any disclaimer, the term of this patent is extended or adjusted under 35 U.S.C. 154(b) by 0 days.

(21) Appl. No.: 15/038,264

(22) PCT Filed: Nov. 21, 2014

(86) PCT No.: PCT/CN2014/091908
§ 371 (c)(1),
(2) Date: May 20, 2016

(87) PCT Pub. No.: WO2015/074605
PCT Pub. Date: May 28, 2015

(65) Prior Publication Data
US 2016/0297784 A1    Oct. 13, 2016

(30) Foreign Application Priority Data

Nov. 22, 2013    (CN) .......................... 2013 1 0595107

(51) Int. Cl.
*A61K 31/337* (2006.01)
*C07D 305/14* (2006.01)
(Continued)

(52) U.S. Cl.
CPC .......... *C07D 305/14* (2013.01); *C07C 233/87* (2013.01); *C07C 271/22* (2013.01); *C07D 405/12* (2013.01)

(58) Field of Classification Search
None
See application file for complete search history.

(56) References Cited

U.S. PATENT DOCUMENTS

| 5,614,549 | A | 3/1997 | Greenwald et al. |
| 5,646,176 | A | 7/1997 | Golik et al. |

(Continued)

FOREIGN PATENT DOCUMENTS

| CN | 1087905 A | 6/1994 |
| CN | 1094041 A | 10/1994 |

(Continued)

OTHER PUBLICATIONS

STN Registry File. Registry # 114915-14-9, entered Jun. 18, 1988.*
(Continued)

*Primary Examiner* — Deepak R Rao
*Assistant Examiner* — Laura M Daniel
(74) *Attorney, Agent, or Firm* — Glenn J. Foulds; Bret E. Field; Bozicevic, Field & Francis LLP

(57) ABSTRACT

The present invention provides taxanes compounds with a formula (I) or formula (II) structure, a method for preparing the compounds, as well as the use of the compositions containing the compounds, pharmaceutically acceptable salts and solvates thereof as active ingredients in manufacturing oral antitumor medicaments,

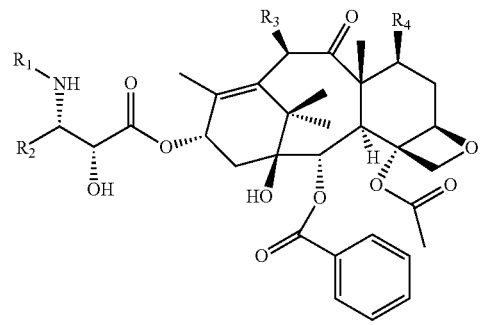

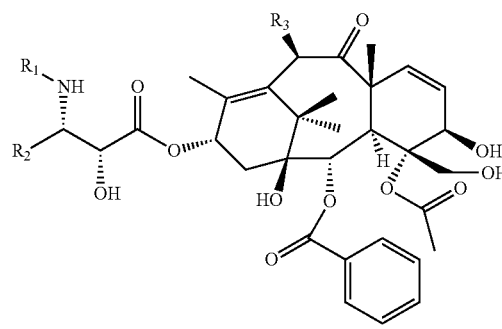

In formula (I), $R_1$ is —$COR_6$, —$COOR_6$ or —$CONR_{7a}R_{7b}$; $R_2$ is a C1-C6 alkyl, a C1-C6 alkenyl, a substituted hydrocarbon group, a heterocyclic group, an aromatic group or a substituted aromatic group; $R_3$ is —$OR_6$, —$OCOOR_6$, —$OCOSR_6$ or —$OCONR_{7a}R_{7b}$; $R_4$ is —$OR_6$, —$OCOOR_6$, —$OCOSR_6$, —$OCONR_{7a}R_{7b}$ or H; wherein, $R_6$ is a C1-C6 alkyl, a C1-C6 alkenyl, a C1-C6 alkynyl, a substituted hydrocarbon group, an aromatic group or a heterocyclic group; $R_{7a}$ and $R_{7b}$ are respectively hydrogen, a hydrocarbon group, a substituted hydrocarbon group or a heterocyclic group. In formula (II), $R_1$ is —$COR_6$ or —$COOR_6$; $R_2$ is an aromatic group; $R_3$ is —$OR_6$; wherein, $R_6$ is a C1-C6 alkyl, a C1-C6 alkenyl, a C1-C6 alkynyl, a substituted hydrocarbon group, an aromatic group or a heterocyclic group.

14 Claims, 34 Drawing Sheets

(51) Int. Cl.
*C07D 405/12* (2006.01)
*C07C 271/22* (2006.01)
*C07C 233/87* (2006.01)

(56) References Cited

U.S. PATENT DOCUMENTS

| | | |
|---|---|---|
| 5,721,268 A | 2/1998 | Holton et al. |
| 5,821,363 A * | 10/1998 | Wicnienski ......... C07D 305/14 548/215 |
| 6,005,138 A | 12/1999 | Holton et al. |
| 6,040,466 A | 3/2000 | Bouchard et al. |
| 6,160,135 A | 12/2000 | Bouchard et al. |
| 2002/0038038 A1 | 3/2002 | Bouchard et al. |
| 2013/0211109 A1 | 8/2013 | Lahiri et al. |

FOREIGN PATENT DOCUMENTS

| | | | |
|---|---|---|---|
| CN | 1179776 A | 4/1998 | |
| CN | 1210525 A | 3/1999 | |
| CN | 1709864 A | 12/2005 | |
| EP | 0558959 A1 | 9/1993 | |
| JP | H7-149779 A | 6/1995 | |
| JP | H10-509461 A | 9/1998 | |
| WO | WO-9302065 A1 * | 2/1993 | ........... C07D 305/14 |
| WO | WO9302065 A1 | 2/1993 | |
| WO | WO9623779 A1 | 8/1996 | |
| WO | WO2010059916 A2 | 5/2010 | |
| WO | WO2013080217 A2 | 6/2013 | |

OTHER PUBLICATIONS

STN Registry File. Registry No. 1099376-27-8 entered Feb. 2, 2009.*
Heo, Jae. Bull. Korean Chem. Soc. (2009) vol. 30, No. 1.*
Jing et al., The synthesis of novel taxoids for oral administration, Bioorg Med Chem. Jan. 1, 2014;22(1):194-203.

* cited by examiner

TAXANES COMPOUNDS, PREPARATION METHOD THEREFOR, AND USES THEREOF

FIELD OF THE INVENTION

The present invention belongs to the field of pharmaceutical chemistry, and specifically relates to a novel compound, in particular to taxanes compounds. The present invention also relates to the preparation method of the taxanes compounds and uses thereof as active ingredients in manufacturing oral antitumor medicaments.

BACKGROUND OF THE INVENTION

Paclitaxel (PTX) has a structure represented by the following formula:

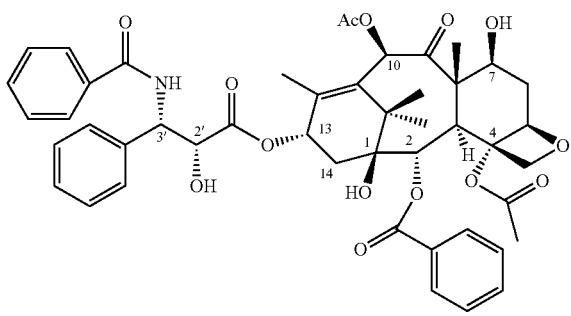

Paclitaxel was extracted from the bark of *Taxus* genus *Taxus brevifolia* in 1971, which is an active antitumor compound with a unique anticancer mechanism and has definite therapeutic effect on a variety of cancers. Currently in clinical practice, paclitaxel is usually administered by intravenous injection. However, due to its poor water solubility, paclitaxel is usually dissolved in a mixed solvent of polyoxyethylated castor oil (Chremophor EL) and ethanol (1:1, v/v), to prepare paclitaxel injections, which is sold under the trade name "Taxol" or "Paxene".

Although a great success has been achieved in clinical application, paclitaxel is also restricted by many factors in the meantime: (1) firstly, paclitaxel itself has toxic and side effects, including dose-limiting toxicity and bone marrow suppression (clinically, it is necessary be used in combination with a growth factor for treatment), on normal tissues and cells, and cannot cross the blood-brain barrier, etc; (2) with the use of Chremophor EL, the ensuing problem is serious allergic reactions, primary hyperlipidemia, central nervous system (CNS) toxicity and pharmacokinetics change of paclitaxel [ten Tije A J, et al, Clin Pharmacokinet 42, 655-685, 2003; H. Gelderblom, et al, Eur. J. Cancer 37 (13), 1590-1598, 2001, van Zuylen L, et al, Invest New Drugs 19, 125-141, 2001; R. B. Weiss, et al, J. Clin. Oncol. 8 (7). 1263-1268, 1990]; (3) multiple drug resistance happens due to long-term medication.

In order to solve the aforesaid problems, many scholars at home and abroad have carried out in-depth studies on the structure-activity relationships of paclitaxel, including changing pharmaceutical dosage form, developing a prodrug of paclitaxel, synthesizing taxane derivatives, medication in combination with P-gp inhibitor, and the like. New ways are continuously explored to improve its water solubility, enhance therapeutic effect as well as reduce toxic and side effects.

It has enormous practical significance to carry out studies on the oral taxanes derivatives, since changing the nature of taxanes compounds themselves can fundamentally solve the problems thereof such as poor water-solubility, high toxicity and the like, so as to improve the oral bioavailability, reduce toxic and side effects and enhance therapeutic effect thereof. Furthermore, it will be able to avoid adverse reactions brought by co-solvents, and help prolong therapeutic effect and enhance tolerance of patients by converting injection administration to oral administration.

The researchers found that in the structural modification of paclitaxel molecule, the variation of substituents at C7, C9 and C10 positions have little effect on activity thereof, but these positions are binding sites with P-gp protein. The affinity of paclitaxel molecule with P-gp protein is affected by the size, electrical, hydrogen bond forming ability of the substituents on the positions. Thus, modification on these groups could overcome the multiple drug resistance caused by P-gp over-expression and solve the problem of low oral bioavailability and the like.

In view of this, the inventors were engaged in research of paclitaxel derivatives, and eventually found out a series of novel compounds with improved oral bioavailability. As shown in pharmacological experiments, compared with the prior art, these taxanes derivatives synthesized in the present invention have strong cytotoxicity to a variety of human cancer cell lines and broad-spectrum anti-tumor effects. It can be seen from the in vitro activity data on MCF-7 breast cancer cell line that the cytotoxicity is maintained, while some derivatives even have better cytotoxicity than that of paclitaxel. The in vivo absorption and transport of taxanes derivatives is predicted by using the human-derived colorectal adenocarcinoma cell line Caco-2 cell monolayer model. It can be seen from the experimental results that, compared with the prior art, most of these derivatives have enhanced membrane-permeate absorption capacity and reduced efflux effects, such that they are predicted to have improved oral bioavailability. Therefore, the cytotoxicity of these taxanes derivatives are maintained (or even enhanced), furthermore, their oral bioavailability are also enormously improved.

CONTENT OF THE INVENTION

The present invention provides taxanes compounds having the structure represented by the following general formula I:

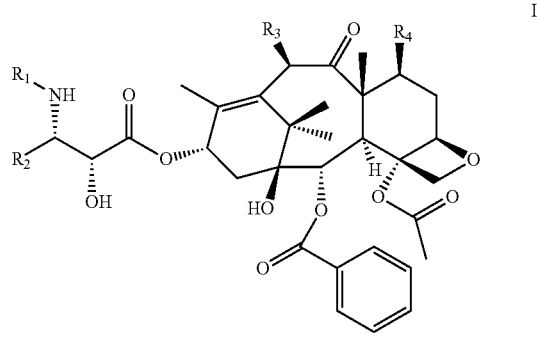

wherein, $R_1$ is —$COR_6$, —$COOR_6$, or —$CONR_{7a}R_{7b}$;

$R_2$ is a C1-C6 alkyl, a C1-C6 alkenyl group, a substituted hydrocarbon group, a heterocyclic group, an aromatic group or a substituted aromatic group;

$R_3$ is $-OR_6$, $-OCOOR_6$, $-OCOSR_6$, or $-OCONR_{7a}R_{7b}$;

$R_4$ is $-OR_6$, $-OCOOR_6$, $-OCOSR_6$, $-OCONR_{7a}R_{7b}$, or H;

wherein, R is a C1-C6 alkyl, a C1-C6 alkenyl, a C1-C6 alkynyl group, a substituted hydrocarbon group, an aromatic group or a heterocyclic group; $R_{7a}$ and $R_{7b}$ are respectively hydrogen, a hydrocarbon group, a substituted hydrocarbon group or a heterocyclic group.

Further, the present invention also provides taxanes compounds having the structure represented by the following general formula II:

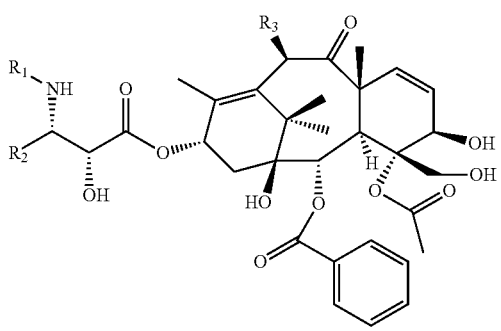

wherein, $R_1$ is $-COR_6$, or $-COOR_6$:

$R_2$ is an aromatic group:

$R_3$ is $-OR_6$;

wherein $R_6$ is a C1-C6 alkyl, a C1-C6 alkenyl, a C1-C6 alkynyl group, a substituted hydrocarbon group, an aromatic group or a heterocyclic group.

The present invention further provides a preparation method of taxanes compounds of the present invention.

Said preparation method of taxanes compounds of the present invention comprises the following steps:

Step 1 synthesis of a precursor of five-member ring oxazolidine acid side chain: the precursor of five-member ring oxazolidine acid side chain is prepared by a series of reactions including introduction of protective groups, addition condensation, acid hydrolysis, aldol condensation, catalytic hydrogenation and the like:

Step 2 synthesis of taxanes mother nucleus part: by using 10-deacetyl baccatin III (10-DAB) as raw material, the hydroxyl groups at C7 and C10 positions of the mother nucleus part are selectively modified on the basis of different activities thereof, to give taxanes mother nucleus part;

Step 3 synthesis of taxanes derivatives: the precursor of five-member ring oxazolidine acid side chain is linked with the taxanes mother nucleus part by esterification, and a series of taxanes derivatives are generated after removal of protective group by acid hydrolysis.

Furthermore, the present invention provides a pharmaceutical composition comprising the compounds of the above defined general formula (I) and general formula (II), pharmaceutically acceptable salts or solvates thereof as active ingredients, as well as the use of the same in manufacturing oral antitumor medicaments.

The present invention has the following advantages:

A series of taxanes derivatives were synthesized by simultaneously changing substituents at multiple positions of C7, C10, C3'N and C3' of paclitaxel. In the in vitro cytotoxicity assay on a variety of cancer cell lines, they showed good antitumor activities. The in vitro oral bioavailability of such taxanes derivatives was predicted by using Caco-2 cell monolayer trans-membrane transport assay, showing from the experimental results that the membrane permeability of all such derivatives were higher than that of paclitaxel and the degree of the improvement was significant. By analyzing the result of efflux ratio in the bidirectional transport assay, it was shown that such derivatives could inhibit the efflux effect of P-gp in different degrees, and further verified that the oral absorption capacity of these compounds was improved. In addition, the compound PCMI-31, which showed the highest membrane permeability in the in vitro assay, was selected to carry out in vivo oral bioavailability with rats. It was shown from the experimental results that its absolute oral bioavailability was increased to 10.7%, indicating that the in vivo oral absorption capability thereof was improved in a certain degree by compared with that of paclitaxel. Accordingly, the taxanes derivatives of the present invention with such structures were potential oral antitumor medicaments.

DETAILED DESCRIPTION OF THE INVENTION

Figure 1:
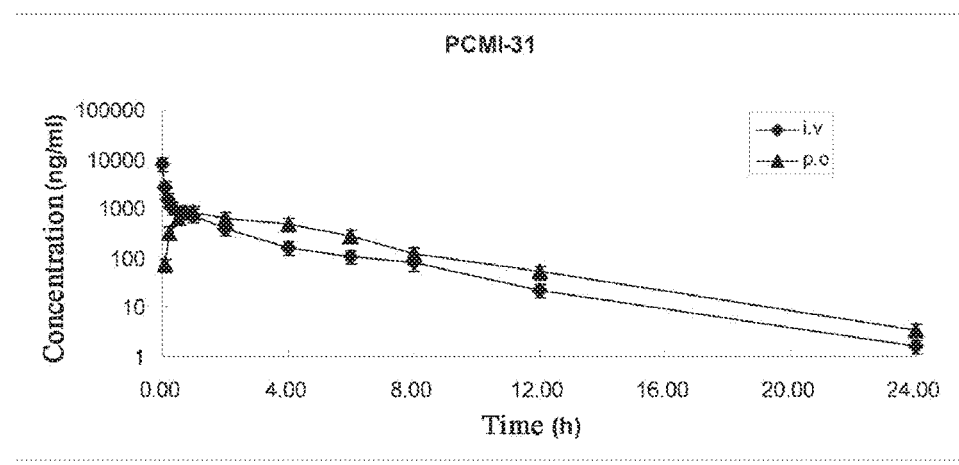
FIG. 1 is the plasma concentration-time curve of PCMI-31.
Figure 2:
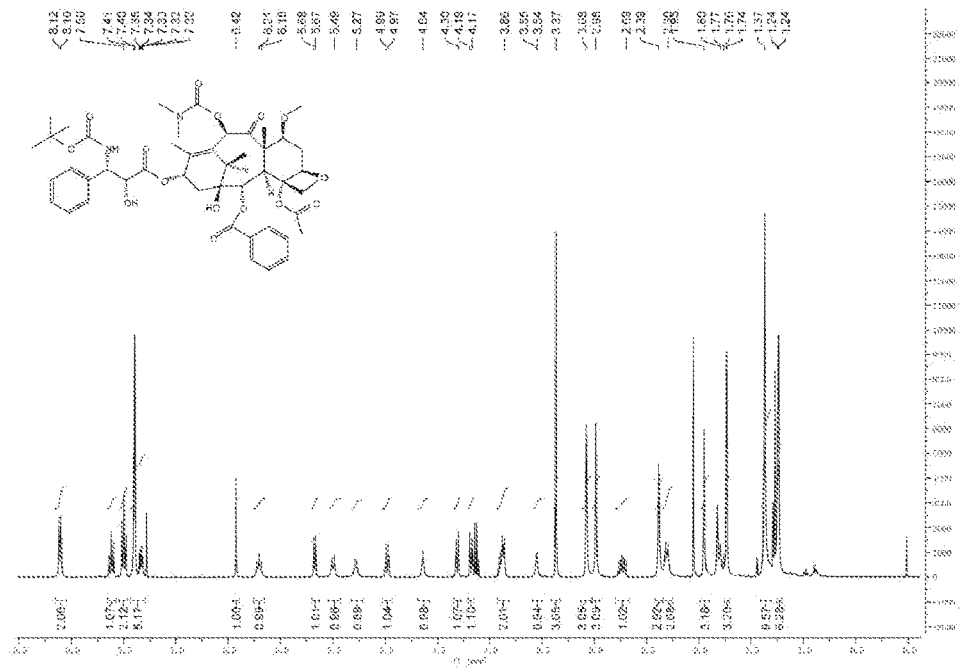
FIG. 2 is the $^1$H NMR spectrum of PCMI-22.
Figure 3:
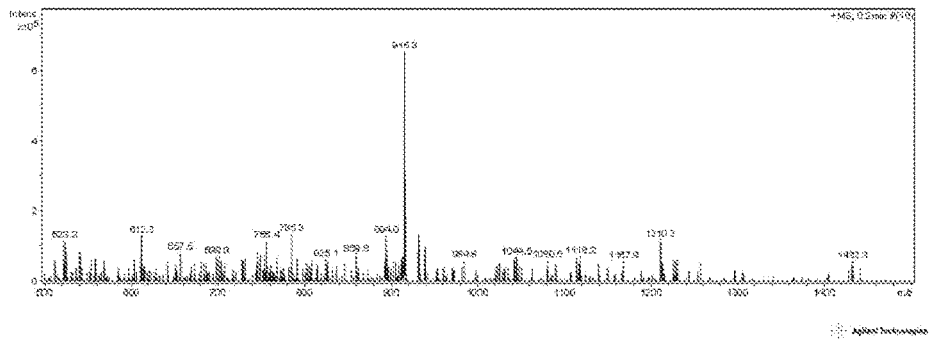
FIG. 3 is the MS spectrum of PCMI-22.
Figure 4:
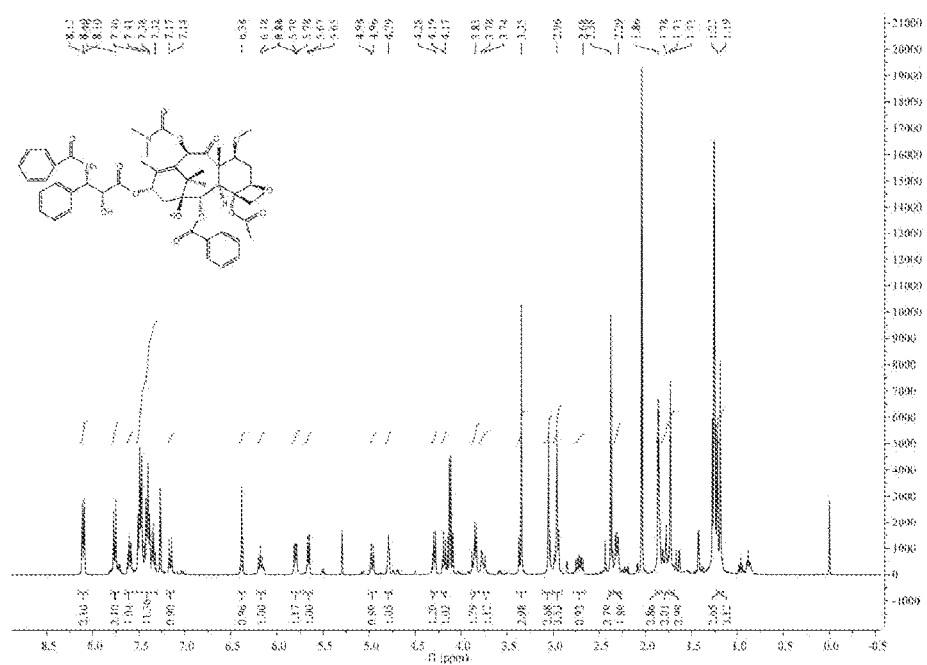
FIG. 4 is the $^1$H NMR spectrum of PCMI-23.
Figure 5:
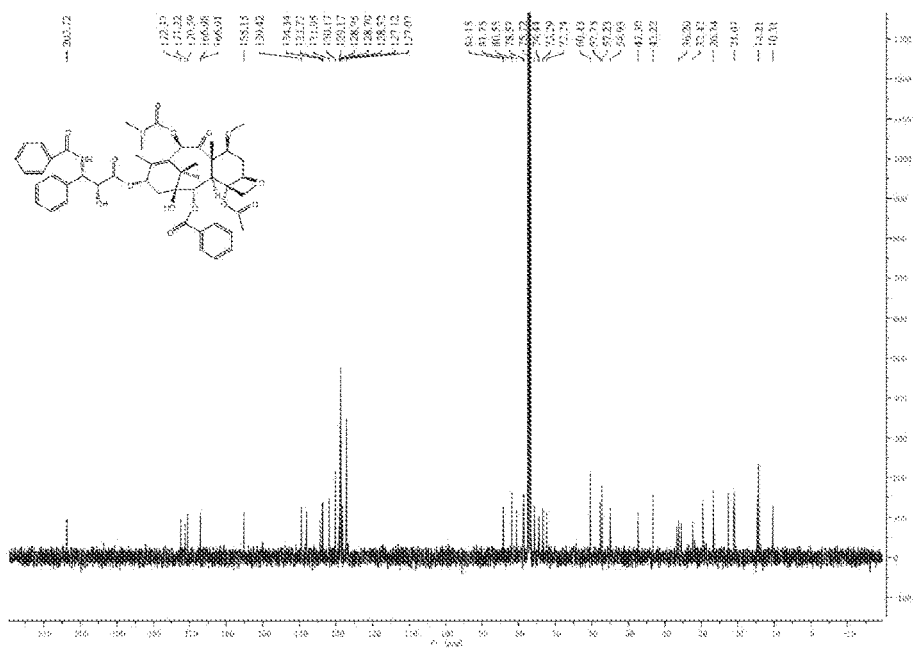
FIG. 5 is the $^{13}$C NMR spectrum of PCMI-23.
Figure 6:
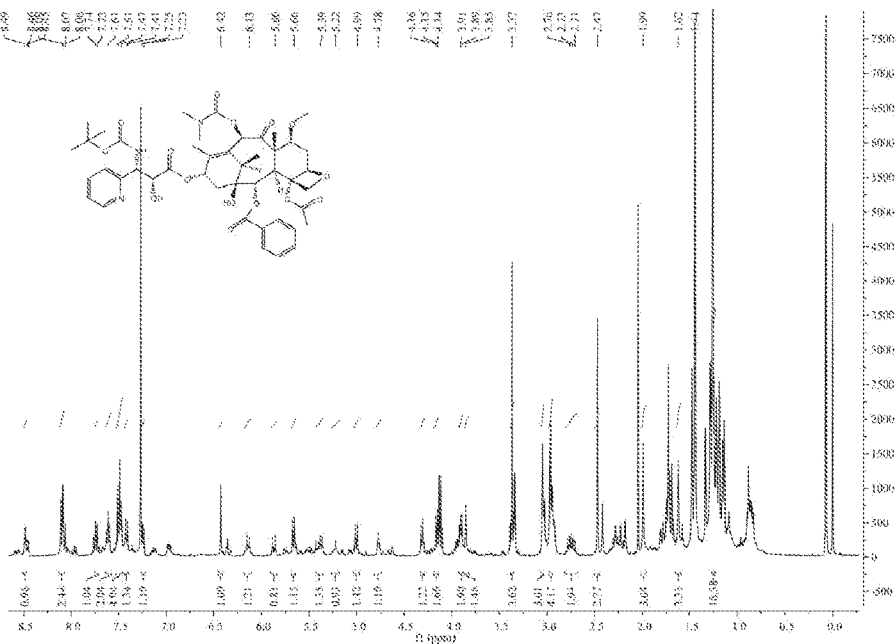
FIG. 6 is the $^1$H NMR spectrum of PCMI-24.
Figure 7:
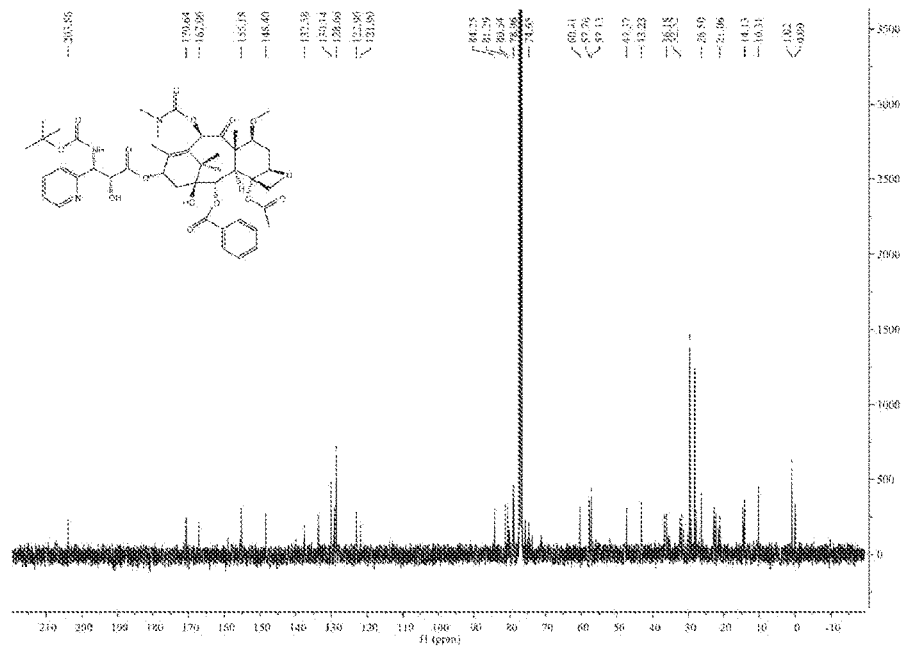
FIG. 7 is the $^{13}$C NMR spectrum of PCMI-24.
Figure 8:
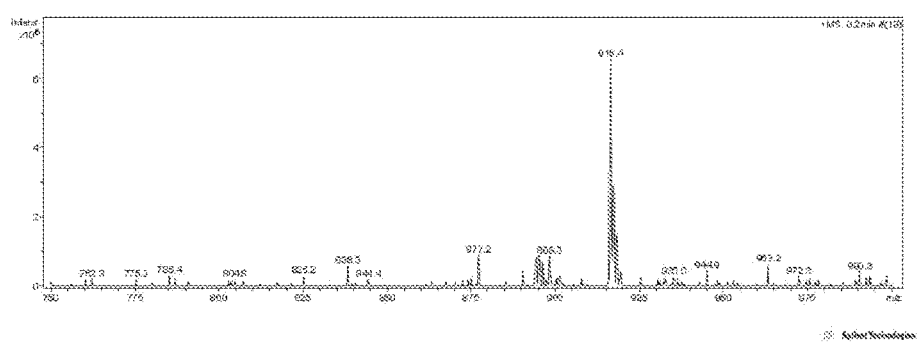
FIG. 8 is the MS spectrum of PCMI-24.
Figure 9:
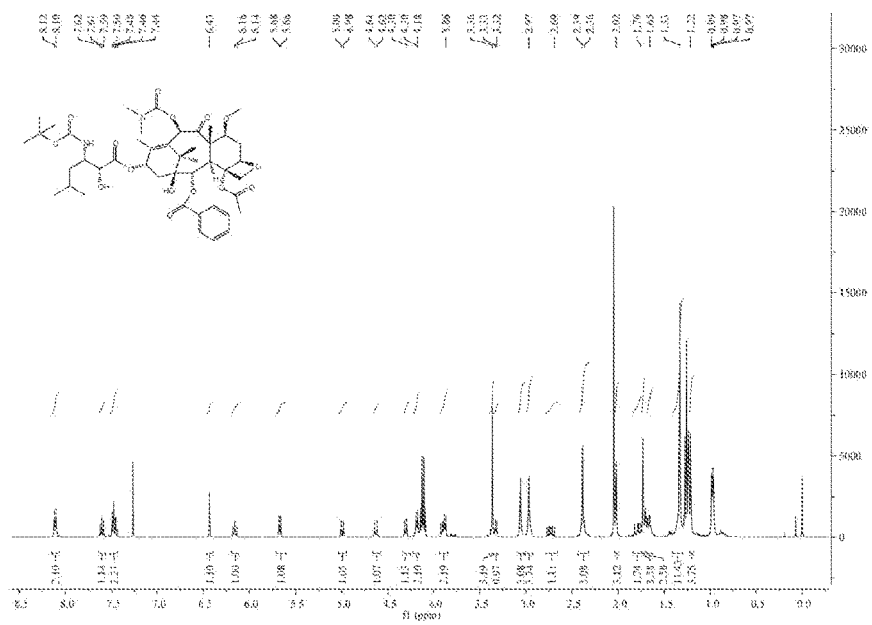
FIG. 9 is the $^1$H NMR spectrum of PCMI-25.
Figure 10:
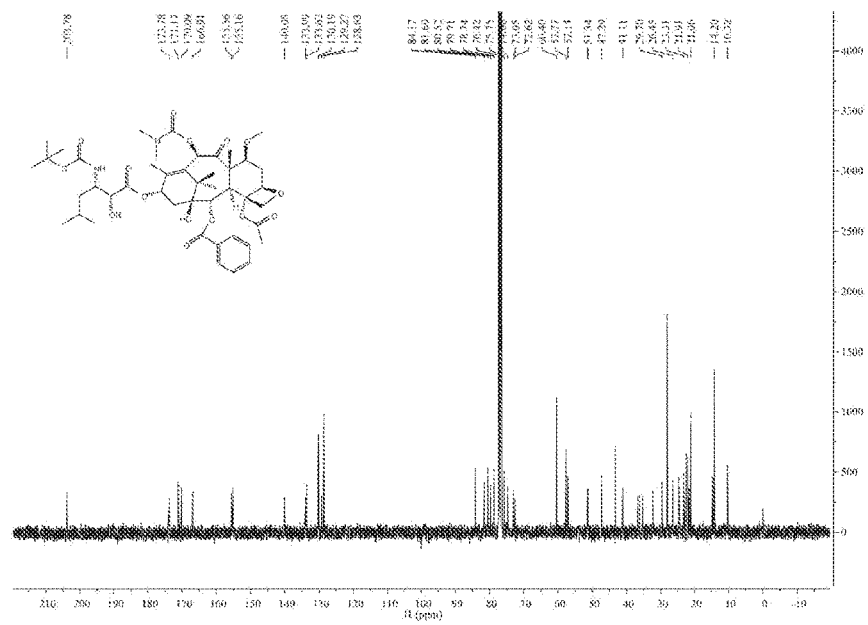
FIG. 10 is the $^{13}$C NMR spectrum of PCMI-25.
Figure 11:
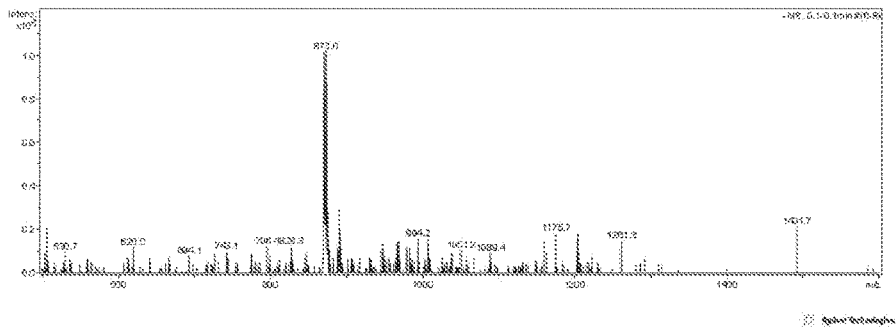
FIG. 11 is the MS spectrum of PCMI-25.
Figure 12:
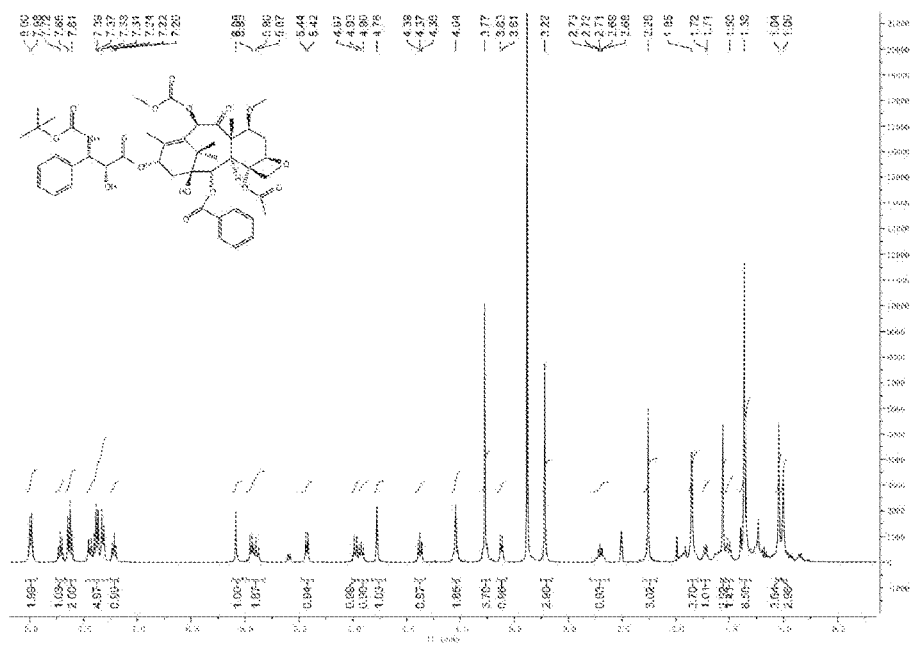
FIG. 12 is the $^1$H NMR spectrum of PCMI-26.
Figure 13:
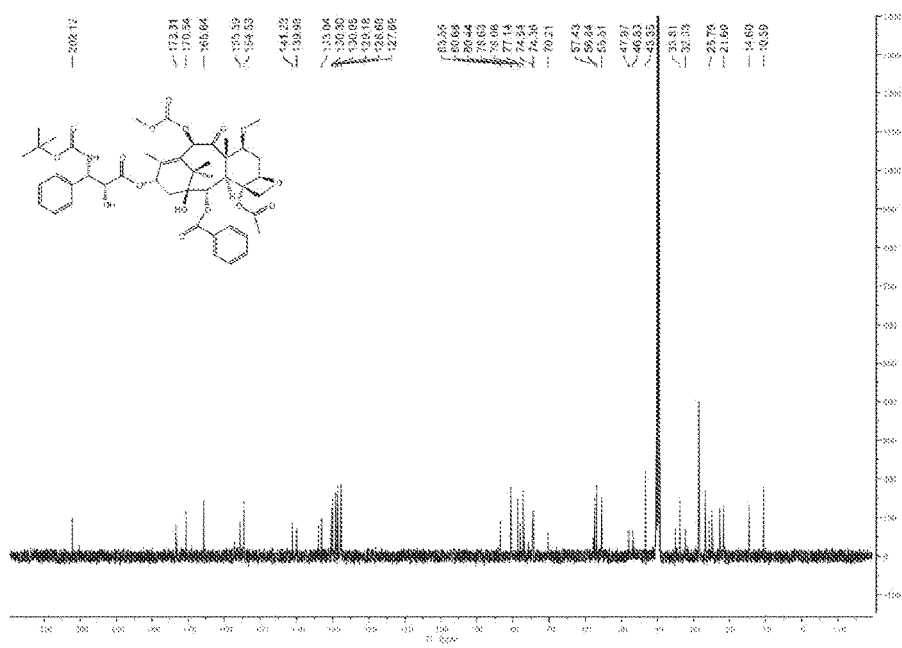
FIG. 13 is the $^{13}$C NMR spectrum of PCMI-26.
Figure 14:
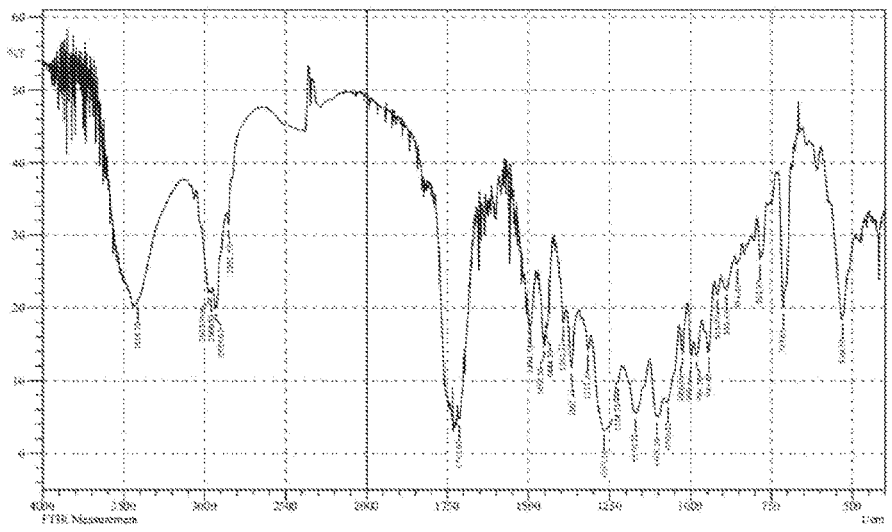
FIG. 14 is the IR spectrum of PCMI-26.
Figure 15:
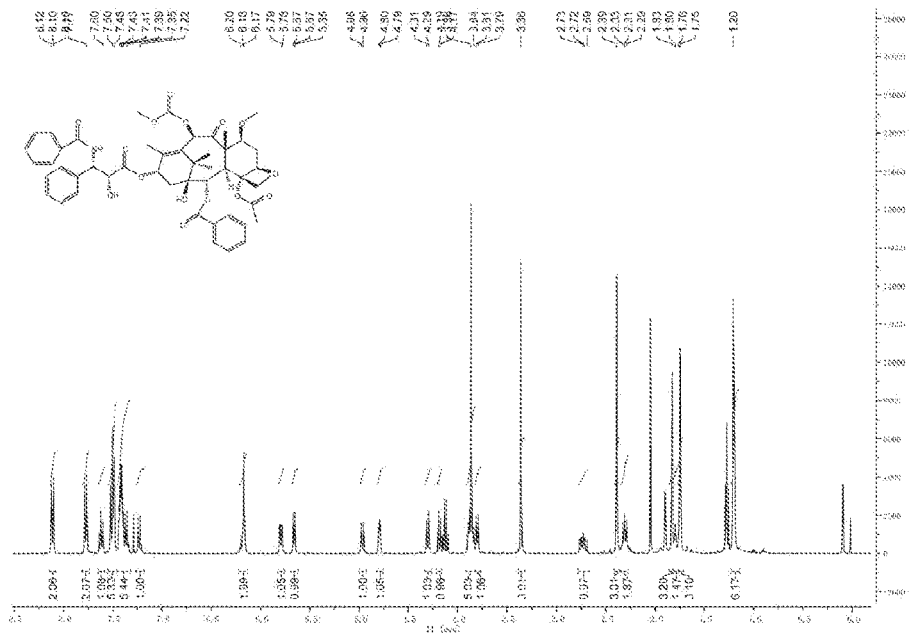
FIG. 15 is the $^1$H NMR spectrum of PCMI-27.
Figure 16:
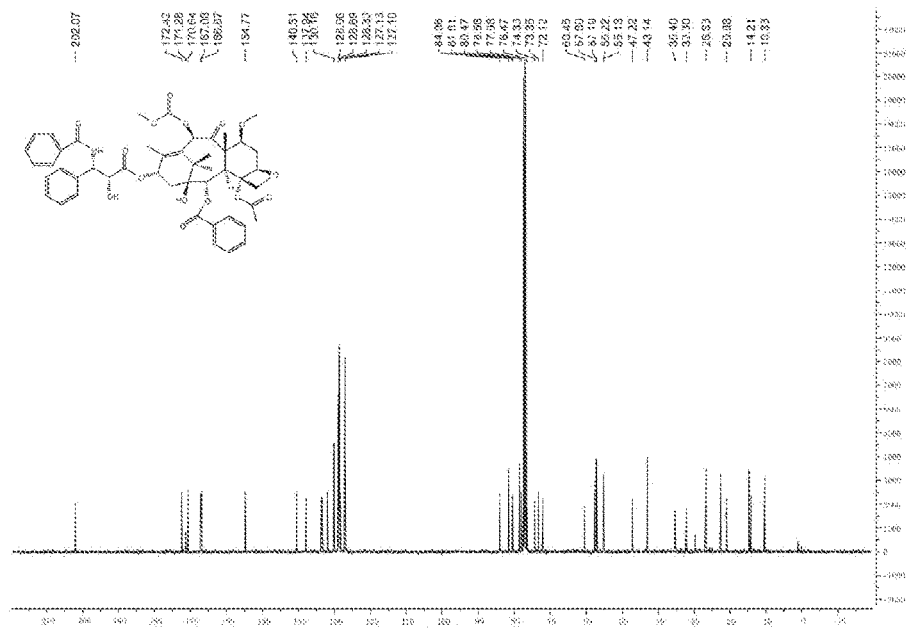
FIG. 16 is the $^{13}$C NMR spectrum of PCMI-27.
Figure 17:
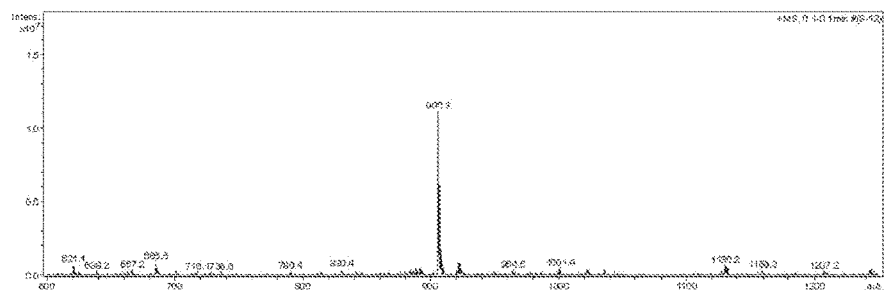
FIG. 17 is the MS spectrum of PCMI-27.
Figure 18:
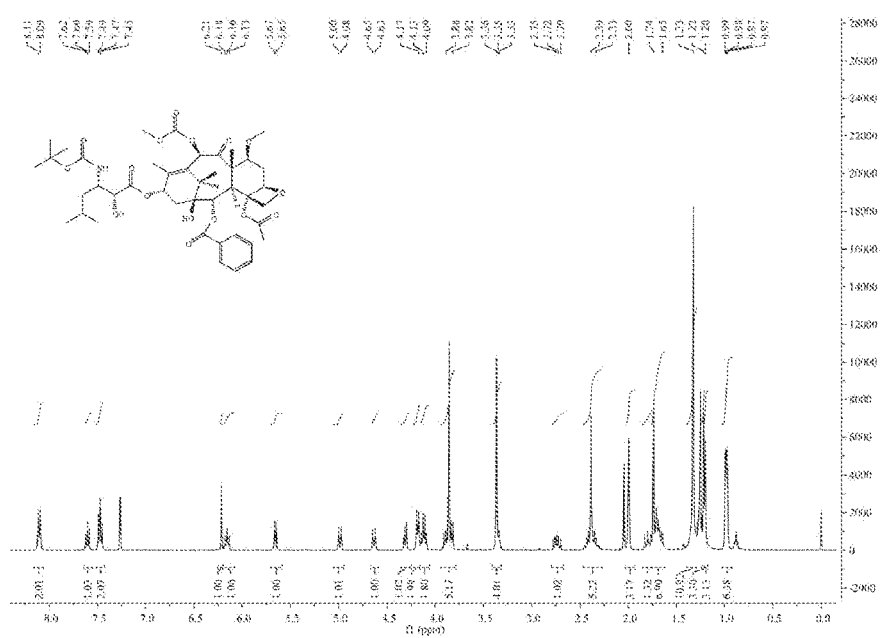
FIG. 18 is the $^1$H NMR spectrum of PCMI-28.
Figure 19:
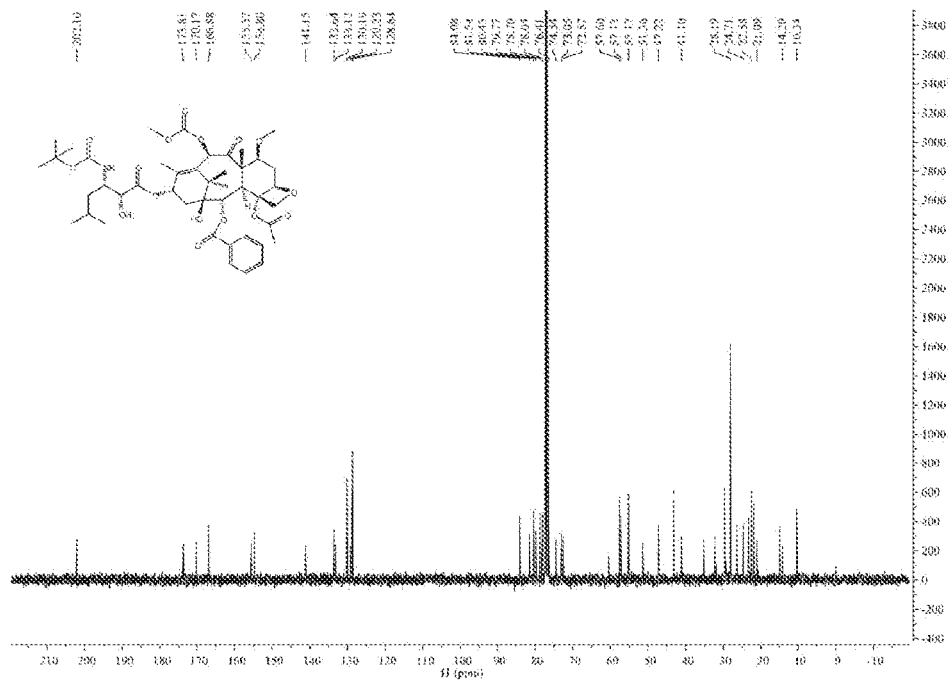
FIG. 19 is the $^{13}$C NMR spectrum of PCMI-28.
Figure 20:
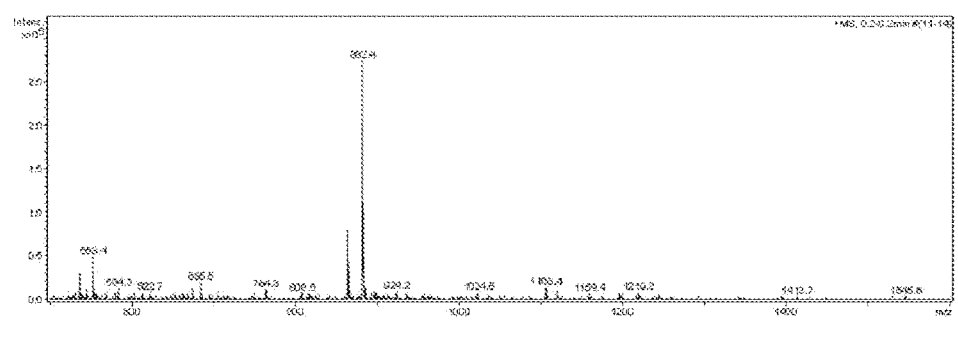
FIG. 20 is the MS spectrum of PCMI-28.
Figure 21:
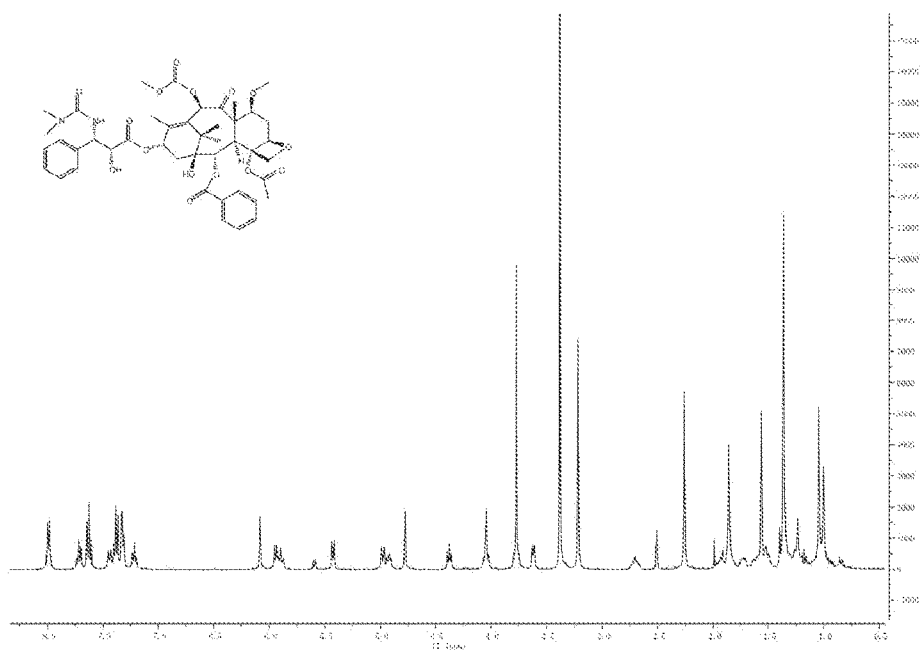
FIG. 21 is the $^1$H NMR spectrum of PCMI-29.
Figure 22:
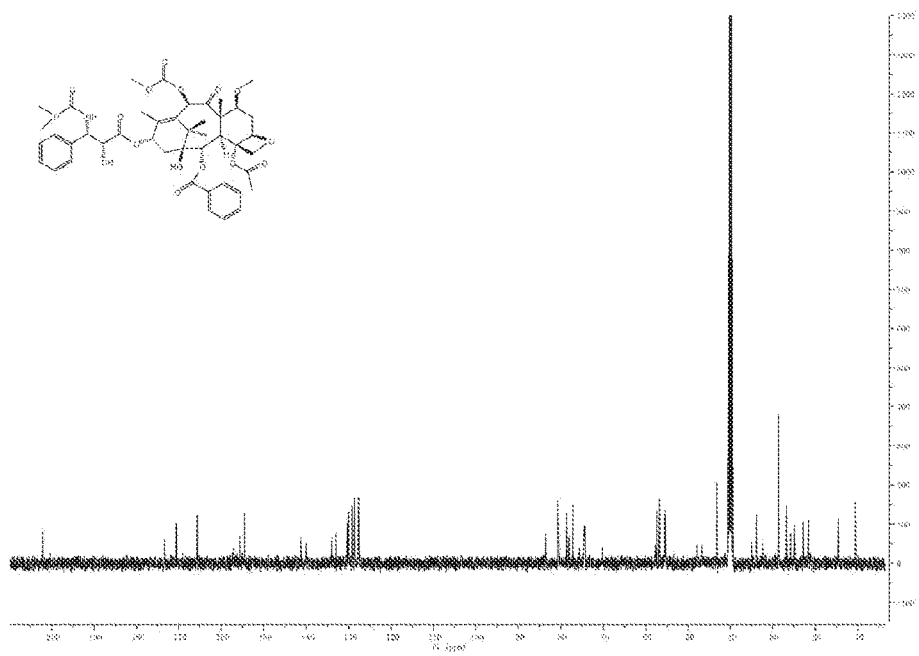
FIG. 22 is the $^{13}$C NMR spectrum of PCMI-29.
Figure 23:
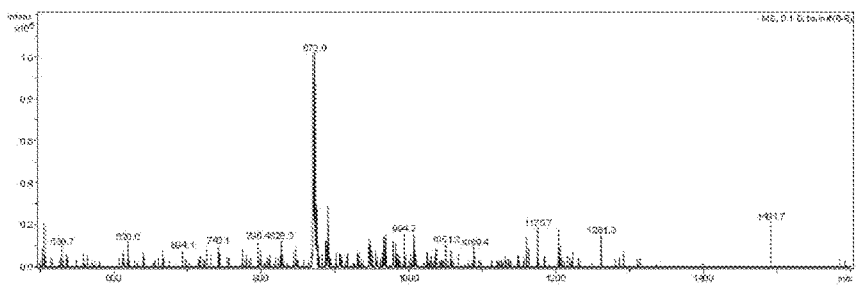
FIG. 23 is the MS spectrum of PCMI-29.
Figure 24:
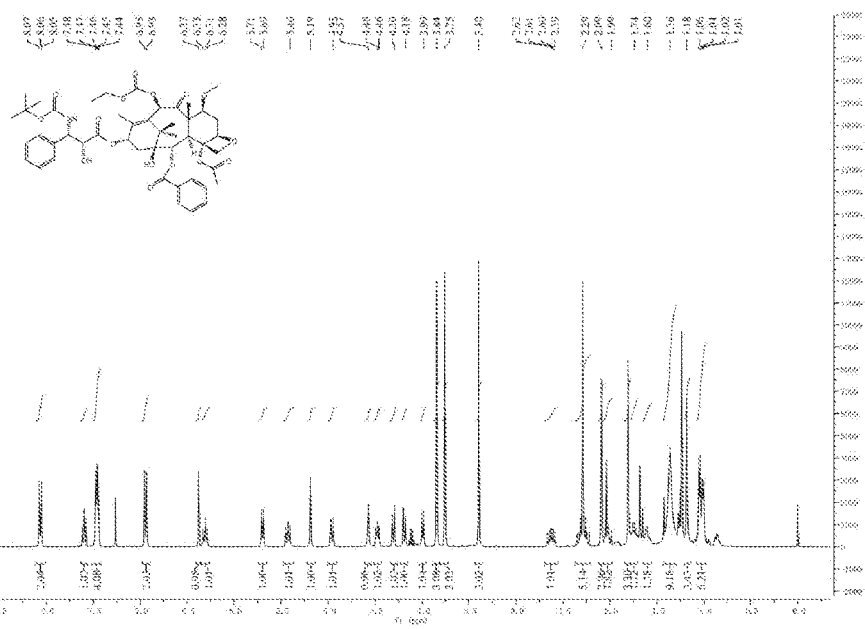
FIG. 24 is the $^1$H NMR spectrum of PCMI-30.
Figure 25:
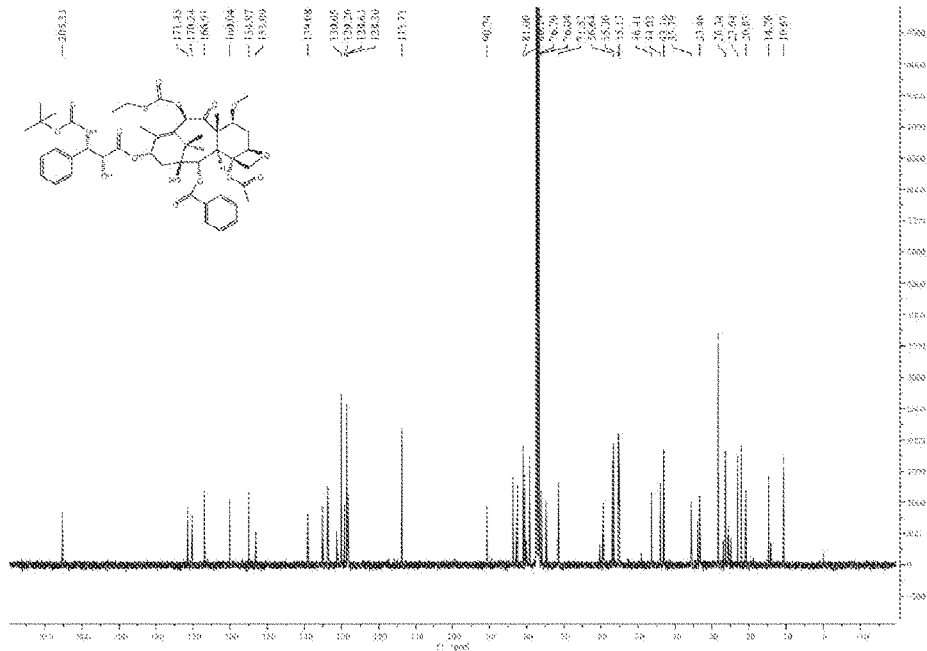
FIG. 25 is the $^{13}$C NMR spectrum of PCMI-30.
Figure 26:
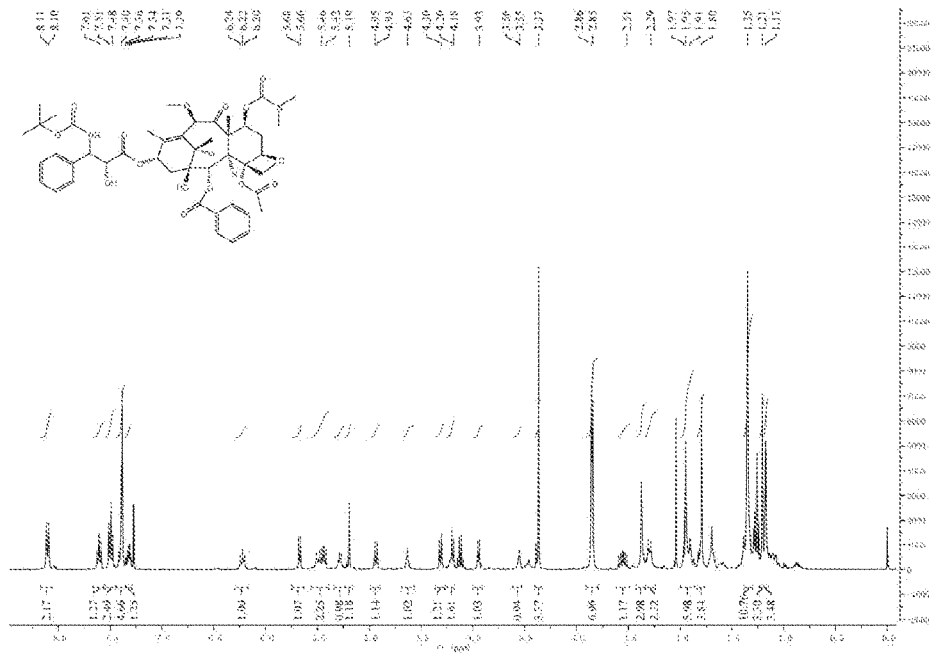
FIG. 26 is the $^1$H NMR spectrum of PCMI-31.
Figure 27:
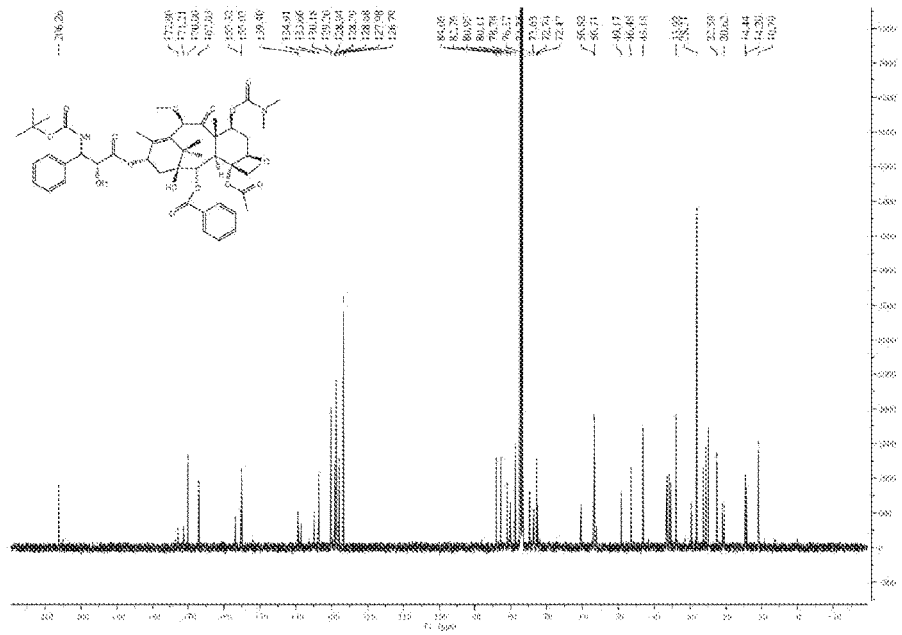
FIG. 27 is the $^{13}$C NMR spectrum of PCMI-31.
Figure 28:
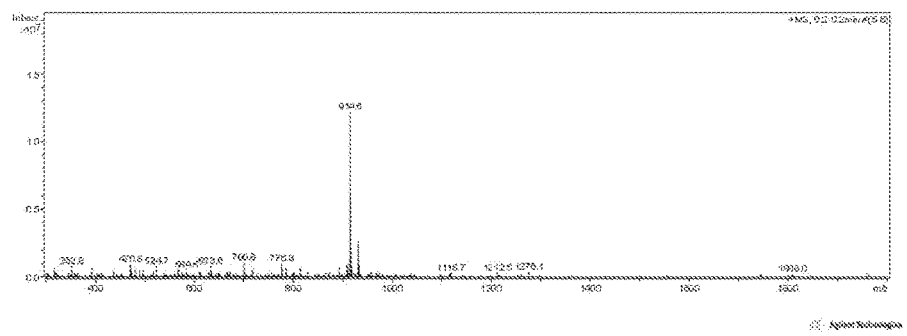
FIG. 28 is the MS spectrum of PCMI-31.
Figure 29:
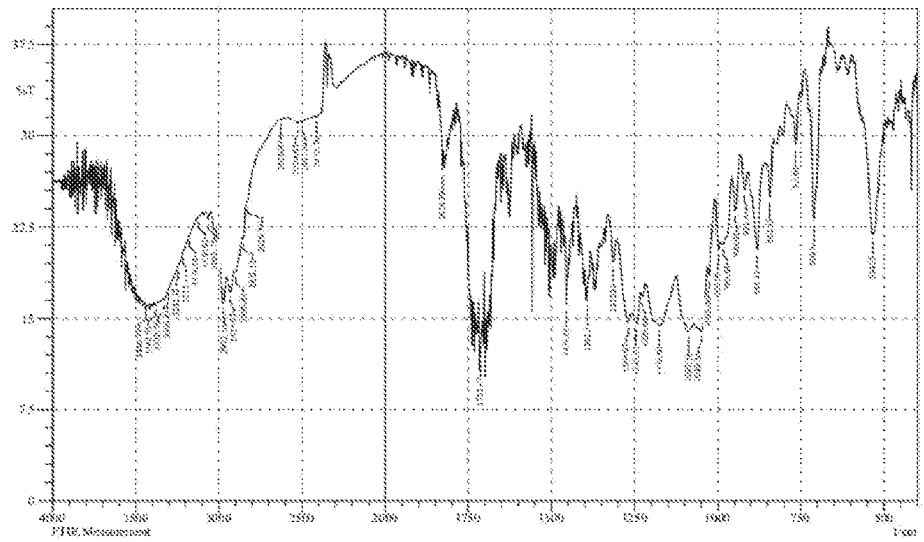
FIG. 29 is the IR spectrum of PCMI-31.
Figure 30:
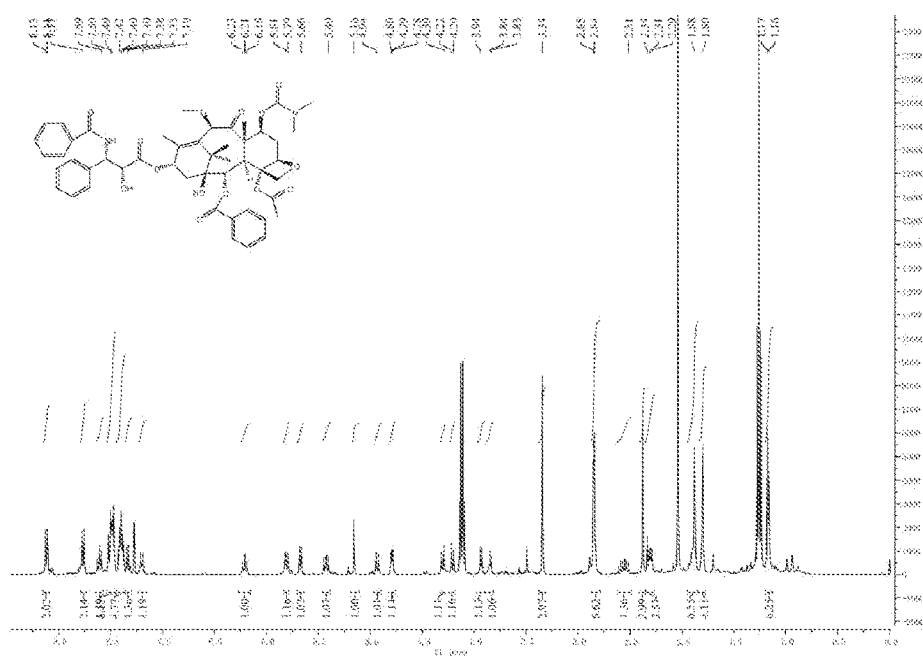
FIG. 30 is the $^1$H NMR spectrum of PCMI-32.
Figure 31:
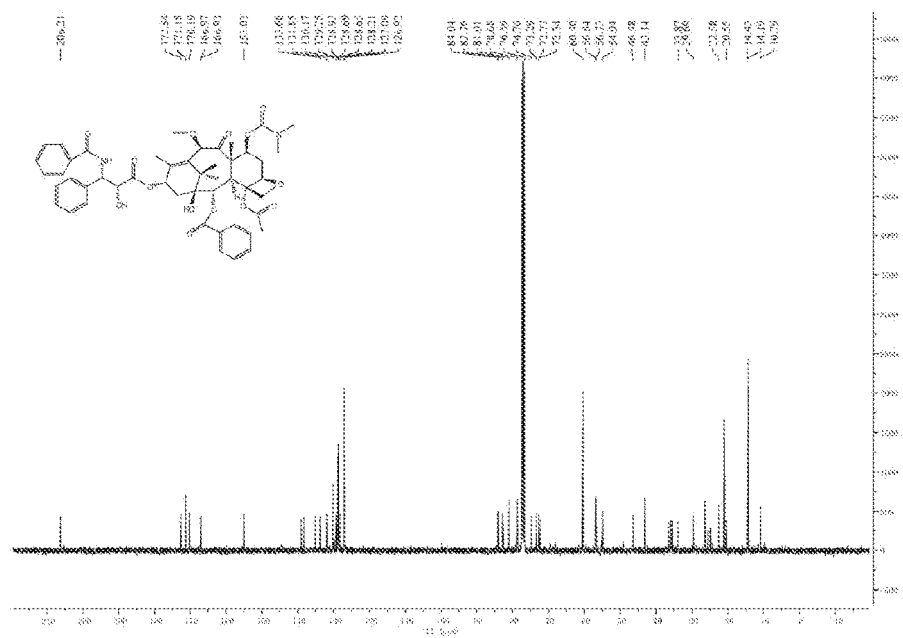
FIG. 31 is the $^{13}$C NMR spectrum of PCMI-32.
Figure 32:
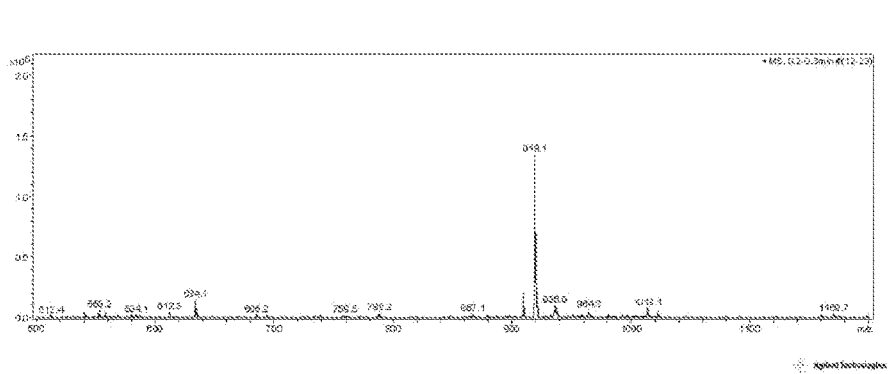
FIG. 32 is the MS spectrum of PCMI-32.
Figure 33:
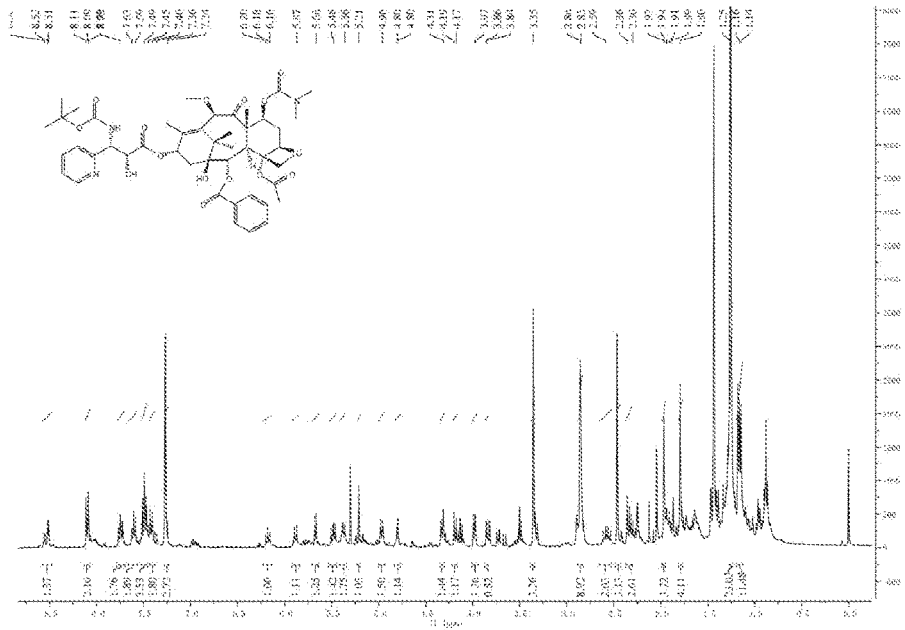
FIG. 33 is the $^1$H NMR spectrum of PCMI-33.
Figure 34:
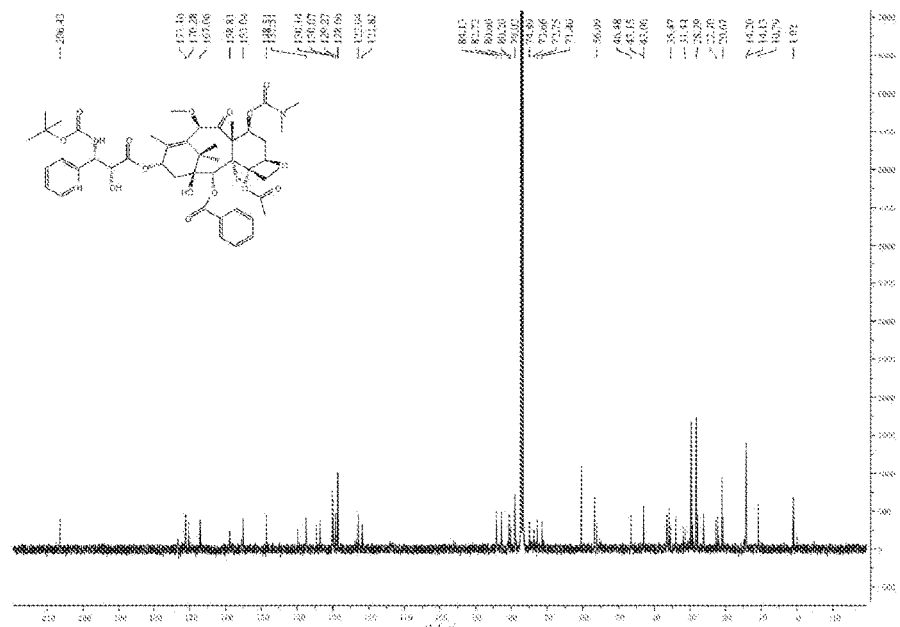
FIG. 34 is the $^{13}$C NMR spectrum of PCMI-33.
Figure 35:
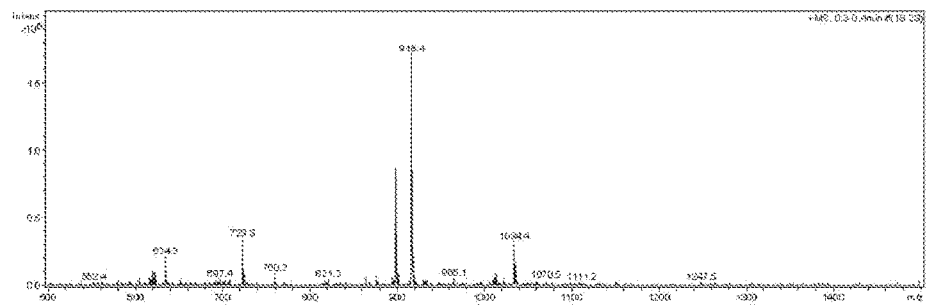
FIG. 35 is the MS spectrum of PCMI-33.
Figure 36:
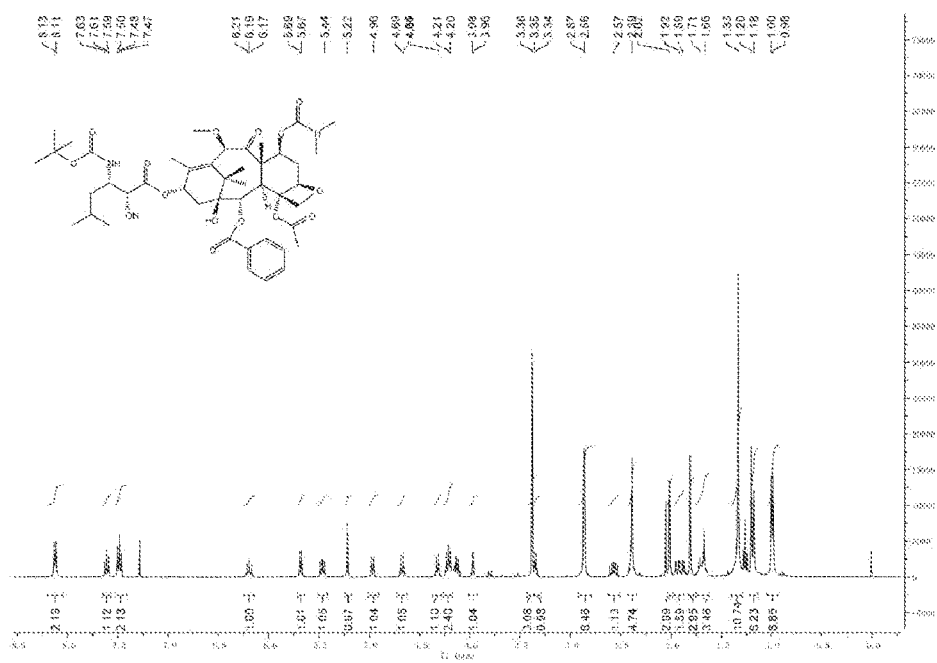
FIG. 36 is the $^1$H NMR spectrum of PCMI-34.
Figure 37:
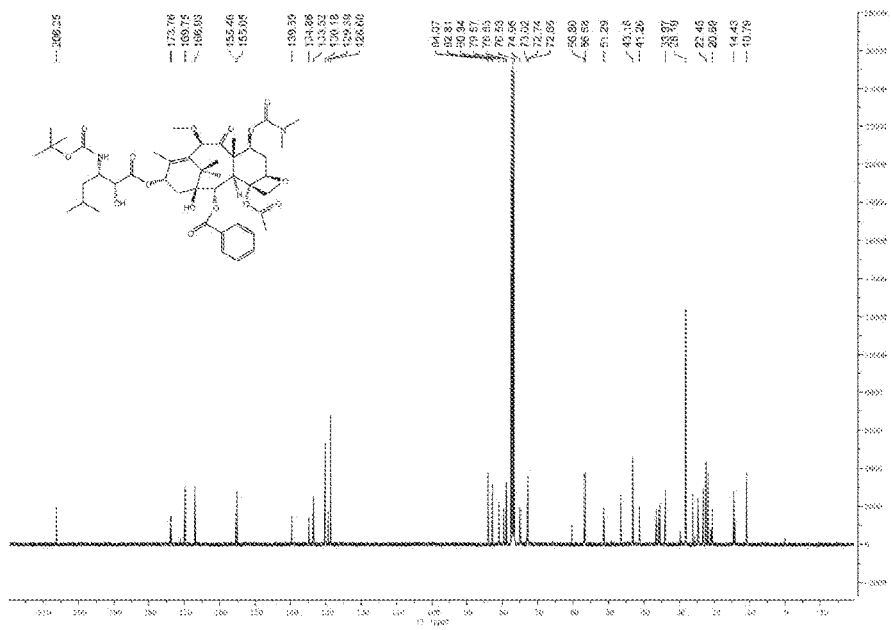
FIG. 37 is the $^{13}$C NMR spectrum of PCMI-34.
Figure 38:
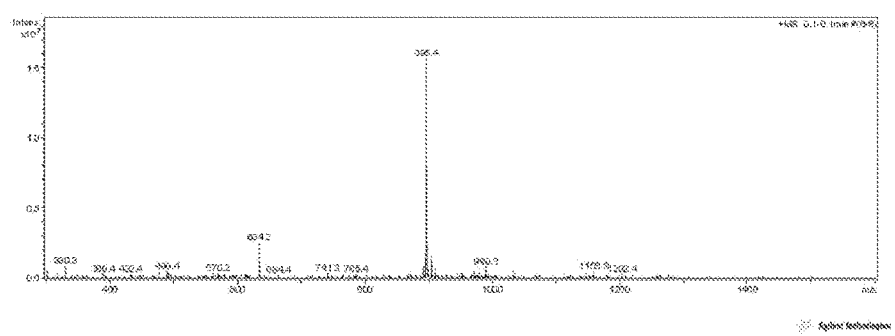
FIG. 38 is the MS spectrum of PCMI-34.
Figure 39:
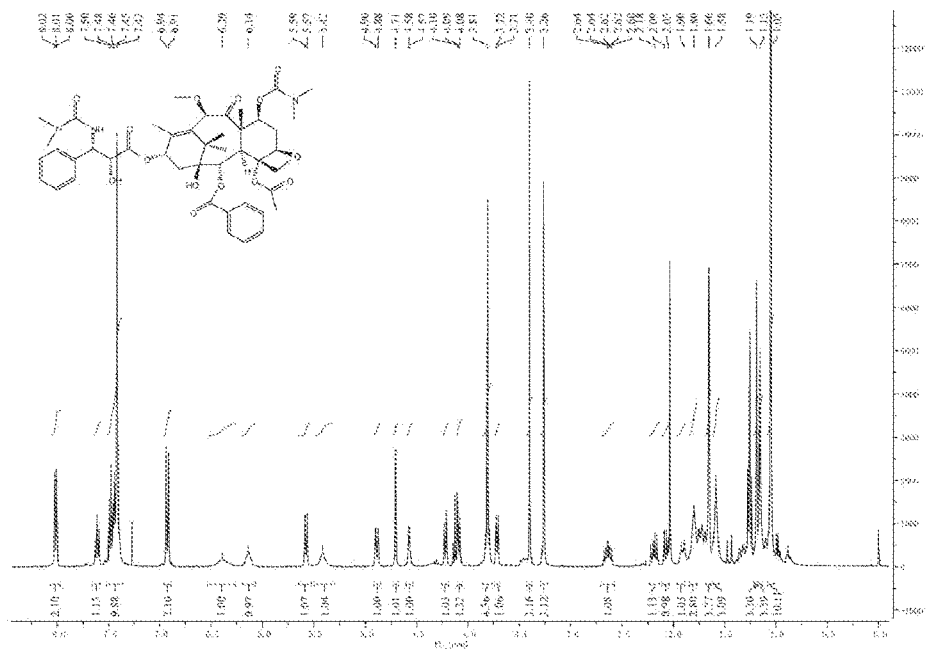
FIG. 39 is the $^1$H NMR spectrum of PCMI-35.
Figure 40:
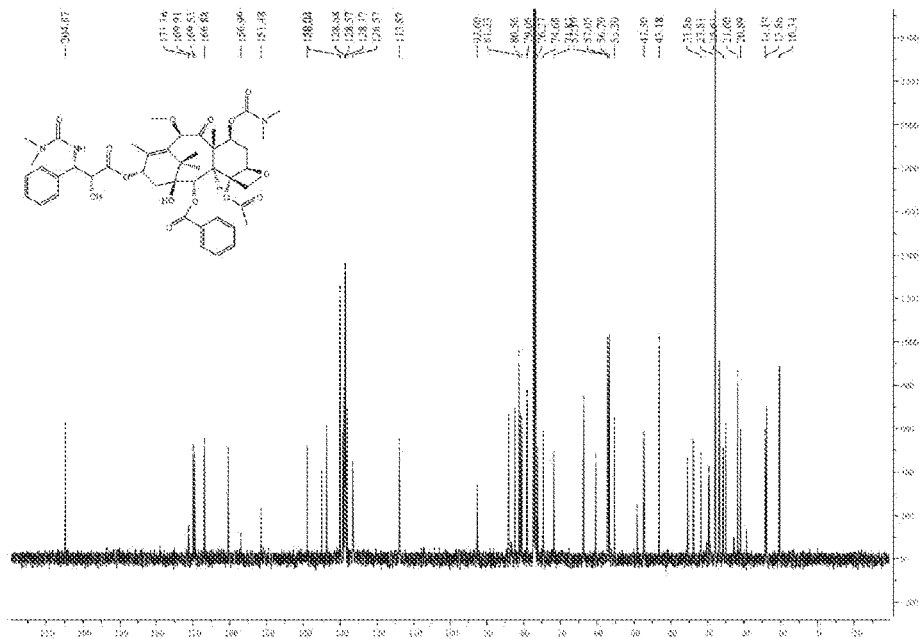
FIG. 40 is the $^{13}$C NMR spectrum of PCMI-35.
Figure 41:
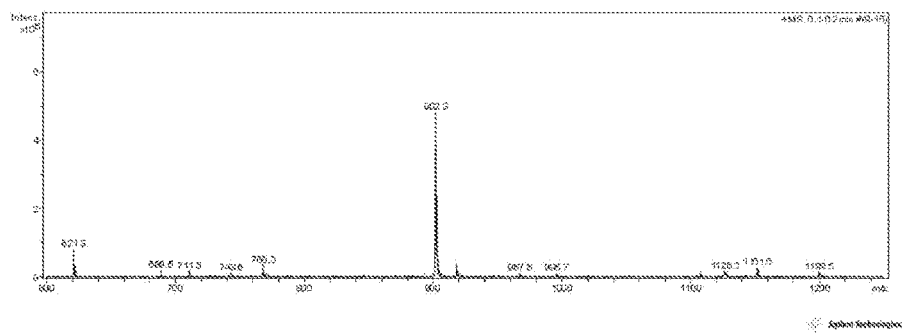
FIG. 41 is the MS spectrum of PCMI-35.
Figure 42:
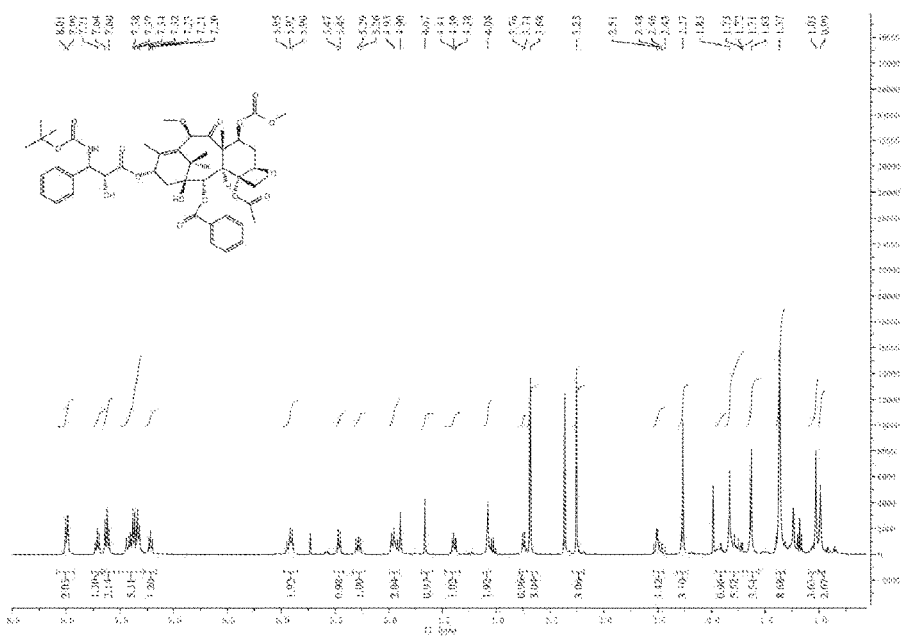
FIG. 42 is the $^1$H NMR spectrum of PCMI-36.
Figure 43:
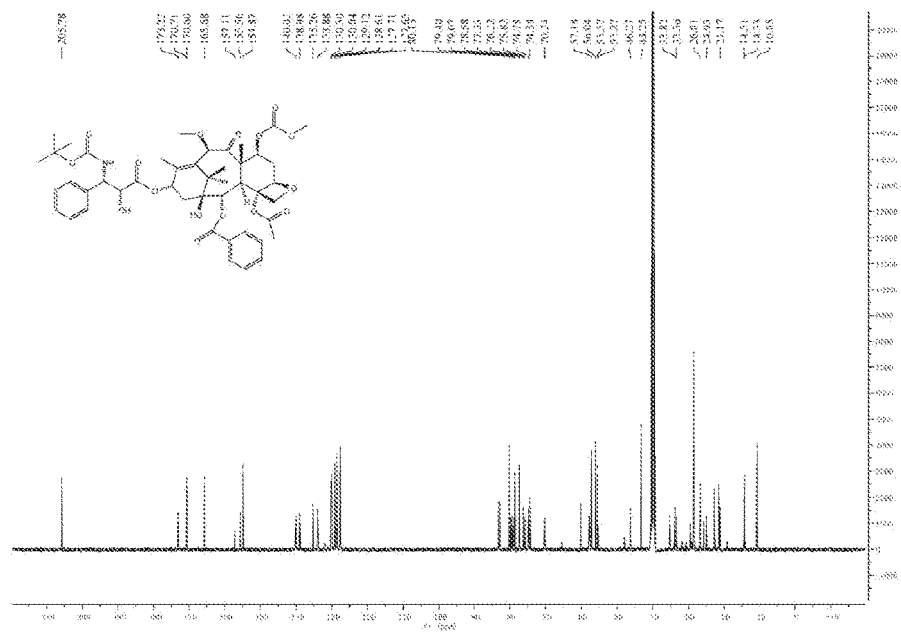
FIG. 43 is the $^{13}$C NMR spectrum of PCMI-36.
Figure 44:
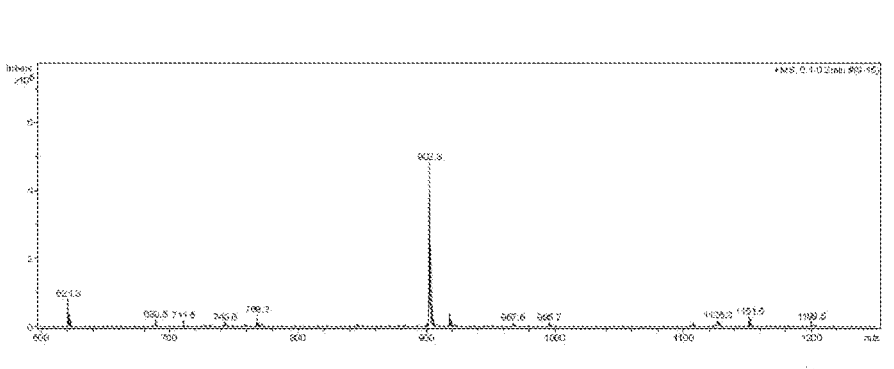
FIG. 44 is the MS spectrum of PCMI-36.
Figure 45:
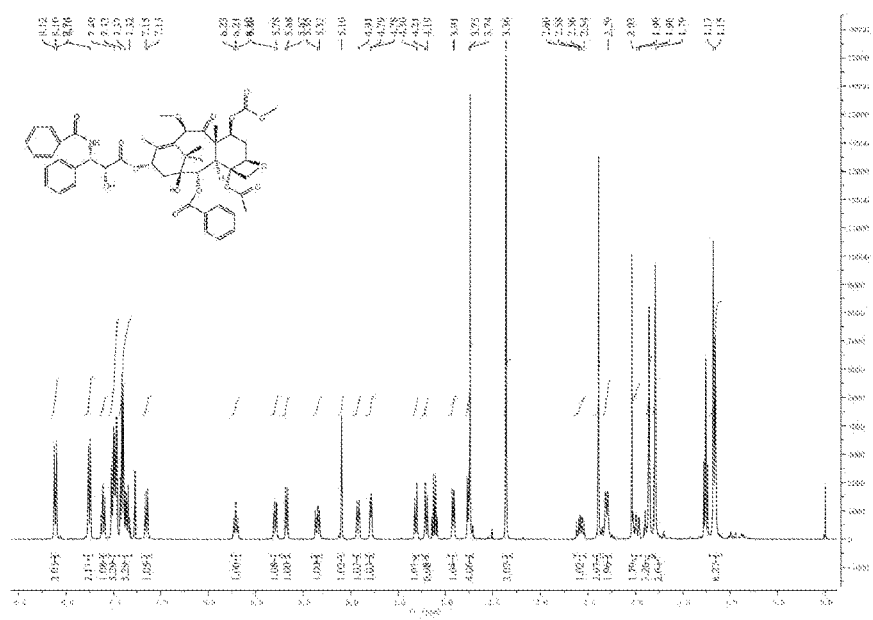
FIG. 45 is the $^1$H NMR spectrum of PCMI-37.
Figure 46:
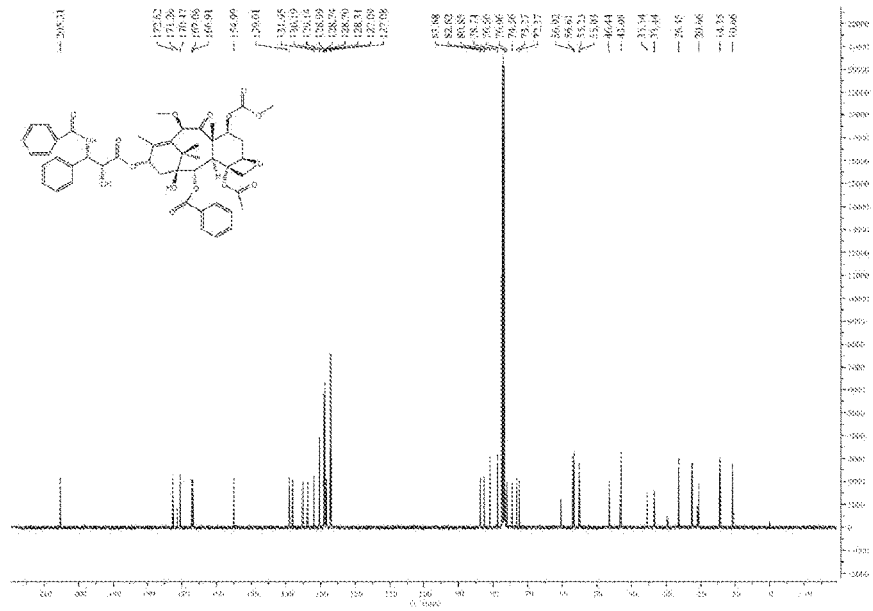
FIG. 46 is the $^{13}$C NMR spectrum of PCMI-37.
Figure 47:
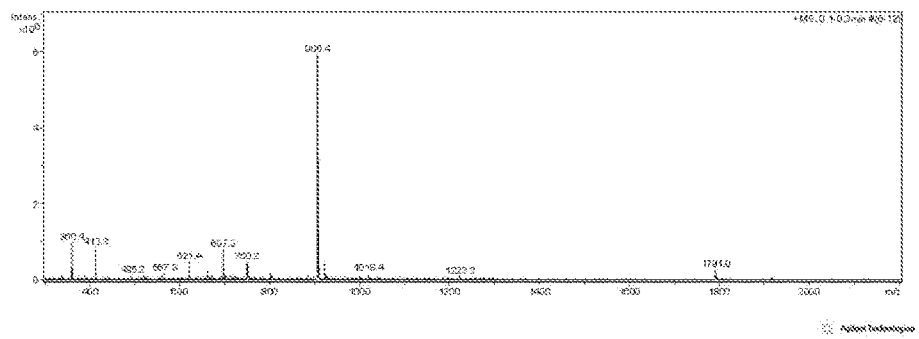
FIG. 47 is the MS spectrum of PCMI-37.
Figure 48:
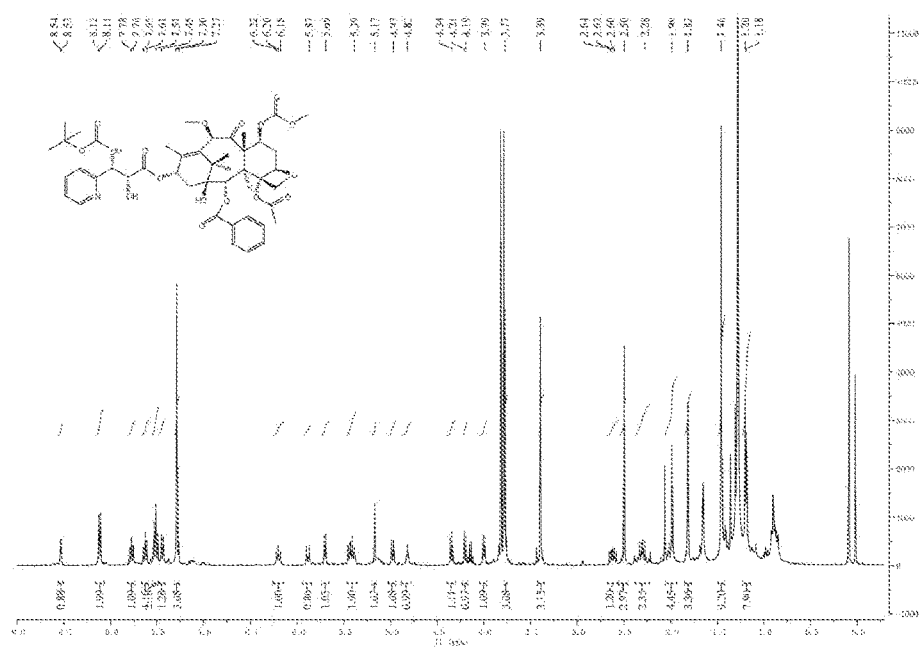
FIG. 48 is the $^1$H NMR spectrum of PCMI-38.
Figure 49:
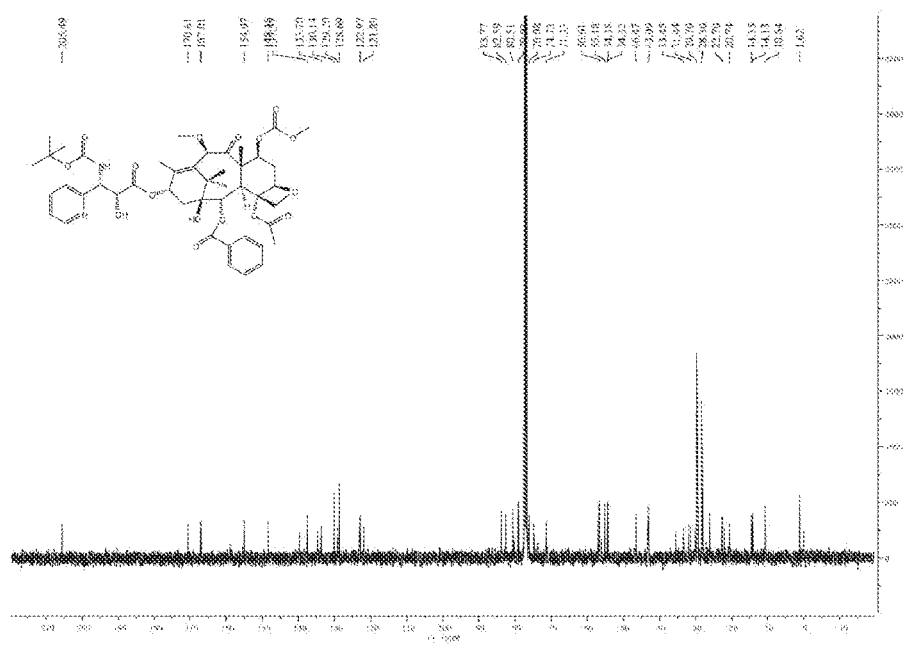
FIG. 49 is the $^{13}$C NMR spectrum of PCMI-38.
Figure 50:
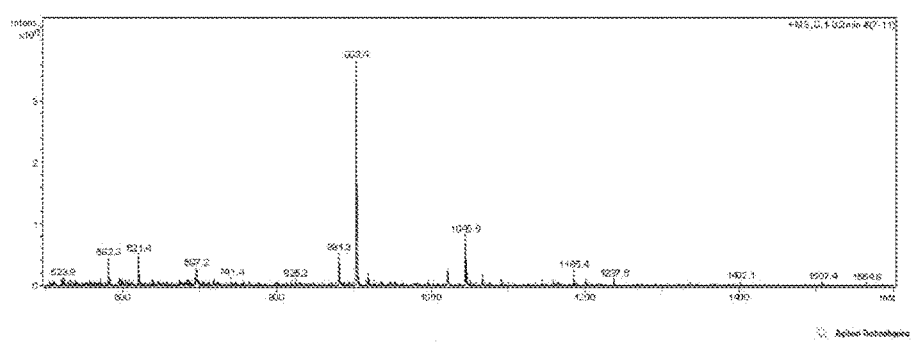
FIG. 50 is the MS spectrum of PCMI-38.
Figure 51:
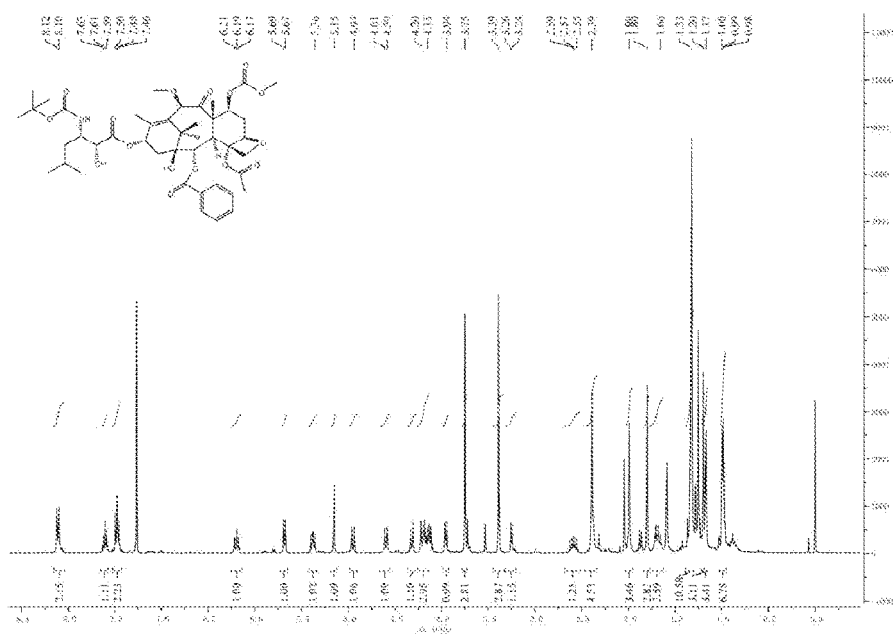
FIG. 51 is the $^1$H NMR spectrum of PCMI-39.
Figure 52:
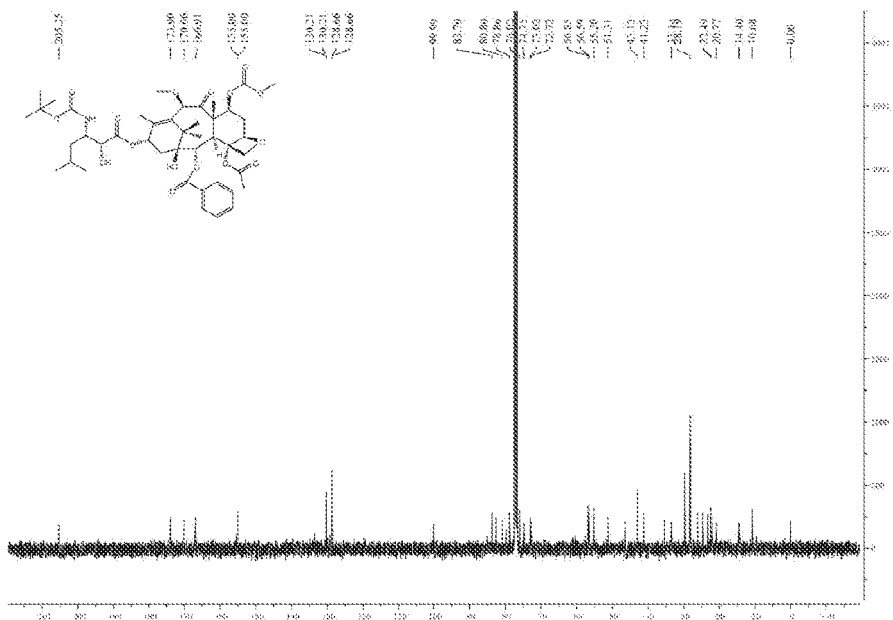
FIG. 52 is the $^{13}$C NMR spectrum of PCMI-39.
Figure 53:
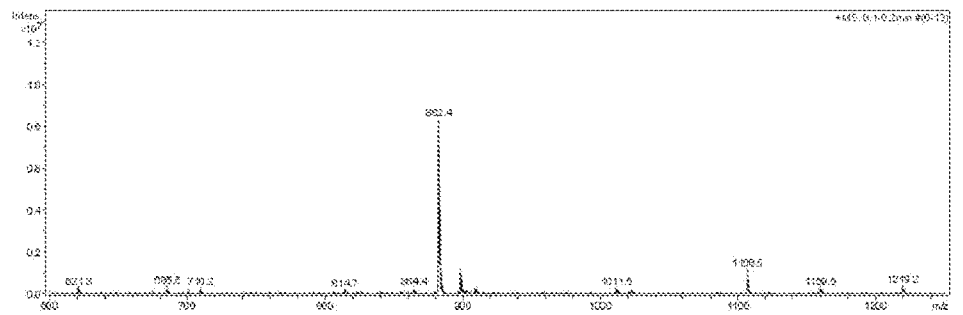
FIG. 53 is the MS spectrum of PCMI-39.
Figure 54:
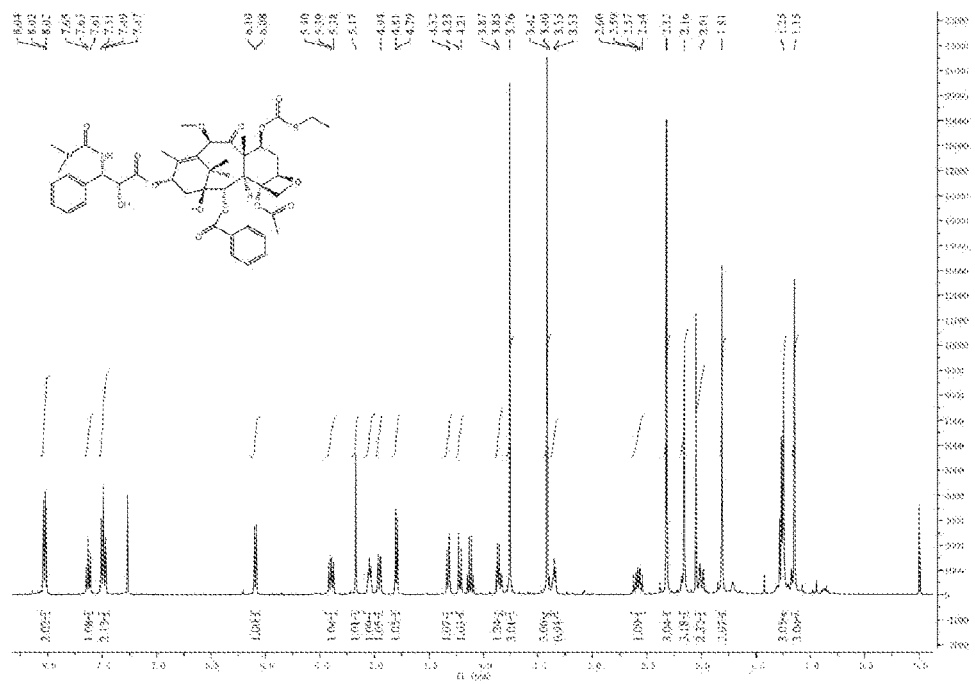
FIG. 54 is the $^1$H NMR spectrum of PCMI-40.
Figure 55:
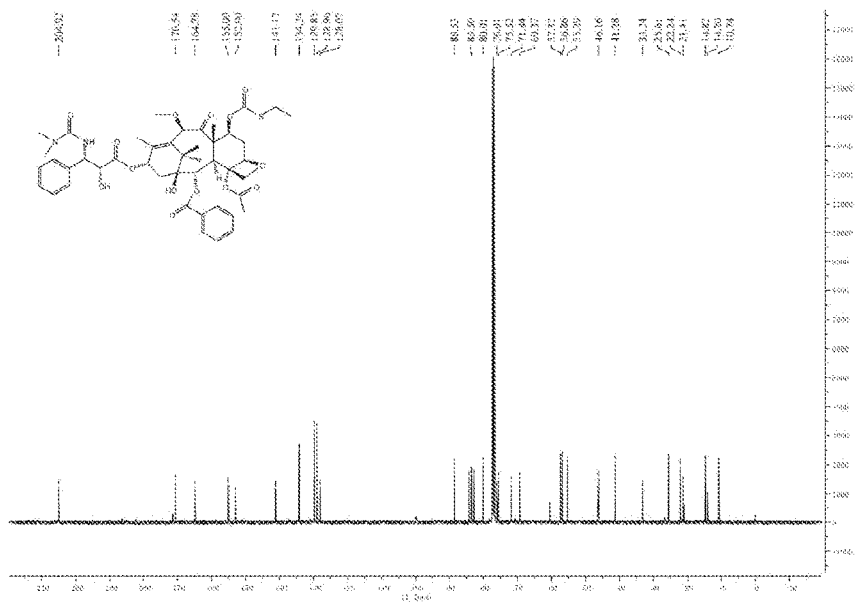
FIG. 55 is the $^{13}$C NMR spectrum of PCMI-40.
Figure 56:
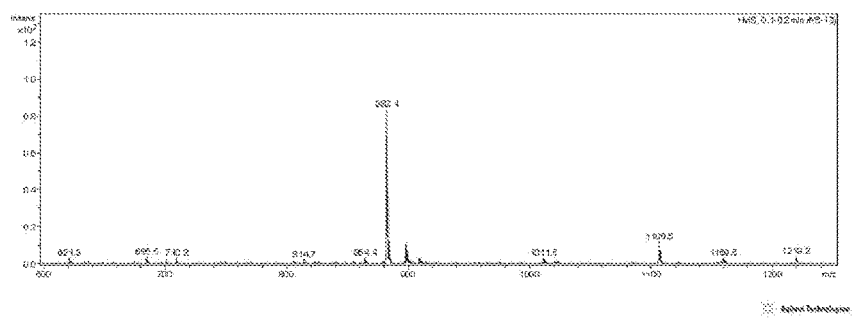
FIG. 56 is the MS spectrum of PCMI-40.
Figure 57:
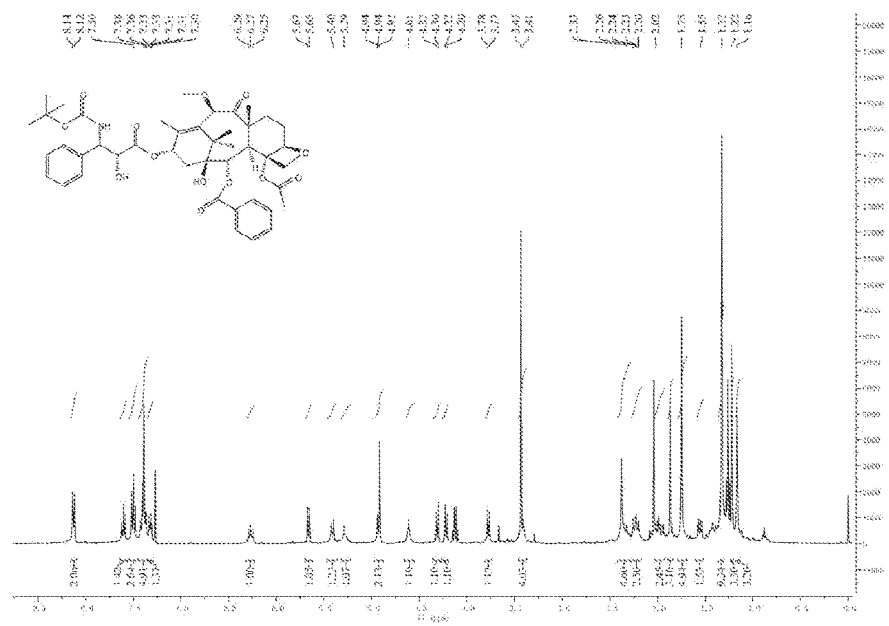
FIG. 57 is the $^1$H NMR spectrum of PCMI-41.
Figure 58:
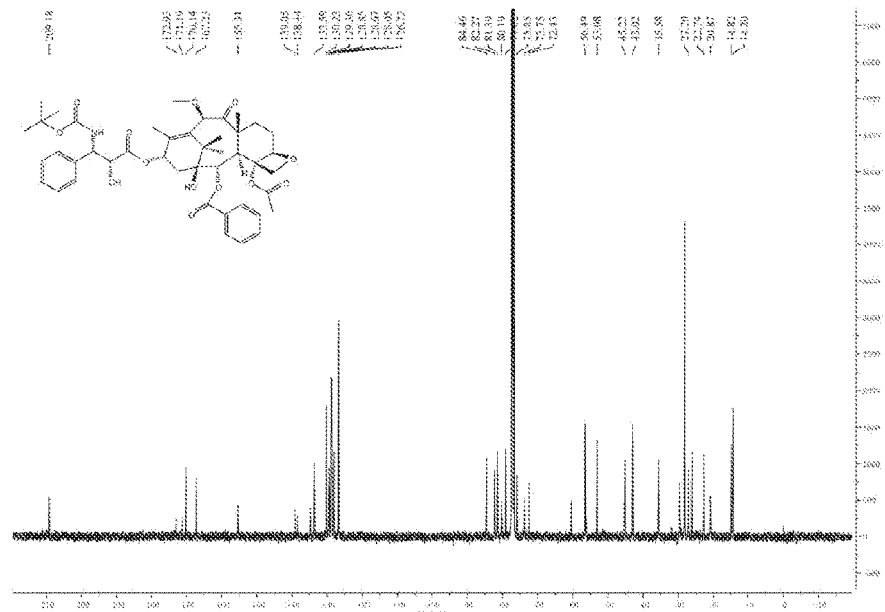
FIG. 58 is the $^{13}$C NMR spectrum of PCMI-41.
Figure 59:
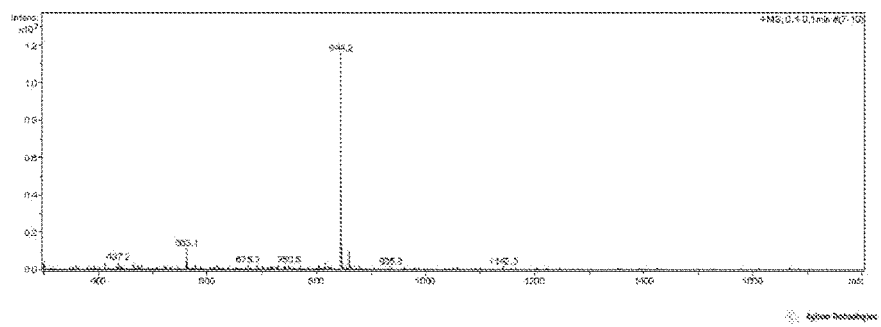
FIG. 59 is the MS spectrum of PCMI-41.
Figure 60:
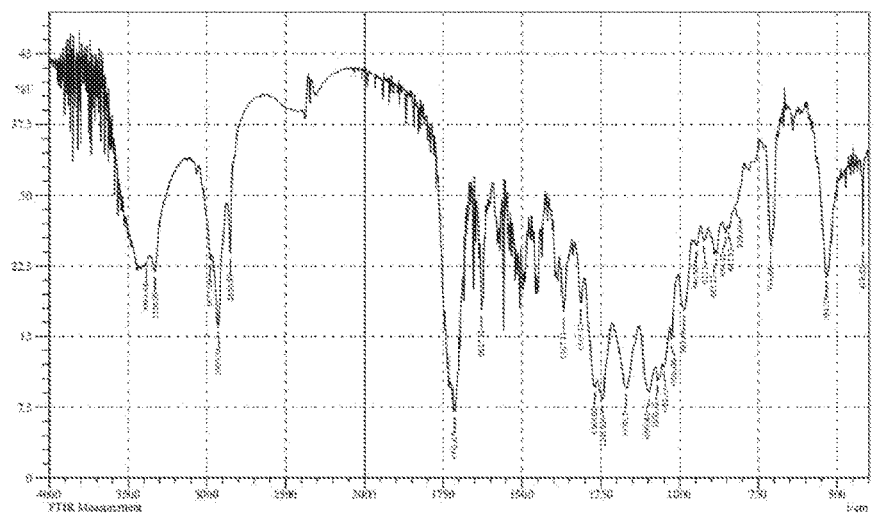
FIG. 60 is the IR spectrum of PCMI-41.
Figure 61:
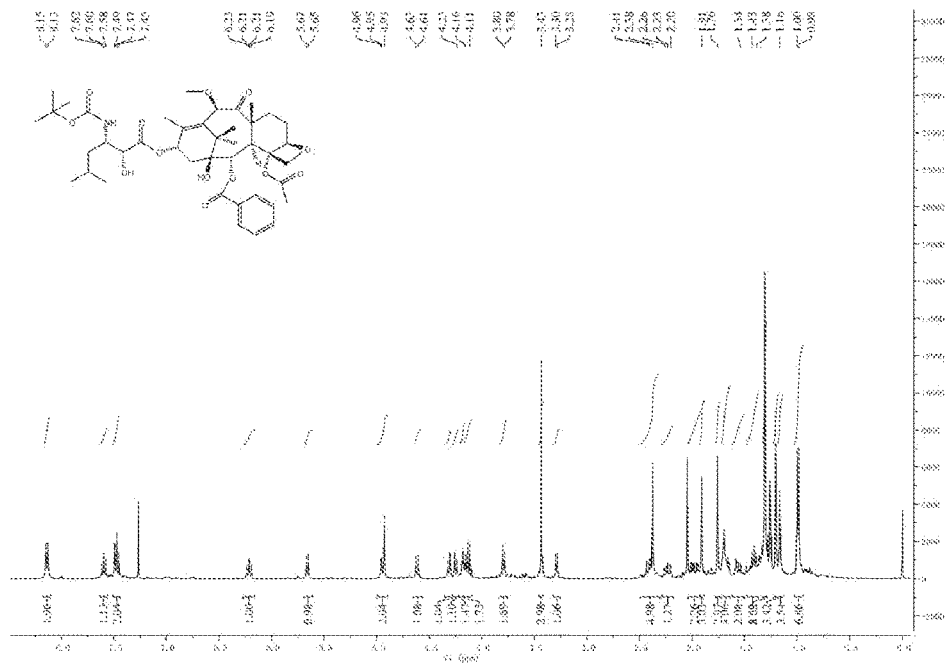
FIG. 61 is the $^1$H NMR spectrum of PCMI-42.
Figure 62:
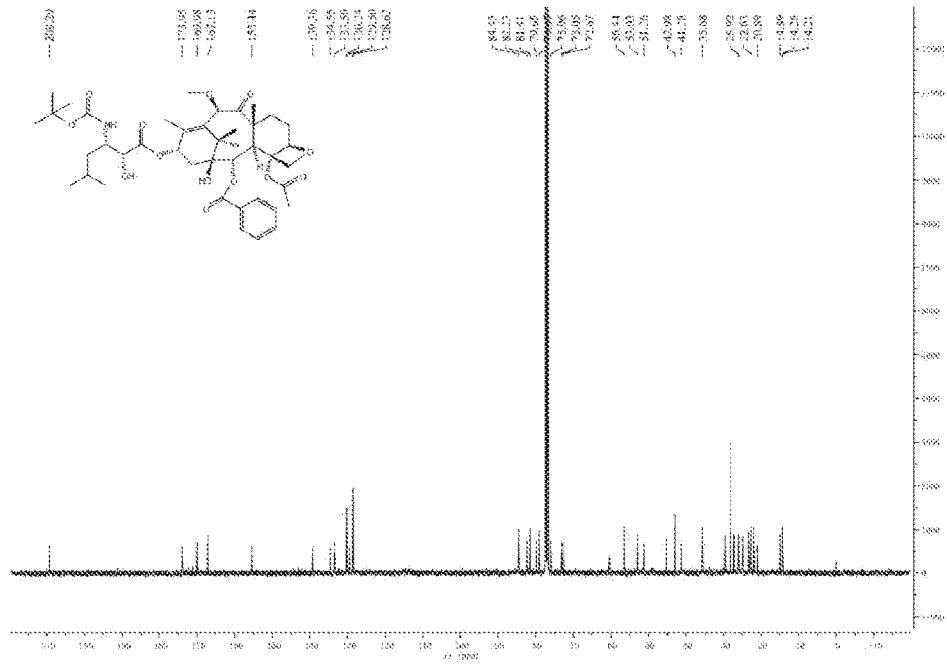
FIG. 62 is the $^{13}$C NMR spectrum of PCMI-42.
Figure 63:
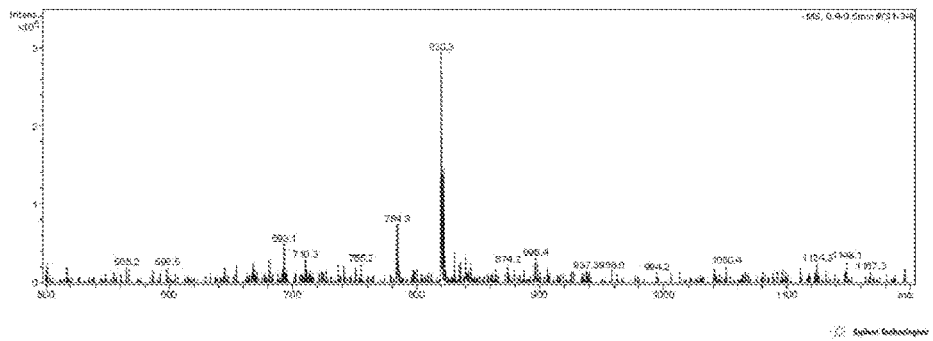
FIG. 63 is the MS spectrum of PCMI-42.
Figure 64:
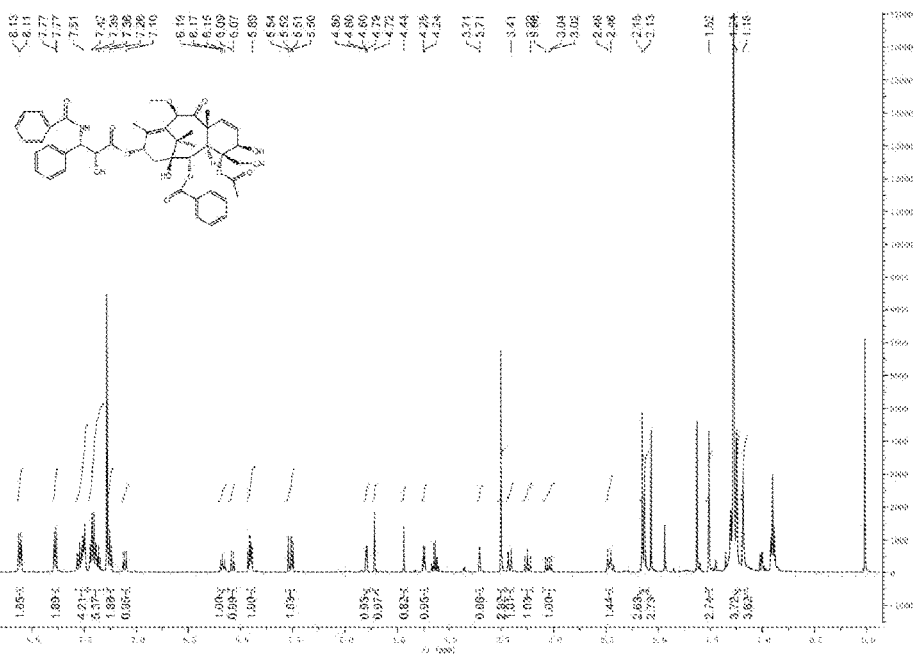
FIG. 64 is the $^1$H NMR spectrum of PCMI-43.
Figure 65:
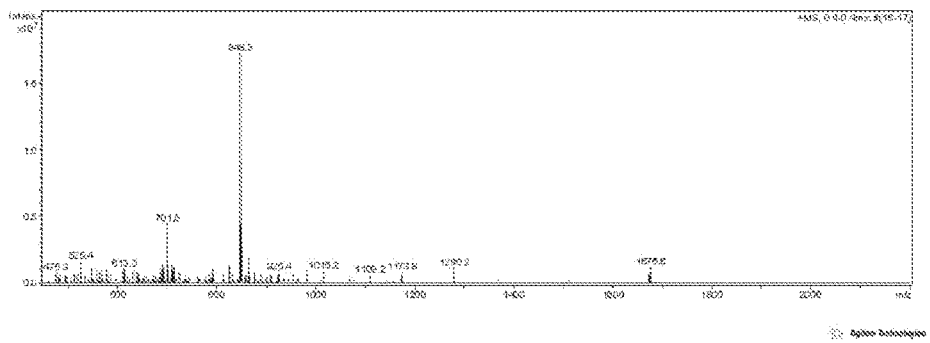
FIG. 65 is the MS spectrum of PCMI-43.
Figure 66:
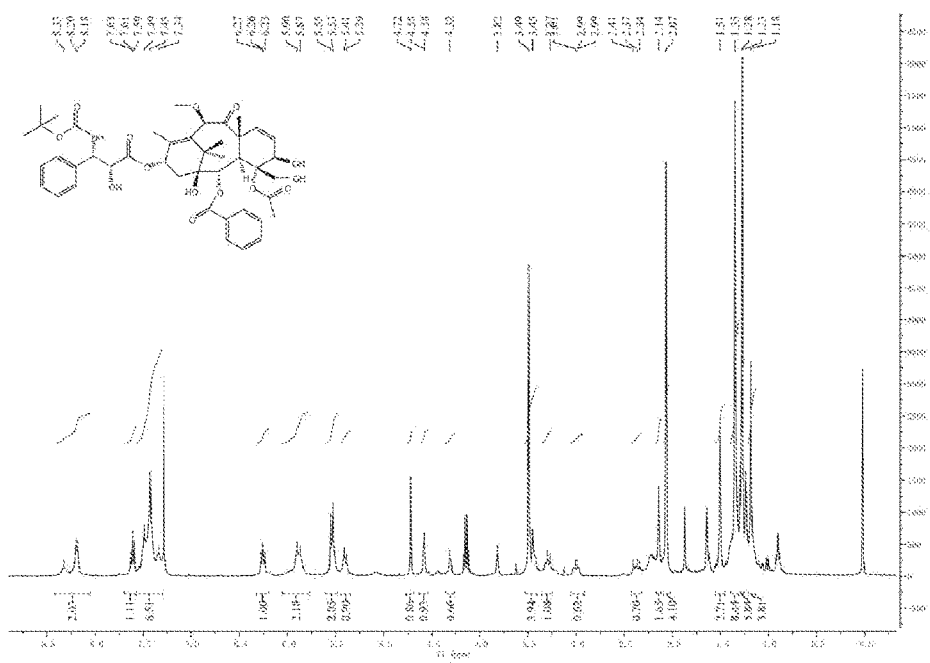
FIG. 66 is the $^1$H NMR spectrum of PCMI-44.
Figure 67:
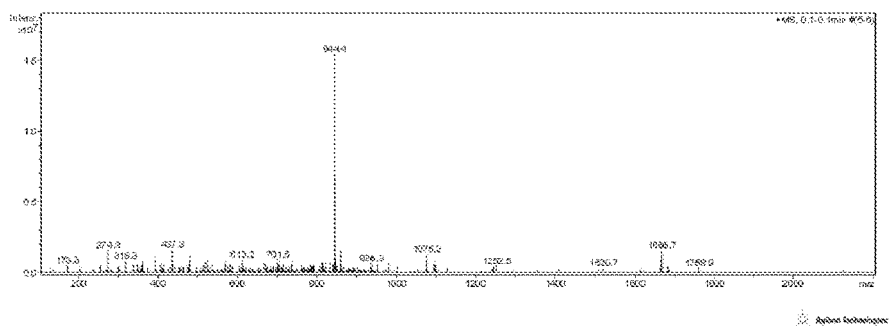
FIG. 67 is the MS spectrum of PCMI-44.

The term "alkyl" used herein refers to the group consisting of carbon and hydrogen atoms only without any unsaturated degree (such as double bonds, triple bonds or rings), which covers all kinds of possible geometric isomers and stereo-isomers thereof. The groups are attached to the rest of the molecule by a single bond. The term "C1-C6 alkyl" used herein refers to the above defined alkyl with a carbon number of 1-6. As non-limiting examples of C1-C6 alkyl, the following groups with straight chain or branched chain may be enumerated: methyl, ethyl, n-propyl, isopropyl, n-butyl, isobutyl, sec-butyl, t-butyl, n-pentyl and isomers thereof, as well as n-hexyl and isomers thereof.

The term "alkenyl" used herein refers to the group which is formed from the above mentioned alkyl group (except methyl) by having one or more double bonds. The term "C1-C6 alkenyl" refers to the above defined alkenyl with a carbon number of 1-6.

The term "alkynyl" used herein refers to the group which is formed from the above mentioned alkyl group (except methyl) by having one or more triple bonds. The term "C1-C6 alkynyl" refers to the above defined alkynyl with a carbon number of 1-6.

The term "hydrocarbon group" used herein refers to the group consisting of carbon and hydrogen atoms only. The term "substituted hydrocarbon group" refers to the above defined alkyl, alkenyl or alkynyl group and the like having substituents. The substituent can be a hydroxyl group, an amino group and the like.

The term "heterocyclic group" used herein refers to an aromatic 5-14 member ring or a non-aromatic 3-15 member ring consisting of carbon atoms and heteroatoms independently selected from N, O or S. The aromatic ring may be monocyclic, bicyclic or polycyclic, in which the bicyclic and polycyclic groups are formed from monocyclic groups by connected with each other through single bonds or in a fused way. As non-limiting examples of heteroaryl groups, the following groups may be enumerated: oxazolyl, isoxazolyl, imidazolyl, furyl, indolyl, isoindolyl, pyrrolyl, triazolyl, triazinyl, tetrazolyl, thienyl, thiazolyl, isothiazolyl, pyridinyl, pyrimidinyl, pyrazinyl, pyridazinyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, thiadiazolyl, indolizinyl, acridinyl, phenazinyl, phthalazinyl, coumarinyl, pyrazolopyridinyl, pyridinopyridazinyl, pyrrolopyridinyl, imidazopyridinyl, pyrazolopyridazinyl; and the groups formed from the above heteroaryl groups by connected with each other through single bonds or in a fused way. The non-aromatic ring may be monocyclic, bicyclic or polycyclic, and fused ring, bridged ring or spiro ring, which may optionally contain one or more double bonds. As non-limiting examples of the heterocyclic groups, the following groups may be enumerated: azepinyl, acridinyl, benzodioxolyl, benzodioxanyl, chromanyl, dioxolanyl, dioxaphospholanyl, decahydro isoquinolinyl, indanyl, indolinyl, isoindolinyl, isochromanyl, isothiazolidinyl, isoxazolidinyl, morpholinyl, oxazolinyl, oxazolidinyl, oxadiazolyl, 2-oxo-piperazinyl, 2-oxo-piperidinyl, 2-oxopyrrolidinyl, 2-oxo-azepinyl, octahydroindolyl, octahydroisoindolyl, perhydroazepinyl, piperazinyl, 4-piperidonyl, piperidinyl, phenothiazinyl, phenoxazinyl, quinuclidinyl, tetrahydroisoquinolinyl, tetrahydrofuranyl, tetrahydropyranyl, tetrahydropyrrolidinyl, thiazolinyl, thiazolidinyl, thiomorpholinyl, thiomorpholine sulfoxide and thiomorpholinyl sulfone.

The term "aryl" used herein refers to an aromatic ring consisting of at least 6 carbon atoms, which may be monocyclic, bicyclic or polycyclic, in which bicyclic and polycyclic rings may be formed from monocyclic rings by connected with each other through single bonds or in a fused way. As non-limiting examples of the aryl groups, the following groups may be enumerated: phenyl, naphthyl, anthryl, phenanthryl, indenyl, pyrenyl, perylenyl, azulenyl, acenaphthenyl, fluorenyl, benzoacenaphthenyl, triphenylenyl, chrysenyl, biphenyl, binaphthyl and the like.

The term "substituted aromatic group" used herein refers to the above defined aromatic group having substituents. The substituent may be an alkyl, an alkenyl, an alkynyl, a hydroxyl, an amino and the like.

The present invention provides taxanes compounds having the structure represented by the following general formula I:

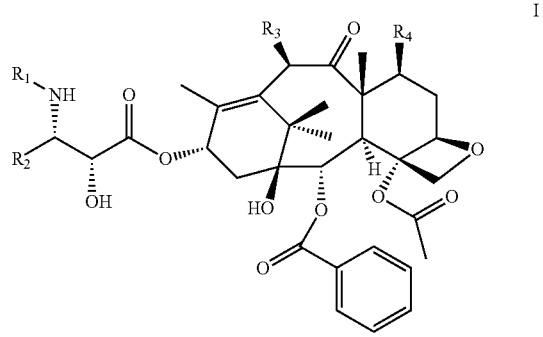

wherein,
$R_1$ is —$COR_6$, —$COOR_6$, or —$CONR_{7a}R_{7b}$;
$R_2$ is a C1-C6 alkyl, a C1-C6 alkenyl group, a substituted hydrocarbon group, a heterocyclic group, an aromatic group or a substituted aromatic group;
$R_3$ is —$OR_6$, —$OCOOR_6$—$OCOSR_6$, or —$OCONR_{7a}R_{7b}$;

R₄ is —OR₆, —OCOOR₆, —OCOSR₆, —OCONR₇ₐR₇ᵦ, or H;

wherein, R₆ is a C1-C6 alkyl, a C1-C6 alkenyl, a C1-C6 alkynyl, a substituted hydrocarbon group, an aromatic group or a heterocyclic group: R₇ₐ and R₇ᵦ are respectively hydrogen, a hydrocarbon group, a substituted hydrocarbon group or a heterocyclic group.

Preferably, R₁ is benzoyl, t-butyloxycarbonyl, or N,N'-dimethylcarbamoyl:

R₂ is phenyl,

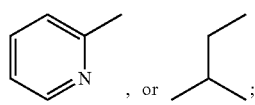
, or

R₃ is —OMe, —OCOOCH₃, —OCON(CH₃)₂, or —OCOSC₂H₅;

R₄ is —OMe, —OCOOCH₃, —OCON(CH₃)₂, —OCOSC₂H₅, or H.

Further, the present invention provides taxanes compounds having the structure represented by the following general formula II:

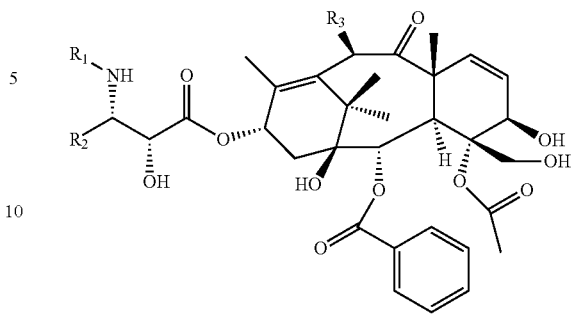

wherein,
R₁ is —COR₆, or —COOR₆;
R₂ is an aromatic group;
R₃ is —OR₆;
wherein, R₆ is a C1-C6 alkyl, a C1-C6 alkenyl, a C1-C6 alkynyl, a substituted hydrocarbon group, an aromatic group or a heterocyclic group.

Preferably, R₁ is selected from benzoyl and t-butyloxycarbonyl;
R₂ is selected from phenyl;
R₃ is selected from —OMe.

Most preferably, the taxanes compounds of the present invention are selected from the compounds having the following structures:

| Compound | MW | Formula | Structure |
|---|---|---|---|
| PCMI-22 | 892 | C₄₇H₆₀N₂O₁₅ | 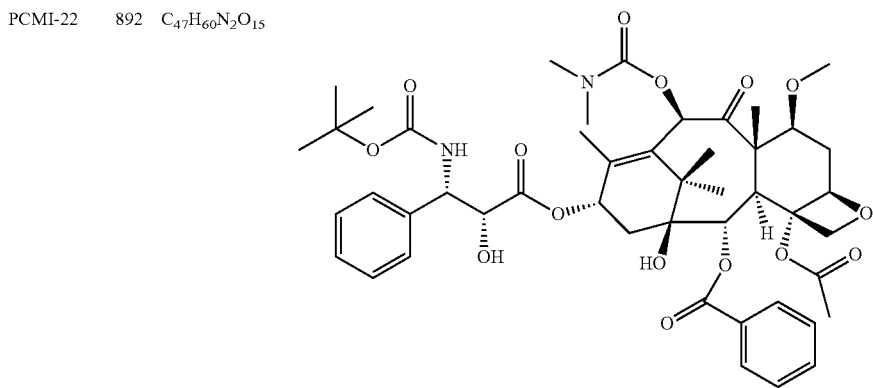 |
| PCMI-23 | 896 | C₄₉H₅₆N₂O₁₄ | 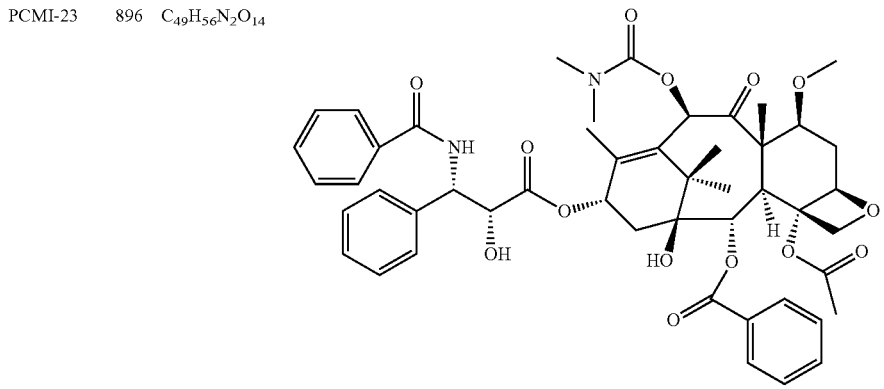 |

-continued

| Compound | MW | Formula | Structure |
|---|---|---|---|
| PCMI-24 | 893 | $C_{46}H_{59}N_3O_{15}$ | 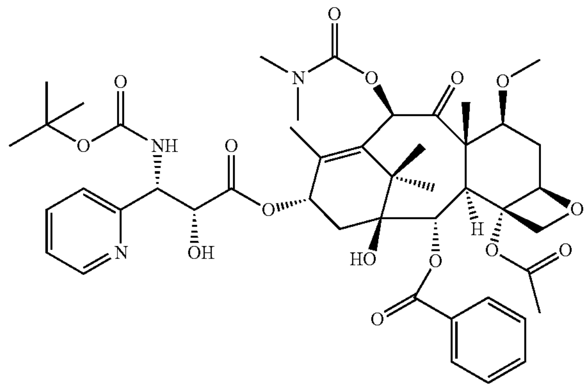 |
| PCMI-25 | 872 | $C_{45}H_{64}N_2O_{15}$ | 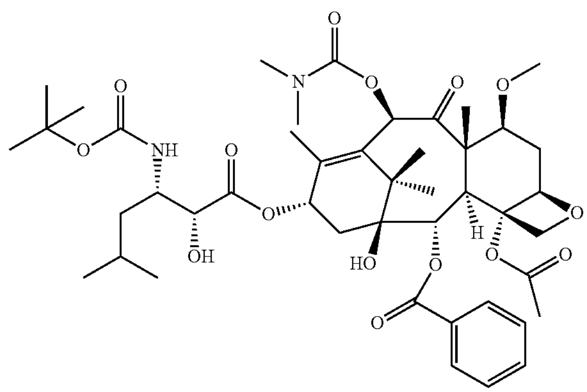 |
| PCMI-26 | 879 | $C_{46}H_{57}NO_{16}$ | 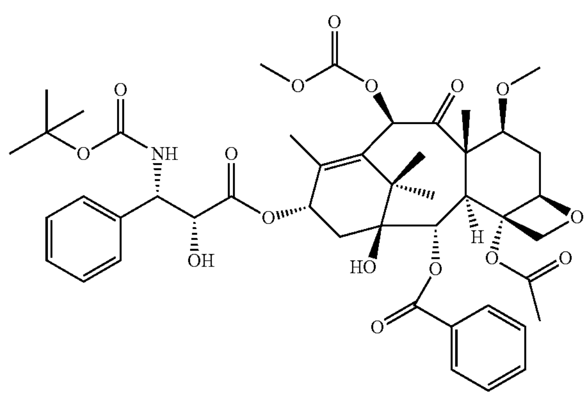 |
| PCMI-27 | 883 | $C_{48}H_{53}NO_{15}$ | 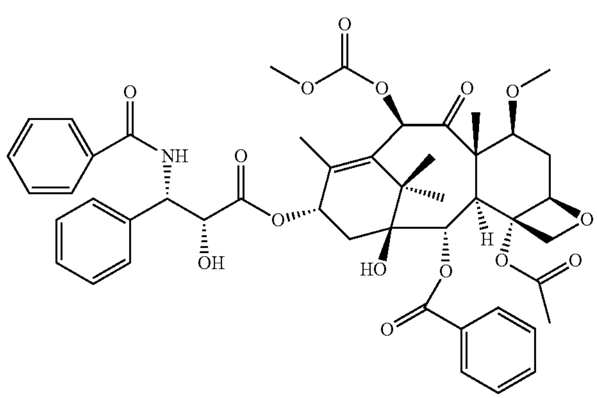 |

-continued
| Compound | MW | Formula | Structure |
|---|---|---|---|
| PCMI-28 | 859 | $C_{44}H_{61}NO_{16}$ | 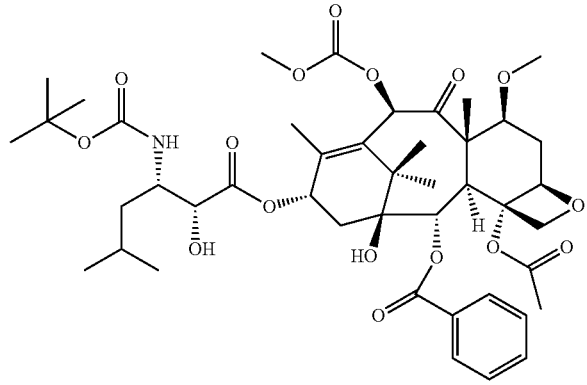 |
| PCMI-29 | 850 | $C_{44}H_{54}N_2O_{15}$ | 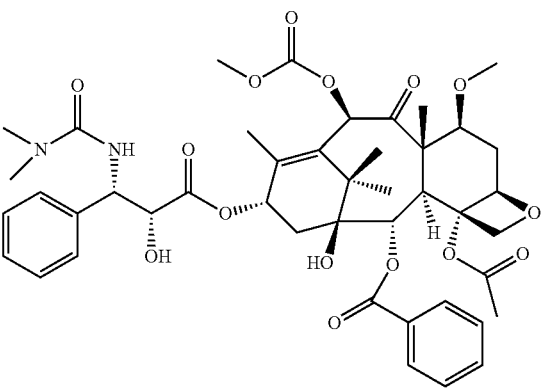 |
| PCMI-30 | 909 | $C_{47}H_{59}NO_{15}S$ | 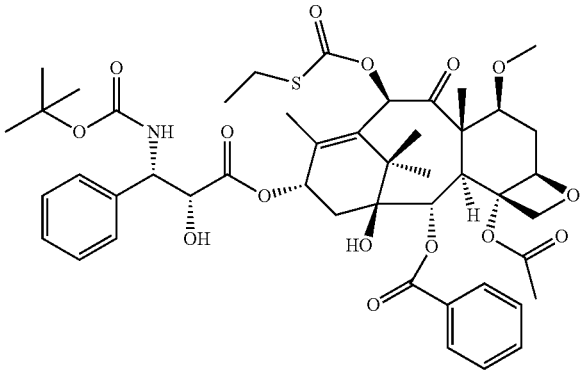 |
| PCMI-31 | 892 | $C_{47}H_{60}N_2O_{15}$ | 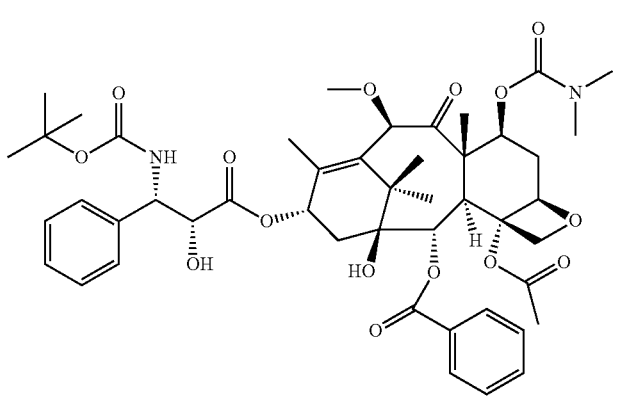 |

-continued
| Compound | MW | Formula | Structure |
|---|---|---|---|
| PCMI-32 | 896 | $C_{49}H_{56}N_2O_{14}$ | 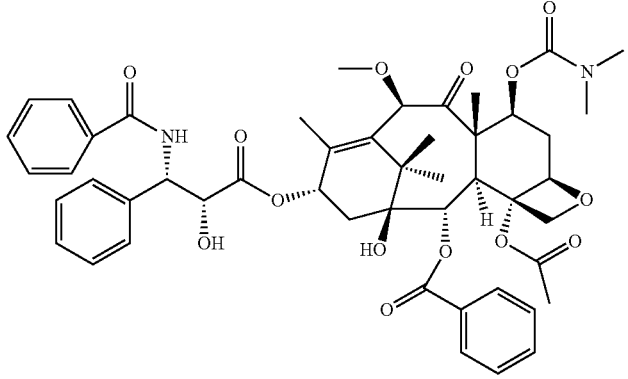 |
| PCMI-33 | 893 | $C_{46}H_{59}N_3O_{15}$ | 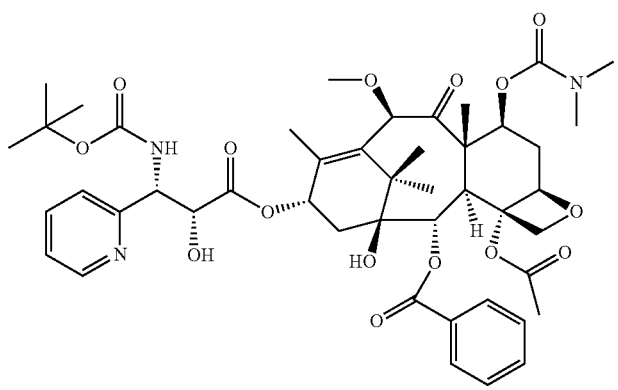 |
| PCMI-34 | 872 | $C_{45}H_{64}N_2O_{15}$ | 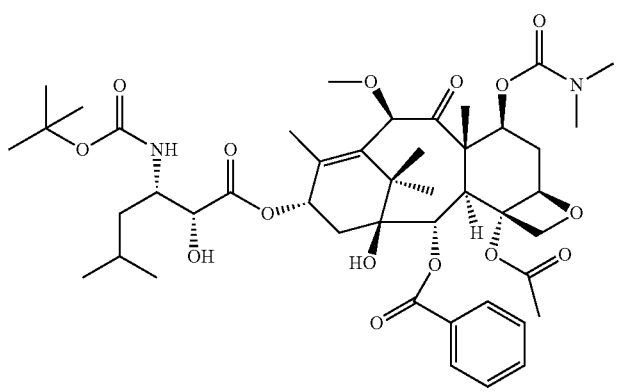 |
| PCMI-35 | 863 | $C_{45}H_{57}N_3O_{14}$ | 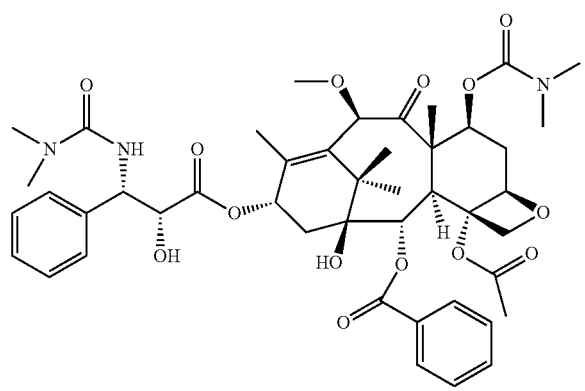 |

-continued

| Compound | MW | Formula | Structure |
|---|---|---|---|
| PCMI-36 | 879 | $C_{46}H_{57}NO_{16}$ | 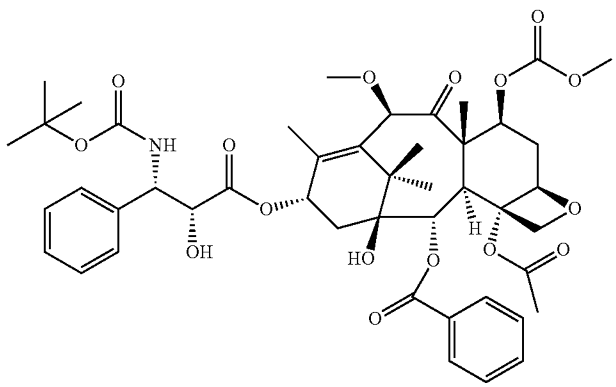 |
| PCMI-37 | 883 | $C_{48}H_{53}NO_{15}$ | 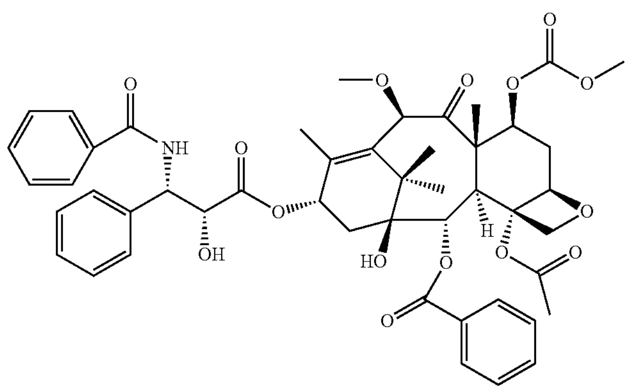 |
| PCMI-38 | 880 | $C_{45}H_{56}N_2O_{16}$ | 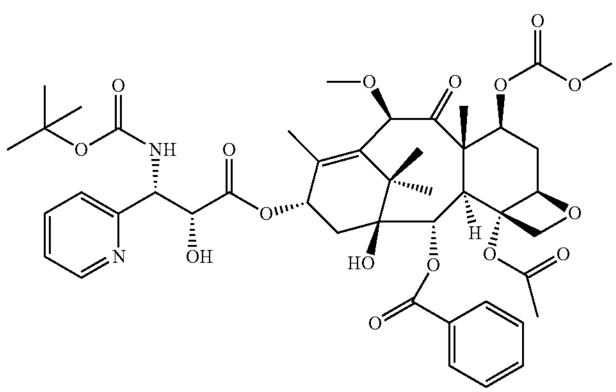 |
| PCMI-39 | 859 | $C_{44}H_{61}NO_{16}$ | 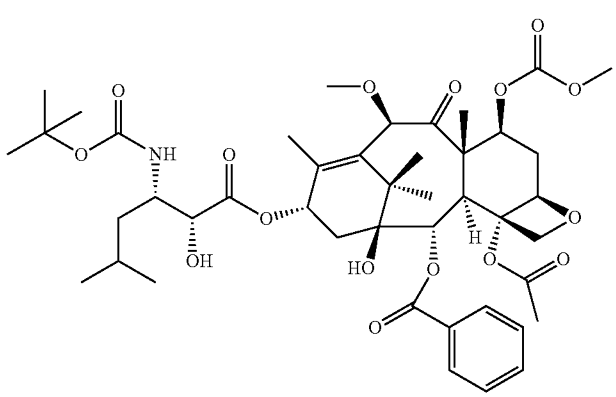 |

-continued

| Compound | MW | Formula | Structure |
| --- | --- | --- | --- |
| PCMI-40 | 880 | $C_{45}H_{56}N_2O_{14}S$ | 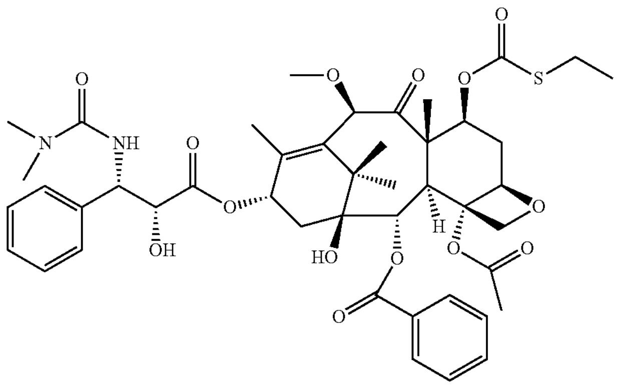 |
| PCMI-41 | 805 | $C_{44}H_{55}NO_{13}$ | 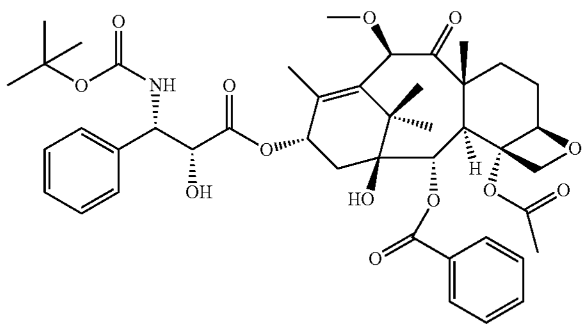 |
| PCMI-42 | 785 | $C_{42}H_{59}NO_{13}$ | 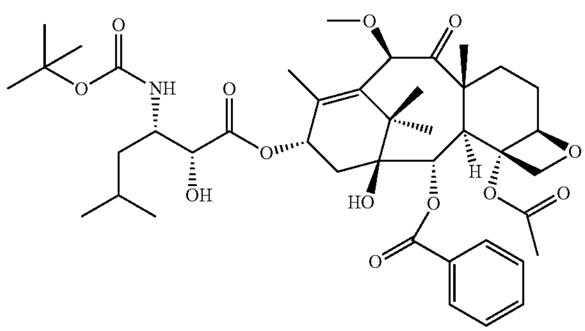 |
| PCMI-43 | 825 | $C_{46}H_{51}NO_{13}$ | 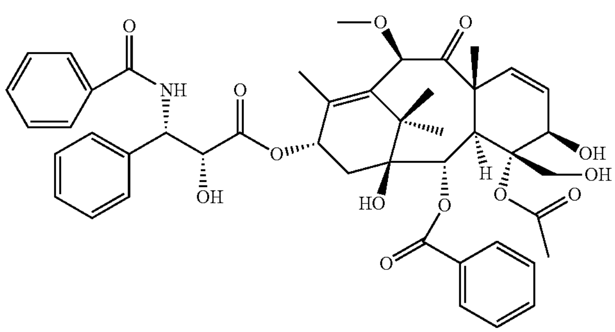 |

-continued

| Compound | MW | Formula | Structure |
|---|---|---|---|
| PCMI-44 | 821 | $C_{44}H_{55}NO_{14}$ | 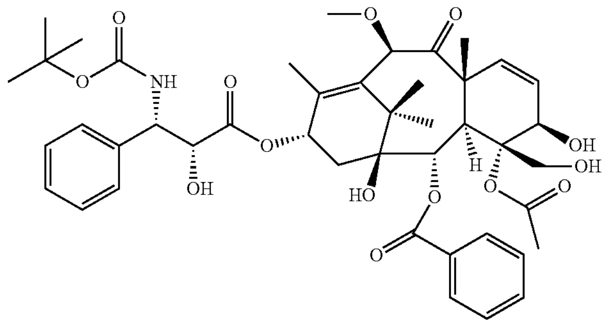 |

According to the present invention, the compounds having the structures represented by the general formula (I) and formula (II) further include all isomers of these compounds and mixtures of the isomers.

If necessary, the compounds having the structures represented by the general formula (I) and formula (II) ma be formed into a pharmaceutically acceptable non-toxic salts.

According to the present invention, the compounds having the structures represented by the general formula (I) and formula (II) may optionally exist in the form of solvates (such as hydrates). Therefore, these solvates (such as hydrates) are also included within the compounds of the present invention.

Furthermore, the present invention provides a pharmaceutical composition comprising the compounds having the structures represented by the above defined general formula (I) and formula (II) may be the pharmaceutically acceptable salts or solvates thereof as active ingredients, as well as and the use thereof in manufacturing oral antitumor medicaments.

In the pharmaceutical composition of the present invention, the weight ratio of the compounds of the present invention is 0.01%-99.99% with the balance of pharmaceutically acceptable carriers. The pharmaceutical composition is in the form of suitable preparations.

The preparations include: tablets, capsules, granules, pills, powders, slurries, suspensions, injections, powder-injections, suppositories, creams, drops or patches. Wherein, the tablets are sugar-coated tablets, film-coated tablets, enteric coated tablets or sustained release tablets: the capsules are hard capsules, soft capsules or sustained release capsules; the powder-injections are lyophilized powder-injections.

In the dosage form of the pharmaceutical composition of the present invention, each dosage form contains an effective amount of 0.1 mg-1000 mg of the compounds of the present invention. Wherein, each dosage form refers to each unit thereof, e.g. each tablet in tablets, each capsule in capsules. Alternatively, it can also refer to the dose administrated at each time (e.g. a dose of 100 mg at each time).

The solid carriers may be used, when the pharmaceutical composition of the present invention is prepared into solid or semi-solid preparations such as powders, tablets, dispersible powders, capsules, cachets, suppositories and ointments. The usable solid carrier is preferably selected from one or more substances of diluents, flavors, solubilizers, lubricants, suspending agents, binders, bulking agents and the like, or may be encapsulating materials. In powder preparations, it contains 5-70 wt % of the micronized active ingredient in the carriers. Suitable solid carriers include magnesium carbonate, magnesium stearate, talc powder, sucrose, lactose, pectin, dextrin, starch, gelatin, methyl cellulose, sodium carboxymethyl cellulose, low boiling point wax, cocoa butter and the like. Since tablets, powders, cachets and capsules are easily to be administrated, they represent the most advantageous oral solid preparations.

The liquid preparations of the present invention include solutions, suspensions and emulsions. For example, the injection preparations for parenteral administration can be in the form of water solution or water-propylene glycol solution, which is used to adjust isotonicity, pH, etc., making it adapted to the physiological conditions of the living body. Alternatively, liquid preparations can be prepared in the form of polyethylene glycol or water solution. The oral water solution can be prepared by dissolving the active ingredients in water and adding appropriate amounts of colorants, flavors, stabilizing agents and thickening agents therein. In addition, the oral water suspensions can be prepared by dispersing the micronized active ingredients into viscous materials, such as natural and synthetic gums, methylcellulose, sodium carboxymethyl cellulose and other known suspending agents.

For convenience of administration and dose uniformity, it is particularly advantageous to prepare the aforementioned pharmaceutical preparations in the form of a preparation unit. The preparation unit refers to a physically separable unit containing a single dose. Each unit contains a well-calculated predetermined amount of active ingredients, which can produce desired therapeutic effects. This preparation unit may be in the packaged form, for example tablets, capsules, powders in small tubes or bottles, or ointments, gels or creams in tubes or bottles.

Although the amount of active ingredient in the preparation unit can be varied, it is generally in a range of 1-1000 mg based on the efficacy of the selected active ingredient.

When the compounds of the present invention represented by the formula (I) and formula (II) are used as antitumor agents, their dose may be varied depending on the needs of patients, conditions of the disease, the selected compounds and the like.

According to the present invention, the taxanes compounds are prepared by a method comprising the following steps:

Step 1 synthesis of a precursor of five-member ring oxazolidine acid side chain: the precursor of five-member ring oxazolidine acid side chain is prepared by a series of reactions including introduction of protective groups, addition condensation, acid hydrolysis, aldol condensation, catalytic hydrogenation and the like;

Step 2 synthesis of taxanes mother nucleus part: by using 10-deacetyl baccatin III (10-DAB) as raw material, the hydroxyl groups at C7 and C10 positions of the mother nucleus part are selectively modified on the basis of different activities thereof, to give taxanes mother nucleus part;

Step 3 synthesis of taxanes derivatives: the precursor of five-member ring oxazolidine acid side chain is linked with the taxanes mother nucleus part by esterification and a series of taxanes derivatives are generated after removal of the protective group by acid hydrolysis.

Preferably, the preparation method of the present invention comprises the following steps:

Step 1 synthesis of the precursor of five-member ring oxazolidine acid side chain: glycolic acid, used as raw material, is protected successively by benzyl group and t-butyloxycarbonyl group (Boc group) to generate the Boc-protected benzyl glycolate; different substituted aldehydes are condensed with $(S_R)$-t-butyl sulfinamide to form the corresponding enamine compounds. The Boc-protected benzyl glycolate and the enamine compound are reacted via an addition reaction in the presence of lithium salt, and then a chiral intermediate is given after acid hydrolysis, and the obtained intermediate is reacted with 1,1'-(dimethoxymethyl) p-methoxybenzene via an aldol condensation reaction, catalyzed by pyridinium p-toluenesulfonate (PPTS) to obtain a condensation compound. The amino group of the condensation compound is substituted with different substituents, and the precursor of five-member ring oxazolidine acid side chain is finally given after catalytic hydrogenation. The reaction route is as follows:

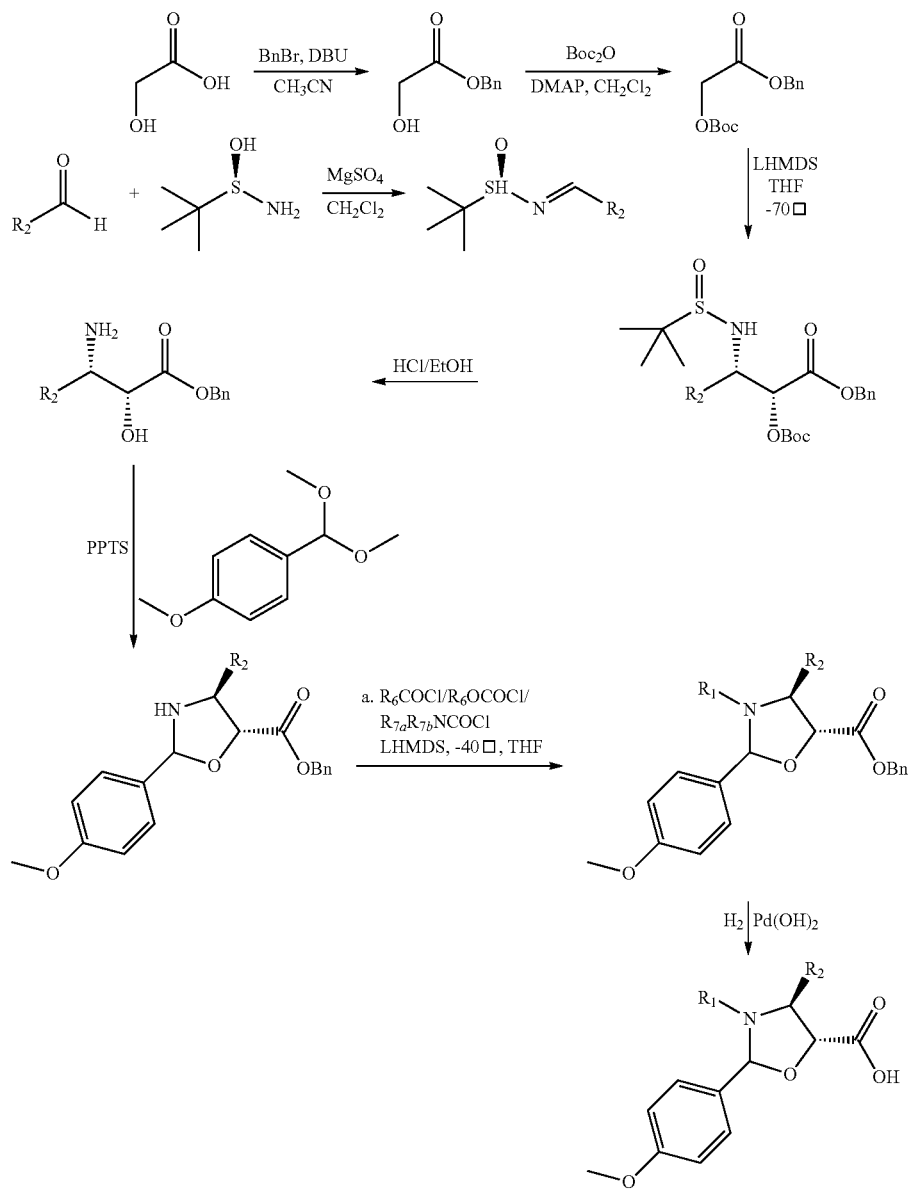

Step 2 synthesis of taxanes mother nucleus part: 10-deacetyl baccatin III is used as raw material, C7-hydroxyl group is firstly protected with a silyl group, and C10-hydroxyl group is selectively protected with substituents. After introducing a protective group at C10 position, the protective group of the hydroxy group at C7 position is removed and then the hydroxy group at C7 position is substituted with selected substitutents to give the taxanes mother nucleus part.

Step 3 synthesis of taxanes derivatives: the precursor of five-member ring oxazolidine acid side chain is linked with the taxanes mother nucleus part by esterification and the obtained compound is subjected to acid hydrolysis to remove the protective group on side chain to give the taxanes derivatives.

Wherein, in Step 1, the different substituted aldehydes include: C1-C6 hydrocarbyl aldehydes, C1-C6 substituted hydrocarbyl aldehydes, aromatic aldehydes, substituted aromatic aldehydes and heteroaromatic aldehydes;

In Step 1, the involved reaction in which the amino group of the condensation compound is substituted with corresponding acyl chloride under the following conditions: alkaline conditions: tetrahydrofuran, dichloromethane or dioxane used as the solvent and the temperature from room temperature to −70° C.;

In Step 1, palladium-charcoal or palladium hydroxide is used as the catalyst in the catalytic hydrogenation reaction; hydrogen is induced at normal pressure or pressurized conditions in alcohols, tetrahydrofuran or dichloromethane and the like as the solvent.

In Step 2, the C7- and C10-hydroxyl groups are protected with substituents:

(1) When $R_3$ and $R_4$ are —$OR_6$, the reaction involved is: firstly, the hydroxyl group is reacted with p-toluenesulfonyl chloride (TsCl) at room temperature to 0° C. in tetrahydrofuran or dichloromethane as the solvent and pyridine (Py) is used as the alkali, to give p-toluenesulfonate (C7/10-OTs), which is further reacted with a Grignard reagent to give the corresponding ether —$OR_6$;

(2) When $R_3$ and $R_4$ are —$OCOOR_6$ or —$OCONR_{7a}R_{7b}$, the reaction involved is: under alkaline conditions, the hydroxyl group is reacted with the corresponding acyl chloride in tetrahydrofuran as the solvent at room temperature to −70° C.;

(3) When $R_3$ and $R_4$ are —$OCOSR_6$, the reaction involved is: the hydroxyl group is reacted with N,N'-carbonyldiimidazole (CDI) in tetrahydrofuran as the solvent at room temperature, and the obtained product is further reacted with mercaptan via substitution reaction;

(4) When $R_4$ is hydrogen, the reaction involved is: C7-hydroxyl group is reacted with a solution of N,N'-thiocarbonyldiimidazole (TCDI) in tetrahydrofuran at room temperature to give xanthate; and the obtained xanthate is subjected to Barton de-oxygen free radical reaction in a mixed solution of dioxane/tetrahydrofuran at 80-100° C., preferably 85° C., catalyzed by azobisisobutyronitrile (AIBN) under the action of n-butyl tin hydride ($Bu_3SnH$);

(5) When a double bond is formed between C6 and C7 positions (i.e., the compounds of the general formula II), the reaction involved is: C7-hydroxyl group is reacted with trifluoromethanesulfonic anhydride ($Tf_2O$) in a dichloromethane solution to give sulfonate C7-OTf by using pyridine as an alkali; and the sulfonate C7-OTf is subjected to an elimination reaction at 100° C. in a mixed solution of dioxane/tetrahydrofuran under the action of 1,8-diazabicyclo[5.4.0]undec-7-ene (DBU), to form the double bond between C6 and C7 positions.

Preferably,

In Step 1, in the reaction involved in the substitution of the amino group of the condensation compound, lithium hexamethyldisilazide (LHMDS) is preferably used as the alkali and tetrahydrofuran is used as the solvent; the temperature is preferably at −40° C., the acyl chloride includes $R_6COCl$, $R_6OCOCl$ and $R_{7a}R_{7b}NCOCl$; In the catalytic hydrogenation reaction, palladium hydroxide is preferably used as the catalyst, hydrogen is introduced at 20 psi and the reaction is preferably carried out in an alcoholic solution; In Step 2, the C7- and C10-hydroxyl groups are protected by substituents:

(1) When $R_3$ and $R_4$ are —$OR_6$, dichloromethane is preferably selected as the solvent, the temperature is preferably at 0° C. and the Grignard reagent includes $R_6MgBr$;

(2) When $R_3$ and $R_4$ are —$OCOOR_6$ or —$OCONR_{7a}R_{7b}$, lithium hexamethyldisilazide is preferably selected as the alkali and the temperature is preferably at −40° C.; the acyl chloride includes $R_6OCOCl$ and $R_{7a}R_{7b}NCOCl$;

(3) When $R_3$ and $R_4$ are —$OCOSR_6$, the mercaptan includes $R_6SH$.

The taxanes compounds of the present invention have oral antitumor activity and the beneficial effects of the present invention are illustrated below by experimental data.

1. Cytotoxicity Assay Using Human Tumor Cell Lines

Paclitaxel was used as the positive drug. MTT assay was used to investigate the proliferation inhibition rate of taxanes derivatives of the present invention on 16 cancer cell lines (including MCF-7, MDA-MB-436 breast cancer cells; A549, NCI-H460 non-small cell lung cancer: A2780 ovarian cancer: A375, B16 melanoma: HCT 116, HT-29 colon cancer; Hela cervical cancer: HL-60, K562 leukemia; LNCaP. Du145 prostate cancer; LN-18, BGC-823 gastric cancer) at a concentration of 1 μM and the experimental results are shown in Table 1.

TABLE 1

Proliferation inhibition rate of the taxanes compounds of the present invention on 16 cancer cell lines

| | Proliferation inhibition rate at a concentration of 1 μM | | | | | | | |
|---|---|---|---|---|---|---|---|---|
| Compounds | A2780 Ovarian cancer | HeLa Cervical cancer | MCF-7 Breast cancer | NCI-H460 Non-small cell lung cancer | A375 Melanoma | HT29 Colon cancer | HL60 Leukemia | DU145 Prostate cancer |
| Paclitaxel | 96.68 | 101.04 | 94.20 | 87.48 | 96.22 | 88.36 | 96.80 | 90.62 |
| PCMI-22 | 96.31 | 101.83 | 85.73 | 86.54 | 87.65 | 87.89 | 97.45 | 87.14 |
| PCMI-23 | 94.82 | 99.76 | 93.49 | 83.31 | 87.71 | 87.92 | 97.21 | 84.79 |
| PCMI-24 | 95.53 | 100.30 | 82.35 | 83.56 | 86.80 | 88.10 | 98.11 | 84.69 |
| PCMI-25 | 94.82 | 100.56 | 89.78 | 80.65 | 89.00 | 87.29 | 97.66 | 82.89 |
| PCMI-26 | 95.80 | 100.93 | 95.47 | 86.44 | 94.18 | 88.75 | 96.84 | 86.20 |
| PCMI-27 | 94.13 | 99.53 | 95.28 | 80.43 | 102.87 | 87.32 | 97.40 | 83.30 |
| PCMI-28 | 95.60 | 99.65 | 102.90 | 85.75 | 91.86 | 89.09 | 96.94 | 85.74 |

TABLE 1-continued

Proliferation inhibition rate of the taxanes compounds of the present invention on 16 cancer cell lines

| PCMI-29 | 92.50 | 97.27 | 91.28 | 85.19 | 92.85 | 81.67 | 96.85 | 86.73 |
|---|---|---|---|---|---|---|---|---|
| PCMI-30 | 95.63 | 101.39 | 95.77 | 85.82 | 96.93 | 87.81 | 98.52 | 90.26 |
| PCMI-31 | 95.57 | 102.82 | 90.79 | 87.68 | 88.42 | 89.36 | 97.82 | 85.80 |
| PCMI-32 | 95.81 | 102.87 | 102.13 | 86.59 | 90.43 | 89.81 | 97.77 | 87.45 |
| PCMI-33 | 94.69 | 102.64 | 83.46 | 87.75 | 90.34 | 89.11 | 97.75 | 86.30 |
| PCMI-34 | 95.01 | 102.32 | 101.21 | 86.19 | 104.50 | 89.15 | 98.09 | 86.86 |
| PCMI-35 | 94.23 | 99.88 | 92.45 | 86.94 | 95.31 | 87.26 | 97.45 | 89.78 |
| PCMI-36 | 96.88 | 102.11 | 106.85 | 90.32 | 93.96 | 89.73 | 97.79 | 88.35 |
| PCMI-37 | 96.42 | 101.56 | 102.71 | 89.49 | 97.39 | 89.65 | 97.01 | 88.52 |
| PCMI-38 | 96.55 | 101.75 | 106.08 | 88.69 | 88.34 | 89.76 | 97.44 | 89.18 |
| PCMI-39 | 94.87 | 99.99 | 99.96 | 81.60 | 90.21 | 88.41 | 99.11 | 84.92 |
| PCMI-40 | 94.24 | 99.56 | 94.65 | 87.35 | 95.16 | 87.23 | 96.89 | 89.97 |
| PCMI-41 | 95.79 | 101.12 | 95.52 | 85.74 | 91.64 | 88.28 | 97.65 | 87.62 |
| PCMI-42 | 95.63 | 99.31 | 97.84 | 84.31 | 104.36 | 88.18 | 97.58 | 87.04 |
| PCMI-43 | 69.98 | 52.05 | 68.33 | 62.12 | 77.83 | 36.37 | 76.30 | 63.40 |
| PCMI-44 | 95.64 | 99.27 | 95.17 | 85.15 | 93.92 | 88.32 | 96.30 | 89.23 |

Proliferation inhibition rate at a concentration of 1 μM

| Compounds | MDA-MB-436 Breast cancer | LN-18 Gastric cancer | BGC-823 Gastric cancer | A549 Non-small cell lung cancer | B16 Melanoma | HCT 116 Colon cancer | K562 Leukemia | LNCaP Prostate cancer |
|---|---|---|---|---|---|---|---|---|
| Paclitaxel | 83.09 | 94.49 | 92.52 | 81.59 | 84.05 | 70.36 | 96.62 | 87.10 |
| PCMI-22 | 81.08 | 95.54 | 91.96 | 69.88 | 74.69 | 81.12 | 92.16 | 80.88 |
| PCMI-23 | 84.77 | 96.30 | 94.55 | 77.78 | 80.83 | 78.31 | 93.83 | 81.79 |
| PCMI-24 | 76.29 | 94.05 | 93.49 | 73.75 | 78.94 | 81.12 | 92.20 | 81.09 |
| PCMI-25 | 78.44 | 92.45 | 90.22 | 69.47 | 71.78 | 78.31 | 90.94 | 80.42 |
| PCMI-26 | 76.30 | 88.99 | 89.21 | 66.16 | 69.66 | 81.12 | 91.39 | 79.84 |
| PCMI-27 | 83.30 | 96.33 | 94.07 | 74.84 | 79.24 | 78.31 | 94.55 | 82.64 |
| PCMI-28 | 84.30 | 97.50 | 92.19 | 72.53 | 74.08 | 81.12 | 92.62 | 84.02 |
| PCMI-29 | 75.68 | 97.69 | 90.81 | 78.13 | 80.64 | 68.70 | 90.79 | 84.32 |
| PCMI-30 | 81.34 | 94.98 | 94.88 | 75.80 | 81.71 | 65.46 | 92.60 | 86.16 |
| PCMI-31 | 86.35 | 95.64 | 96.17 | 76.05 | 81.82 | 60.71 | 93.20 | 82.19 |
| PCMI-32 | 74.36 | 92.20 | 95.12 | 74.47 | 77.79 | 57.68 | 90.99 | 83.39 |
| PCMI-33 | 76.18 | 93.20 | 94.06 | 74.11 | 81.78 | 55.99 | 91.10 | 83.58 |
| PCMI-34 | 81.20 | 90.57 | 94.74 | 73.55 | 81.39 | 60.08 | 92.94 | 88.65 |
| PCMI-35 | 80.24 | 93.45 | 95.78 | 76.18 | 80.33 | 65.45 | 92.69 | 85.32 |
| PCMI-36 | 77.45 | 95.86 | 94.60 | 77.96 | 81.75 | 67.18 | 94.52 | 83.77 |
| PCMI-37 | 86.13 | 98.31 | 95.71 | 79.95 | 85.28 | 67.36 | 94.55 | 85.53 |
| PCMI-38 | 85.92 | 96.56 | 95.68 | 80.29 | 83.32 | 64.05 | 94.65 | 82.43 |
| PCMI-39 | 78.40 | 94.08 | 91.73 | 67.38 | 72.33 | 57.09 | 92.15 | 82.85 |
| PCMI-40 | 83.58 | 93.87 | 93.27 | 80.24 | 83.65 | 67.28 | 92.68 | 87.25 |
| PCMI-41 | 80.12 | 94.64 | 93.11 | 76.99 | 81.12 | 64.95 | 94.28 | 82.46 |
| PCMI-42 | 79.53 | 94.78 | 92.84 | 77.58 | 78.31 | 66.06 | 94.35 | 82.89 |
| PCMI-43 | 35.68 | 73.19 | 38.25 | 53.87 | 13.26 | 46.12 | 80.88 | 61.21 |
| PCMI-44 | 82.71 | 89.81 | 90.75 | 75.89 | 75.31 | 67.14 | 94.41 | 86.90 |

Preliminary activity evaluation indicates that a vast majority of taxanes derivatives show similar or stronger cytotoxicity on most cancer cell lines than that of the positive control drug. In both cancer cell lines of A549 and B16, the cytotoxicity of the taxanes derivatives is slightly lower than that of the positive control drug. The cytotoxicity of PCMI-43 is weakened, while the PCMI-44 remains good cytotoxicity, indicating that with ring-opening of D-ring of the paclitaxel mother nucleus part, its cytotoxicity do not necessarily disappear, and the cytotoxicity is also related to the functional groups on side chains. Experimental results show that the taxanes derivatives of the present invention have excellent tumor inhibiting activity.

From the activity evaluation data of the above-mentioned preliminary screen, it can be seen that the series of taxanes derivatives synthesized in the present invention have activity (although the activity of PCMI-43 is weakened). Afterward, most of the compounds are picked up from these derivatives to examine their $IC_{50}$ values on breast cancer cell line MCF-7. Paclitaxel is used as the positive control drug. Experiments for each compound were independently repeated for three times and multiple holes were used in each experiment. The exposure time of drugs was 72 hours. The median lethal dose ($IC_{50}$) is expressed as mean±SD and the experimental data are shown in Table 2.

TABLE 2

$IC_{50}$ values of the taxanes compounds of the present invention on breast cancer cell line MCF-7

| Compounds | MCF-7($IC_{50}$, nM) |
|---|---|
| Paclitaxel | 7.05 ± 0.12 |
| PCMI-22 | 1.58 ± 0.04 |
| PCMI-25 | 1.70 ± 0.08 |
| PCMI-26 | 1.40 ± 0.10 |
| PCMI-28 | 2.90 ± 0.06 |
| PCMI-31 | 9.63 ± 0.12 |
| PCMI-32 | 64.67 ± 0.18 |
| PCMI-33 | 46.63 ± 0.14 |
| PCMI-34 | 13.26 ± 0.12 |
| PCMI-35 | 4.28 ± 0.08 |
| PCMI-36 | 4.97 ± 0.06 |
| PCMI-39 | 2.81 ± 0.02 |

TABLE 2-continued

IC$_{50}$ values of the taxanes compounds of the present invention on breast cancer cell line MCF-7

| Compounds | MCF-7(IC$_{50}$, nM) |
|---|---|
| PCMI-40 | 5.49 ± 0.14 |
| PCMI-41 | 3.33 ± 0.11 |
| PCMI-42 | 3.06 ± 0.08 |
| PCMI-44 | 10.91 ± 0.16 |

As shown from the data of Table 2, the IC$_{50}$ value of the positive control drug paclitaxel is about 7.05 nM. When the side chain structures of the series of taxanes derivatives of the present invention are $R_1$=—COOR$_6$ or —CONR$_{7a}$R$_{7b}$, $R_2$=phenyl, or alkyl chain, the IC$_{50}$ values thereof are quite equal to that of paclitaxel, maintaining at about the same order of magnitude. While IC$_{50}$ values of some derivatives are better than that of paclitaxel. Thus, it can be seen that in vitro activity of most of the derivatives of the present invention remain unchanged or even be improved as compared with paclitaxel. Some of the compounds have slightly lower activity than that of the positive control drug paclitaxel.

2. Caco-2 Cell Monolayer Membrane Transport Assay

Human-derived colorectal adenocarcinoma cell line Caco-2 cell monolayer model was used to study the bidirectional transport of the target compounds from the apical (AP) side to the basolateral (BL) side and from BL side to AP side. HPLC was used for quantitative analysis to calculate transport parameters, apparent permeability coefficient (Papp) and the efflux ratio. Paclitaxel was used as the positive control drug and the P-gp substrates erythromycin was used as a reference to predict the oral bioavailability in vive of these taxanes derivatives and affinity thereof with P-gp.

TABLE 3

A-to-B Papp of the taxanes derivatives of the present invention in Caco-2 cell model

| Compounds | | Papp × 10$^{-6}$ cm/sec | | | |
|---|---|---|---|---|---|
| | | Sample-01 | Sample-02 | Mean | SD |
| Erythromycin | A-B | 0.80 | 0.63 | 0.71 | 0.16 |
| | B-A | 7.15 | 7.04 | 7.09 | 0.01 |
| Metoprolol | A-B | 28.09 | 26.25 | 27.17 | 0.05 |
| | B-A | 22.44 | 22.96 | 22.70 | 0.02 |
| Atenolol | A-B | 1.07 | 0.67 | 0.87 | 0.32 |
| | B-A | 0.50 | 0.55 | 0.53 | 0.06 |
| Paclitaxel | A-B | 1.02 | 0.93 | 0.97 | 0.07 |
| PCMI-22 | A-B | 9.00 | 8.38 | 8.69 | 0.05 |
| PCMI-23 | A-B | 3.21 | 2.68 | 2.94 | 0.13 |
| PCMI-24 | A-B | 2.93 | 3.10 | 3.02 | 0.04 |
| PCMI-25 | A-B | 6.41 | 9.92 | 8.17 | 0.30 |
| PCMI-26 | A-B | 8.45 | 9.06 | 8.75 | 0.05 |
| PCMI-27 | A-B | 4.44 | 4.31 | 4.38 | 0.02 |
| PCMI-28 | A-B | 8.58 | 9.46 | 9.02 | 0.07 |
| PCMI-29 | A-B | 9.53 | 7.33 | 8.43 | 0.18 |
| PCMI-30 | A-B | 5.78 | 3.59 | 4.68 | 0.33 |
| PCMI-31 | A-B | 11.19 | 9.91 | 10.55 | 0.09 |
| PCMI-32 | A-B | 3.16 | 3.38 | 3.27 | 0.05 |
| PCMI-33 | A-B | 4.27 | 4.54 | 4.41 | 0.04 |
| PCMI-34 | A-B | 11.82 | 9.54 | 10.68 | 0.15 |
| PCMI-35 | A-B | 3.21 | 2.87 | 3.04 | 0.24 |
| PCMI-36 | A-B | 6.66 | 7.29 | 6.97 | 0.06 |
| PCMI-37 | A-B | 3.23 | 3.41 | 3.32 | 0.04 |
| PCMI-38 | A-B | 4.71 | 4.35 | 4.53 | 0.06 |
| PCMI-39 | A-B | 6.13 | 8.81 | 7.47 | 0.25 |
| PCMI-40 | A-B | 3.78 | 4.05 | 3.92 | 0.19 |
| PCMI-41 | A-B | 4.27 | 5.79 | 5.03 | 0.21 |
| PCMI-42 | A-B | 7.85 | 6.49 | 7.17 | 0.13 |
| PCMI-43 | A-B | 3.21 | 2.89 | 3.05 | 0.07 |
| PCMI-44 | A-B | 5.28 | 6.39 | 5.83 | 0.14 |

TABLE 4

Trans-membrane recovery rate in mass of the taxanes derivatives of the present invention in Caco-2 cell model

| Compounds | | Recovery rate in mass (%) | | | |
|---|---|---|---|---|---|
| | | Sample-01 | Sample-02 | Mean | SD |
| Erythromycin | A-B | 99.58 | 98.51 | 99.04 | 0.01 |
| Metoprolol | A-B | 102.51 | 95.49 | 99.00 | 0.05 |
| Atenolol | A-B | 93.89 | 96.29 | 95.09 | 0.02 |
| Paclitaxel | A-B | 94.61 | 107.07 | 100.84 | 0.09 |
| PCMI-22 | A-B | 92.42 | 86.38 | 89.40 | 0.05 |
| PCMI-23 | A-B | 100.34 | 73.95 | 87.14 | 0.21 |
| PCMI-24 | A-B | 106.22 | 94.77 | 100.49 | 0.08 |
| PCMI-25 | A-B | 63.93 | 78.50 | 71.21 | 0.14 |
| PCMI-26 | A-B | 80.90 | 81.98 | 81.44 | 0.01 |
| PCMI-27 | A-B | 99.28 | 91.90 | 95.59 | 0.05 |
| PCMI-28 | A-B | 64.85 | 76.85 | 70.85 | 0.12 |
| PCMI-29 | A-B | 101.83 | 97.05 | 99.44 | 0.03 |
| PCMI-30 | A-B | 70.43 | 82.62 | 76.53 | 0.11 |
| PCMI-31 | A-B | 83.00 | 90.63 | 86.82 | 0.06 |
| PCMI-32 | A-B | 82.10 | 81.62 | 81.86 | 0.00 |
| PCMI-33 | A-B | 95.78 | 94.05 | 94.92 | 0.01 |
| PCMI-34 | A-B | 71.25 | 63.63 | 67.44 | 0.08 |
| PCMI-35 | A-B | 95.04 | 87.58 | 91.31 | 0.06 |
| PCMI-36 | A-B | 95.54 | 81.37 | 88.46 | 0.11 |
| PCMI-37 | A-B | 81.25 | 80.03 | 80.64 | 0.01 |
| PCMI-38 | A-B | 121.96 | 119.89 | 120.92 | 0.01 |
| PCMI-39 | A-B | 71.74 | 56.70 | 64.22 | 0.17 |
| PCMI-40 | A-B | 78.23 | 70.69 | 74.46 | 0.07 |
| PCMI-41 | A-B | 97.04 | 104.90 | 100.97 | 0.06 |
| PCMI-42 | A-B | 81.01 | 67.32 | 74.17 | 0.13 |
| PCMI-43 | A-B | 76.56 | 67.49 | 72.03 | 0.09 |
| PCMI-44 | A-B | 85.70 | 105.98 | 95.84 | 0.15 |

TABLE 5

Efflux ratio of the representative taxanes derivatives of the present invention in Caco-2 cell model

| | Caco-2 cell line (21 days) | | | | |
|---|---|---|---|---|---|
| | Papp (10$^{-6}$ cm/s) | | | | Efflux |
| Compounds | A-B | SD | B-A | SD | ratio $^a$ |
| Erythromycin | 0.58 | 0.08 | 9.89 | 0.04 | 16.92 |
| Paclitaxel | 0.97 | 0.07 | 33.39 | 0.01 | 34.38 |
| PCMI-34 | 19.43 | 0.28 | 30.93 | 0.13 | 1.59 |
| PCMI-31 | 15.04 | 0.09 | 25.99 | 0.11 | 1.73 |
| PCMI-28 | 8.87 | 0.06 | 33.26 | 0.12 | 3.75 |
| PCMI-25 | 8.25 | 0.14 | 32.58 | 0.06 | 3.95 |
| PCMI-22 | 8.11 | 0.10 | 33.11 | 0.02 | 4.08 |
| PCMI-26 | 6.91 | 0.02 | 29.18 | 0.08 | 4.22 |
| PCMI-44 | 5.72 | 0.15 | 27.21 | 0.07 | 4.76 |

TABLE 5-continued

Efflux ratio of the representative taxanes derivatives of the present invention in Caco-2 cell model

| Compounds | Caco-2 cell line (21 days) | | | | Efflux ratio [a] |
|---|---|---|---|---|---|
| | Papp (10$^{-6}$ cm/s) | | | | |
| | A-B | SD | B-A | SD | |
| PCMI-39 | 7.16 | 0.16 | 36.37 | 0.22 | 5.08 |
| PCMI-42 | 7.54 | 0.08 | 38.57 | 0.32 | 5.12 |
| PCMI-40 | 6.92 | 0.25 | 37.16 | 0.10 | 5.36 |

[a] Efflux ratio = Papp B-A/Papp A-B

The experimental results are shown in Table 3. It can be seen that the A-to-B Papp values of these taxanes derivatives of the present invention are higher than that of paclitaxel (Papp A-to-B=0.97), particularly for PCMI-34 and PCMI-31 derivatives, the Papp A-to-B values thereof >10×10$^{-6}$ cm/s, which belong to highly permeable substrates. These data indicate that these taxanes derivatives have good trans-membrane capacity, thus they are predicted to be better absorbed in vivo than paclitaxel.

The trans-membrane recovery rates of these taxanes derivatives are shown in Table 4. Bidirectional transports of 10 compounds selected from the 23 taxanes derivatives are evaluated and the results are shown in Table 5. It can be seen from the efflux ratios that, as compared with paclitaxel, efflux ratios of these derivatives are reduced in a large degree, which are far less than that of paclitaxel (whose efflux ratio=34.38). Accordingly, the oral absorption in vivo is predicted to be improved.

3. In Vivo Oral Bioavailability Assay

Materials

The compound PCMI-31 was synthesized and detected according to the methods provided in the present invention. The internal standard, paclitaxel, was purchased from China's National Institute for the Control of Pharmaceutical and Biological Products (NICPBP). Chromatography-grade acetonitrile was purchased from Sigma-Aldrich Inc. Tween 80 and ethyl acetate were purchased from Aladdin reagent Inc. Male S.D. rats were purchased from Beijing Weitonglihua Inc. and raised in animal house for two weeks.

Apparatus

Agilent 1100 series HPLC, Agilent G1313A Autosampler, Thermo Finnigan TSQ quadrupole mass spectrometer (San Jose, Calif. USA), Xcallbur® (version 1.3) software (Thermo Finnigan) data analysis software.

Experimental Procedure:

200 mg of PCMI-31 was dissolved in 4 ml of a mixed solution of Tween 80 and anhydrous ethanol (1:1) to prepare a stock solution at 50 mg/ml and normal saline was added to adjust to a suitable concentration. 12 male S.D. rats (about 300 g of body weight) were taken and divided into two groups after overnight fasting. One group was treated with intravenous injection (5 mg/kg) and the other group was treated orally (60 mg/kg). Blood was sampled in the intravenous group at 0$^{th}$ min, 5$^{th}$ min, 10$^{th}$ min, 20$^{th}$ min, 40$^{th}$ min, 1$^{st}$ h, 2$^{nd}$ h, 4$^{th}$ h, 6$^{th}$ h, 8$^{th}$ h, 12$^{th}$ h, 24$^{th}$ h, while the oral group at 5$^{th}$ min, 15$^{th}$ min, 30$^{th}$ min, 45$^{th}$ min, 1$^{st}$ h, 2$^{nd}$ h, 4$^{th}$ h, 6$^{th}$ h, 8$^{th}$ h, 12$^{th}$ h, 24$^{th}$ h. After 10 min centrifugation of plasma at 4500 rpm, the upper serum was taken and transferred to the corresponding EP tube, placed in a −40° C. freezer for assay.

Construction of Standard Curve of PCMI-31

Agilent 1100 series configuration: Agilent G1313A HPLC autosampler device, 150 mm×2.1 mm C18 Thermo column (particle size 3 μm) reversed-phase column, detection wavelength at 230 nm, column temperature at 30° C., mobile phase of acetonitrile/water (7:3), a flow rate at 0.2 ml/min, injection volume of 20 μl. The mass spectrometry (MS) combined was Thermo Finnigan TSQ Quantum triple quadrupole configurated with electrospray ionization (ESI) in the positive ion mode. The parameters of MS analysis were as follows: spray chamber voltage, 4.0 kv; heated capillary temperature, 350° C.; protective gas (nitrogen); 20 psi; auxiliary gas (nitrogen): 5 psi; collision gas (argon); pressure: 1.5 mmTorr.; Collision energy: CA 17 eV; FA and IFA were 19 eV; IS was 15 eV.

Paclitaxel was selected as an internal standard with a retention time of 3.07 min. Retention time of PCMI-31 was 4.21 min. MS detection condition to PCMI-31 was set as follows: 915→634 m/z; paclitaxel as an internal standard. Detection conditions: 876→308m/z. The concentration range of the standard curve of PCMI-31 was 5-10,000 ng/ml ($\gamma^2$>0.99) and the minimum detection limit was 5 ng/ml.

Extraction and analysis of plasma samples

100 μL of plasma samples were taken, into which 100 μL of the internal standard (paclitaxel, 500 ng/ml acetonitrile solution) was added, followed by addition of 3 ml of ethyl acetate after well homogenized via vortex, after 5 min shaking, centrifuging for 8 min at a rotating speed of 4500 rpm. The supernatant was transferred to a clean EP tube with nitrogen to blow to dry under heating condition. After reconstitution with 120 μl mobile phase (CH$_3$CN/H$_2$O=7:3), the solution was centrifuged at 12,000 rpm for 3 min, 100 μl of supernatant was taken and transferred to an autosampler vial. After LC-MS/MS detection, statistical data and pharmacokinetic parameters were processed by Xcallbur® (version 1.3) software (Thermo Finnigan).

Results

Drug concentration-time curve of the compound PCMI-31 by oral or intravenous administration is shown in FIG. 1. Related pharmacokinetic parameters of PCMI-31 are shown in Table 6. The half-life of PCMI-31 is relatively short, generally about 3 h and absolute oral bioavailability (F%) is 10.7%. As compared with the reported absolute oral bioavailability of paclitaxel of less than 5%, the oral bioavailability of PCMI-31 in animals has been improved to a certain extent.

TABLE 6

Relevant pharmacokinetic parameters of PCMI-31 by intravenous and oral administration

| Parameters | Unit | PCMI-31 | |
|---|---|---|---|
| | | Intravenous administration (5 mg/kg) | Oral administration (60 mg/kg) |
| $t_{1/2}$ | h | 3.21 ± 0.53 | 2.97 ± 0.55 |
| $C_{max}$ | ng/ml | 7990.72 ± 3466.17 | 921.51 ± 560.87 |
| $t_{max}$ | h | 0 | 0.8 ± 0.2 |
| $AUC_{0-t}$ | ng · h/ml | 3310.69 ± 1333.34 | 4249.99 ± 2484.31 |
| $AUC_{0-\infty}$ | ng · h/ml | 3318.42 ± 1333.11 | 4265.72 ± 2493.71 |
| $MRT_{0-\infty}$ | h | 2.58 ± 0.87 | 4.33 ± 0.74 |
| F | (%) | | 10.71 |

$AUC_{0-t}$: 0-24 hours area under the curve;
$AUC_{0-\infty}$: area under the curve;
$C_{max}$: peak concentration;
$t_{max}$: peak time;
MRT: mean residence time;
$t_{1/2}$: half-life time;
F: Absolute oral bioavailability, F = (AUC$_{p,o}$ × dose$_{i,v}$)/(AUC$_{i,v}$ × dose$_{p,o}$) × 100%

EXAMPLES

The following examples are provided to further illustrate the synthesis of the compounds of the present invention and not intended to limit the present invention in any way.

Example 1

Preparation of PCMI-22

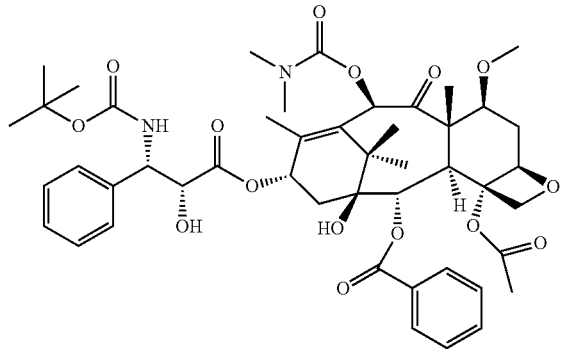

1) Preparation of (4S,5R)-3-t-butyloxy carbonyl-2-(4-methoxyphenyl)-4-phenyl-5-oxazolidine carboxylic acid

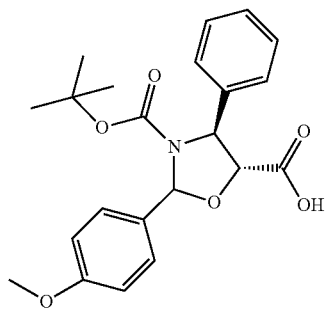 [SMILES: COc1ccc(C2O[C@@H](C(=O)O)[C@H](c3ccccc3)N2C(=O)OC(C)(C)C)cc1]

a. Preparation of benzyl glycolate

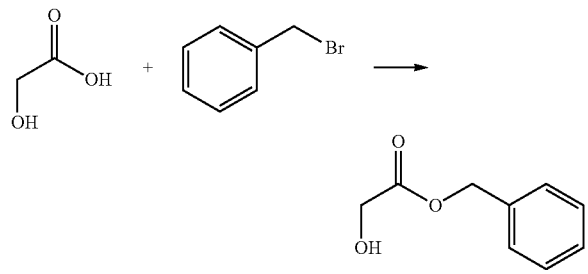

Glycolic acid (7.60 g, 0.10 mol) was dissolved in 10 ml of acetonitrile, into which benzyl bromide (13.60 g, 0.08 mol) was added and uniformly stirred. DBU (12.16 g, 0.08 mol) was slowly added dropwise into the reaction liquid at 0° C. After that, the reaction liquid was stirred overnight at room temperature. The reaction liquid was poured into the ice water, extracted with ethyl acetate, the combined resultant organic phase was washed with 1M hydrochloric acid solution and saturated salt water successively, dried with anhydrous sodium sulfate and concentrated by rotary evaporation to give the compound as a yellow oil (12.50 g, 94%).

b. Preparation of Boc-protected benzyl glycolate

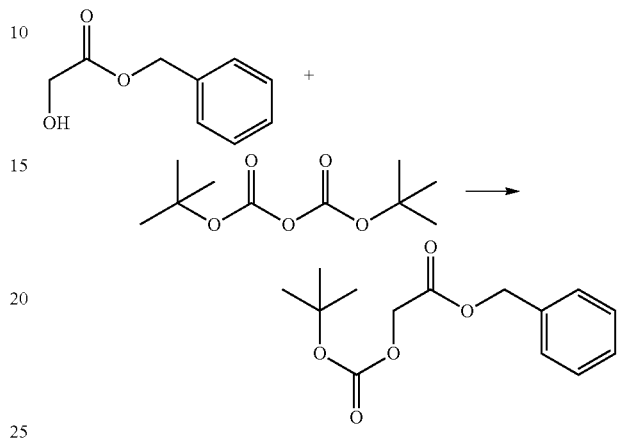

Benzyl glycolate (30 g, 0.25 mol) and Boc anhydride (39.1 g, 0.19 mol) were dissolved in 30 ml of dichloromethane. 5 ml of DMAP (4.62 g, 0.038 mol) in dichloromethane solution was added dropwise into the resultant reaction liquid at 80° C. After that, the reaction liquid was reacted at 15° C. for 0.5 h. After completion of the reaction, the reaction liquid was poured into the ice water, extracted with ethyl acetate, the combined resultant organic phase was washed with water and saturated salt water successively. The organic phase was concentrated and recrystallized with petroleum ether/ethyl acetate in a ratio of 10:1 to give a white solid (32.5 g, 66%).

c. Preparation of N-t-butyl sulfinyl benzylenamine

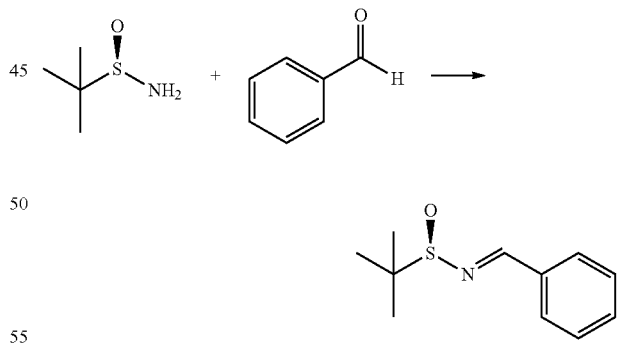

$(S_R)$-t-butyl sulfinamide (5.22 g, 0.043 mol) and benzaldehyde (5.51 g, 0.052 mol) were dissolved in 20 ml of dichloromethane and the solution was added with magnesium sulfate (25.90 g, 0.22 mol) and PPTS (0.54 g, 2.20 mmol). The reaction liquid was stirred at room temperature for 24 h, filtered and the obtained filter cake was rinsed with dichloromethane for 3 times (20 ml×3) to give the crude product after concentration. The crude product was purified by column chromatography (petroleum ether/ethyl acetate=15:1) to give a colorless oil (7.71 g, 85.8%).

d. Preparation of benzyl 2R-t-butyloxycarbonyl-3S-t-butyl sulfinamide-phenyl propionate

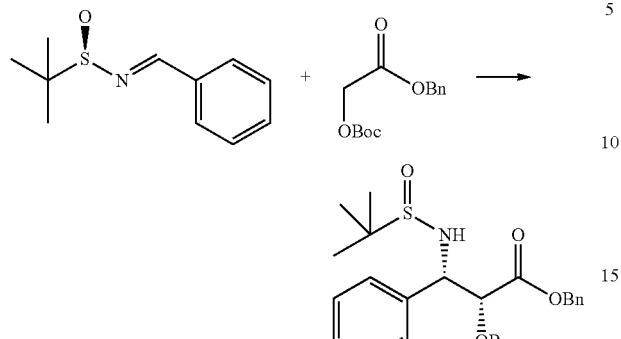

Boc-protected benzyl glycolate (32.5 g, 0.12 mol) was dissolved in 15 ml of tetrahydrofuran and LHMDS (120 ml, 0.12 mol) was slowly added dropwise into the reaction liquid at −70'C. After completion of the addition, the reaction liquid was stirred for 0.5 h, followed by the slowly adding N-t-butyl sulfinyl benzylamine in THF solution (5.02 g, 0.024 mol 8 ml of THF solution) dropwise and 4 hours later, the reaction was finished. The reaction liquid was poured into 50 ml of saturated ammonium chloride solution and extracted with ethyl acetate for 3 times (30 ml×3). The combined organic phases were dried, concentrated by rotary evaporation and purified by column chromatography (petroleum ether/ethyl acetate=10:1) to obtain a white solid (5.25 g, 46%).

e. Preparation of benzyl 2R-hydroxy-3S-aminophenyl propionate

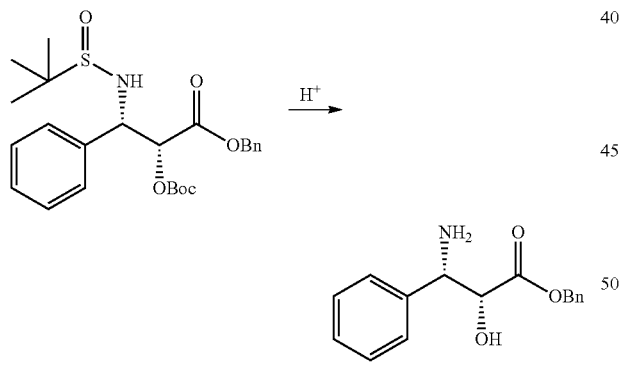

The product obtained in the previous step (5.25 g, 0.011 mol) was dissolved in 20 ml of 2N HCl/EtOAc solution and reacted at room temperature for 10 hours. After the completion of the reaction, the reaction liquid was concentrated and the obtained concentrate was extracted with dichloromethane/water (50 ml/100 ml). The aqueous phase was collected, extracted with dichloromethane and the pH value thereof was adjusted with 28% aqueous ammonia to 9-10. Finally, the aqueous phase was extracted with dichloromethane for 3 times (20 ml×3). The combined organic phase was dried, filtered and concentrated to give a white solid (2.85 g, 95.7%).

f. Preparation of benzyl (4S,5R)-2-(4-methoxyphenyl)-4-phenyl-5-oxazolidine carboxylate

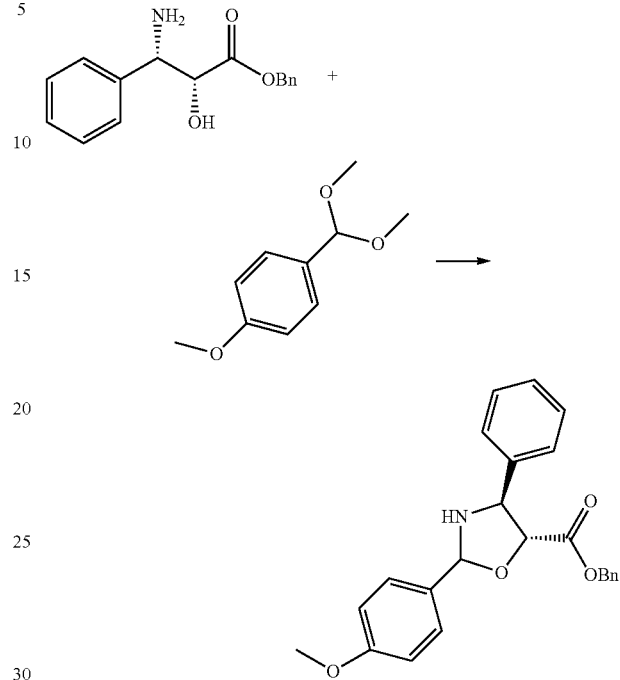

Benzyl 2R-hydroxy-3S-amino-phenyl propionate (2.66 g, 9.84 mmol) and the catalyst PPTS (0.24 g, 0.93 mmol) were dissolved in 10 ml of toluene and 1,1-dimethoxymethyl-4-methoxybenzene (2.15 g, 11.79 mmol) was slowly added dropwise into the reaction liquid at 100° C. After that, the reaction was maintained at a temperature of 90-100° C. for 2 hours, which was continued to be supplemented with 2.4 g of 1-dimethoxymethyl-4-methoxybenzene and then reacted for about 2 hours before finishing the reaction. The obtained reaction liquid was concentrated, separated and purified by column chromatography (petroleum ether/ethyl acetate=10:1), yielding a yellow oil (3.52 g, 92%). The yellow oil contained a small amount of p-methoxybenzaldehyde.

g. Preparation of benzyl (4S,5R)-3-t-butoxycarbonyl-2-(4-methoxyphenyl)-4-phenyl-5-oxazolidine carboxylate

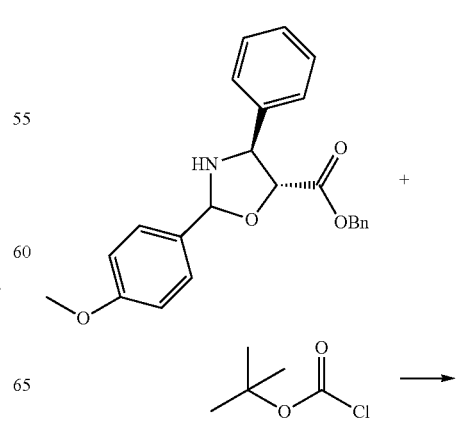

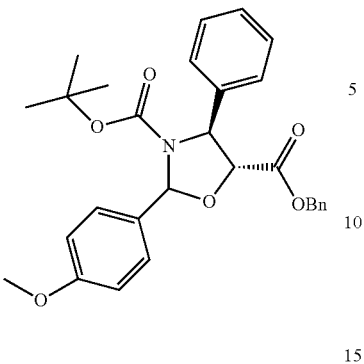

The oil obtained in the previous step (4.07 g, 10.47 mmol), t-butyloxy formyl chloride (1.56 g, 12.57 mmol) and triethylamine (2.64 g, 26.17 mol) were dissolved in 10 ml of dichloromethane and stirred overnight at room temperature. The reaction liquid was concentrated, separated and purified by column chromatography (petroleum ether/ethyl acetate=10:1) to give a yellow oil (4.83 g, 94.4%).

h. Preparation of (4S,5R)-3-t-butoxy carbonyl-2-(4-methoxyphenyl)-4-phenyl-5-oxazolidine carboxylic acid

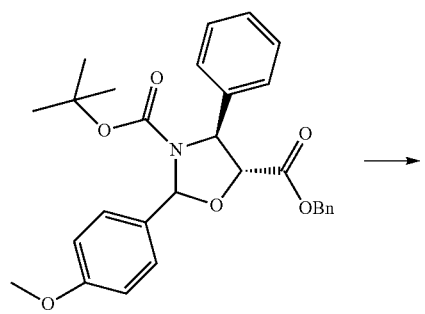

The product obtained in the previous step (4.83 g, 9.88 mmol) was dissolved in 10 ml of methanol, into which 1.0 g of palladium hydroxide was added. Hydrogen was introduced (20 psi) at room temperature and reacted for about 1 h, the completion of the reaction was monitored by TLC. The reaction liquid was filtered, concentrated, separated and purified by column chromatography (petroleum ether/ethyl acetate=5:1), to give the final product as a white solid (2.68 g, 67.9%).

2) Preparation of 10-dimethylcarbamoyl-7-methoxy baccatin III

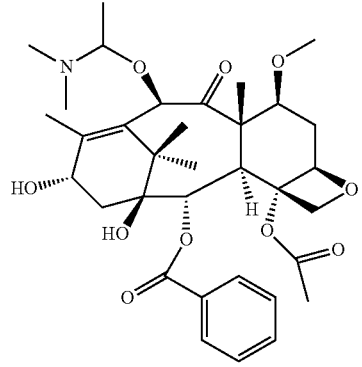

10-DAB (1 eq.) was used as raw material, dissolved in DMF and added successively with 2.5 equivalents of imidazole and 2.5 equivalents of triethyl chlorosilane. After post-treatment, the crude compound 1 as shown in the following reaction scheme was given.

The obtained compound 1 (1 eq.) was dissolved in dry THF which was used as the solvent, into which 1.5 equivalents LHMDS was added at 0° C. After 1 hour of reaction, 2 equivalents of dimethylcarbamoyl chloride was slowly added dropwise to the reaction liquid and reacted for 2 hours. By post-treatment of purification by column chromatography, the compound 2 was given in a yield of 87%.

The obtained compound 2 (1 eq.) was dissolved in dry THF, into which 1.5 equivalents of tetrabutylammonium fluoride (which is in the form of a solution in THF) was added at room temperature. After 1 hour of reaction, the reaction was finished. By post-treatment of purification by column chromatography, the compound 3 was given in a yield of 90%.

The obtained compound 3 was firstly reacted with p-toluenesulfonyl chloride in dichloromethane by using pyridine as an alkali to form the compound 4 at room temperature.

In anhydrous tetrahydrofuran, the compound 4 (1 eq.) was reacted with methyl magnesium bromide (2 eq.) at room temperature for 3 hours, under the protection of nitrogen. After post-treatment of purification by column chromatography, the compound 5 was obtained in a yield of 75%.

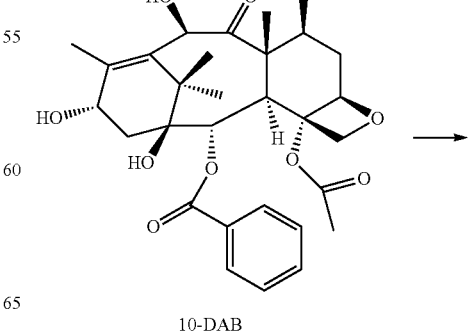

10-DAB

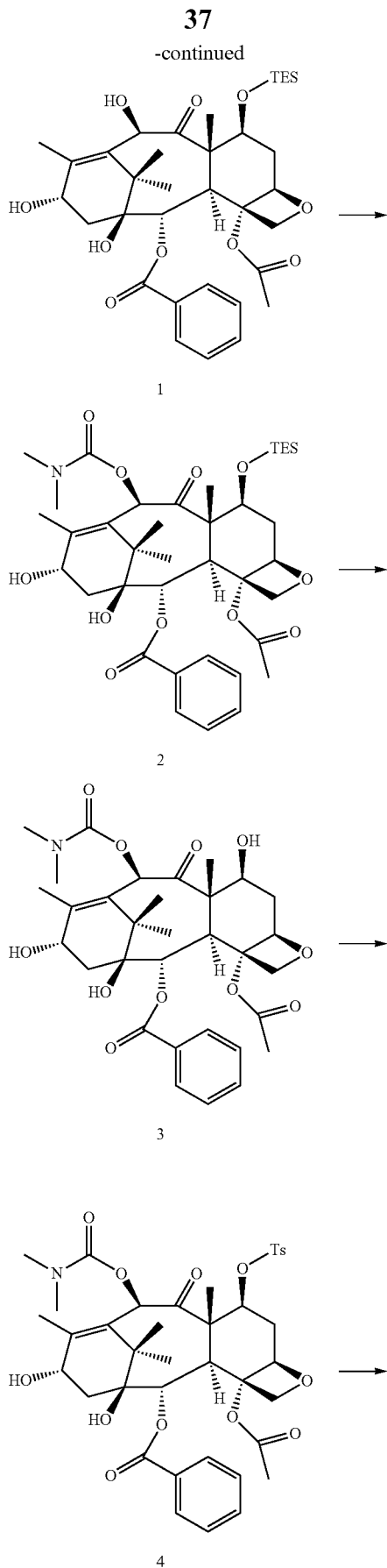

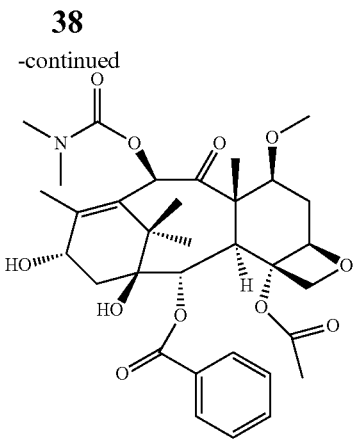

3) Preparation of PCMI-22

10-Dimethylcarbamoyl-7-methoxy baccatin III (1 eq.) and (4S,5R)-3-t-butoxycarbonyl-2-(4-methoxyphenyl)-4-phenyl-5-oxazolidine carboxylic acid (4 eq.) were dissolved in dichloromethane at room temperature, into which 0.5 equivalents of 4-dimethylaminopyridine (DMAP) and 2.0 equivalents of N,N-dicyclohexylcarbodiimide (DCC) were successively added and reacted overnight. The obtained product was reacted in 2 equivalents of acetyl chloride/methanol solution to give the final taxane derivative PCMI-22. The overall yield of the two steps was 71% and the purity of the product was 95% or higher.

PCMI-22: mp: 239–240° C.;

MS (m/z) ESI: 915.3 (M+Na)$^+$;

$^1$H NMR (400 MHz, CDCl$_3$) δ 8.11 (d, J=7.4 Hz, 2H), 7.62 (t, J=7.4 Hz, 1H), 7.50 (t, J=7.7 Hz, 2H), 7.44-7.30 (m, 5H), 6.42 (s, 1H), 6.21 (t, J=8.6 Hz, 1H), 5.67 (d, J=6.9 Hz, 1H), 5.50 (d, J=8.3 Hz, 1H), 5.28 (d, J=8.3 Hz, 1H), 4.98 (d, J=8.2 Hz, 1H), 4.64 (s, 1H), 4.31 (d, J=8.6 Hz, 1H), 4.18 (d, J=8.4 Hz, 1H), 3.92-3.82 (m, 2H), 3.55 (d, J=4.6 Hz, 1H), 3.37 (s, 3H), 3.08 (s, 3H), 2.98 (s, 3H), 2.73 (m, 1H), 2.39 (s, 3H), 2.31 (d, J=8.7 Hz, 2H), 1.95 (s, 3H), 1.82-1.76 (m, 1H), 1.74 (s, 3H), 1.37 (s, 9H), 1.24 (s, 6H).

Example 2

Preparation of PCMI-23

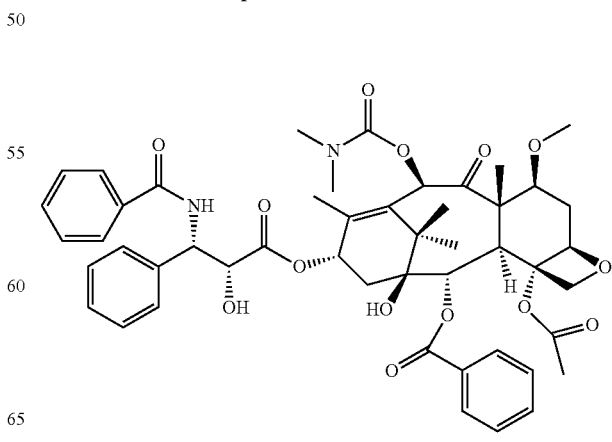

1) Preparation of (4S,5R)-3-benzoyl-2-(4-methoxy phenyl)-4-phenyl-5-oxazolidine carboxylic acid

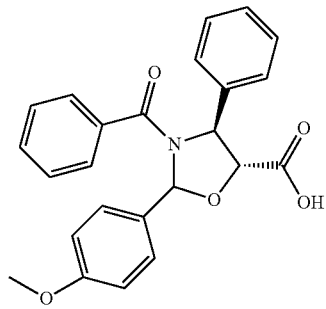 [SMILES: COc1ccc(C2O[C@@H](C(=O)O)[C@H](c3ccccc3)N2C(=O)c2ccccc2)cc1]

(4S,5R)-3-benzoyl-2-(4-methoxyphenyl)-4-phenyl-5-oxazolidine carboxylic acid was prepared by the substantially same method as shown in Example 1, except for Step g. Other steps could be seen in the reaction of Example 1.

g. Preparation of benzyl (4S,5R)-3-benzoyl-2-(4-methoxyphenyl)-4-phenyl-5-oxazolidine carboxylate

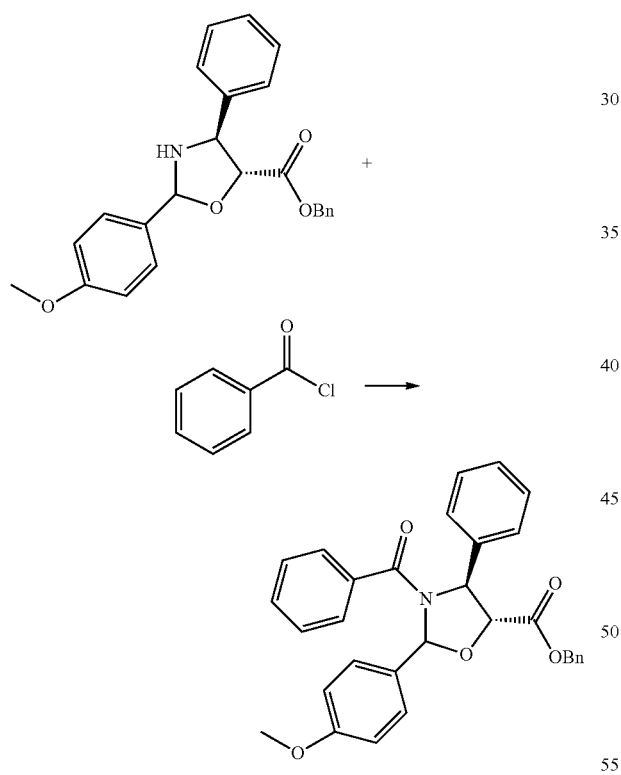

Benzyl (4S,5R)-2-(4-methoxy phenyl)-4-phenyl-5-oxazolidine carboxylate (1 eq.) was dissolved in anhydrous tetrahydrofuran, into which 1.5 equivalents of LHMDS was added at −40° C. After 1 hour of reaction, the reaction liquid was added dropwise with 2 equivalents of benzoyl chloride, reacted for 3 hours before finishing the reaction. After post-treatment of purification by column chromatography, the product was obtained in a yield of 85%.

The preparation of 10-dimethylcarbamoyl-7-methoxy baccatin III in Step 2) and PCMI-23 in Step 3) had the same procedures as those in Step 2) and Step 3) in Example 1. The procedures could be seen particularly in Step 2) and Step 3) in Example 1 and the purity of the final product was 95% or higher.

PCMI-23: mp: 228-229° C.;
MS (m/z) ESI: 919.4 (M+Na)$^+$;
$^1$H NMR (400 MHz, CDCl$_3$) δ 8.16-8.06 (m, 2H), 7.81-7.72 (m, 2H), 7.61 (t, J=7.4 Hz, 1H), 7.53-7.30 (m, 10H), 7.16 (d, J=8.9 Hz, 1H), 6.38 (s, 1H), 6.18 (t, J=8.4 Hz, 1H), 5.80 (dd, J=8.8, 2.6 Hz, 1H), 5.66 (d, J=6.9 Hz, 1H), 4.97 (d, J=8.4 Hz, 1H), 4.79 (s, 1H), 4.29 (d, J=8.1 Hz, 1H), 4.18 (d, J=8.3 Hz, 1H), 3.85 (dd, J=10.7, 6.8 Hz, 2H), 3.81-3.70 (m, 1H), 3.35 (s, 3H), 3.05 (s, 3H), 2.96 (s, 3H), 2.72 (ddd, J=16.0, 9.6, 6.7 Hz, 1H), 2.38 (s, 3H), 2.31 (dd, J=8.8, 2.8 Hz, 2H), 1.86 (s, 3H), 1.79 (m, 1H), 1.74 (d, J=8.0 Hz, 3H), 1.22 (s, 3H), 1.19 (s, 3H).
$^{13}$C NMR (101 MHz, CDCl$_3$) δ 203.72, 172.37, 171.22, 170.59, 166.98, 166.91, 155.15, 139.42, 138.00, 134.34, 133.72, 131.95, 130.17, 129.17, 128.95, 128.70, 128.32, 127.12, 127.07, 84.15, 81.75, 80.55, 78.57, 75.72, 74.44, 73.29, 72.24, 57.75, 57.23, 54.93, 47.30, 43.22, 36.74, 36.20, 35.53, 32.42, 29.70, 26.74, 22.69, 21.22, 14.62, 10.31.

Example 3

Preparation of PCMI-24

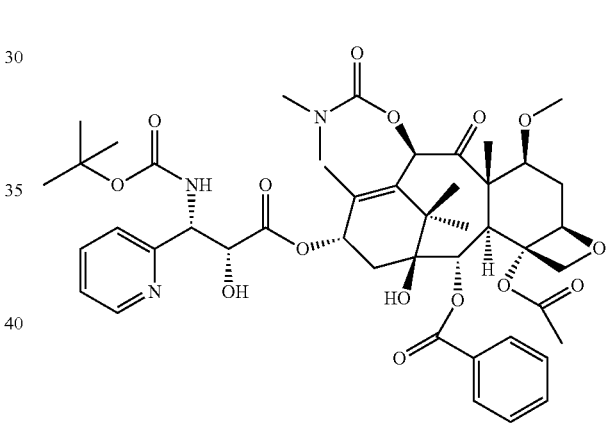

1) Preparation of (4S,5R)-3-t-butoxycarbonyl-2-(4-methoxyphenyl)-4-(2-pyridinyl)-5-oxazolidine carboxylic acid

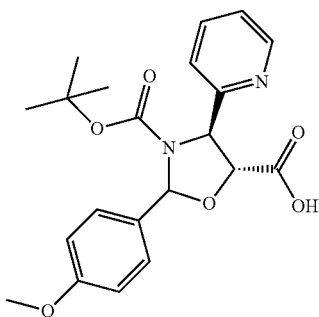 [SMILES: COc1ccc(C2O[C@@H](C(=O)O)[C@H](c3ccccn3)N2C(=O)OC(C)(C)C)cc1]

(4S,5R)-3-t-butoxycarbonyl-2-(4-methoxyphenyl)-4-(2-pyridinyl)-5-oxazolidine carboxylic acid was prepared with the substantially same method as shown in Example 1, except for Step c. Other steps could be seen in the reactions of Example 1.

c. Preparation of N-t-butyl sulfinyl-2-pyridinyl carboxaenamine

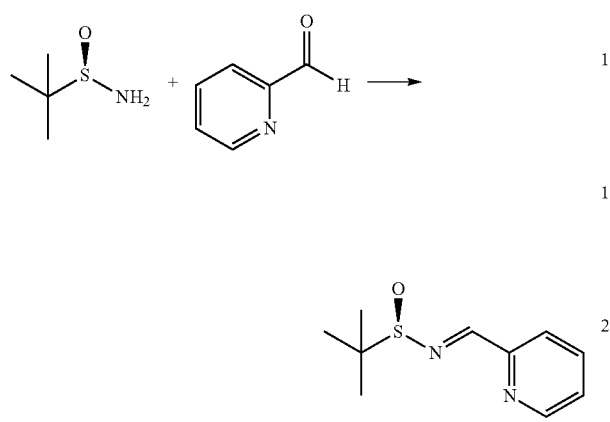

($S_R$)-t-butyl sulfinamide (5.22 g, 0.043 mol) and 2-pyridine carboxaldehyde (4.47 g, 0.052 mol) were dissolved in 20 ml of dichloromethane, into which magnesium sulfate (25.90 g, 0.22 mol) and PPTS (0.54 g, 2.20 mmol) were added. The reaction liquid was stirred at room temperature for 24 hours, filtered and the filter cake was rinsed with dichloromethane for 3 times (20 ml×3) and concentrated to give the crude product. The crude product was purified by column chromatography (petroleum ether/ethyl acetate=15:1) to give a colorless oil (7.13 g, 80.2%).

The preparation of 10-dimethylcarbamoyl-7-methoxy baccatin III in Step 2) and PCMI-24 in Step 3) had the same procedures as Step 2) and Step 3) in Example 1. The procedures could be seen particularly in Step 2) and Step 3) in Example 1 and the purity of the final product was 95% or higher.

PCMI-24: mp: 235-236° C.;

MS (m/z) ESI: 916.4 (M+Na)$^+$;

$^1$H NMR (400 MHz, CDCl$_3$) δ 8.49 (dd, J=12.1, 4.7 Hz, 1H), 8.11 (dd, J=8.7, 7.5 Hz, 2H), 7.77 (td, J=7.7, 1.7 Hz, 1H), 7.63 (t, J=7.4 Hz, 1H), 7.51 (t, J=7.7 Hz, 2H), 7.44 (d, J=7.8 Hz, 1H), 7.28-7.23 (m, 1H), 6.44 (s, 1H), 6.17 (t, J=8.7 Hz, 1H), 5.90 (d, 1H), 5.68 (d, J=7.1 Hz, 1H), 5.24 (s, 1H), 5.03 (d, J=9.5 Hz, 1H), 4.80 (s, 1H), 4.33 (d, J=8.5 Hz, 1H), 4.18 (d, J=8.6 Hz, 1H), 3.99-3.94 (m, 1H), 3.92 (d, J=7.2 Hz, 1H), 3.87 (m, 1H), 3.39 (s, 3H), 3.07 (s, 3H), 2.98 (s, 3H), 2.82-2.71 (m, 1H), 2.49 (s, 3H), 2.01 (s, 3H), 1.86-1.77 (m, 4H), 1.64 (s, 3H), 1.28 (d, J=1.9 Hz, 12H).

$^{13}$C NMR (101 MHz, CDCl$_3$) δ 203.86, 170.64, 167.06, 155.18, 148.40, 137.58, 133.69, 130.14, 129.21, 128.66, 122.96, 121.90, 84.25, 81.29, 80.54, 78.96, 75.72, 74.65, 60.41, 57.76, 57.15, 47.37, 43.23, 36.74, 36.18, 32.32, 31.94, 29.71, 28.31, 27.95, 26.50, 22.46, 21.06, 14.59, 14.17, 10.31.

Example 4

Preparation of PCMI-25

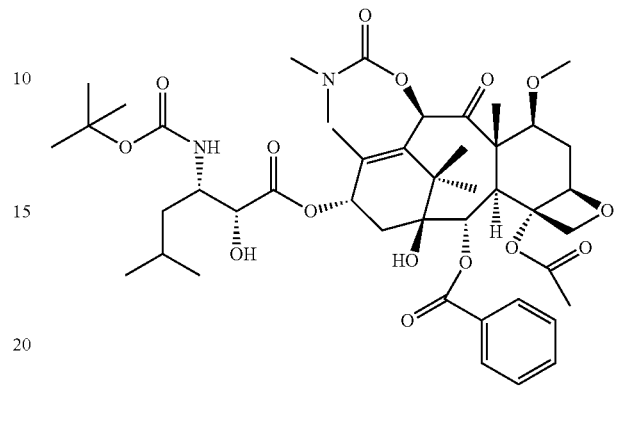

1) Preparation of (4S,5R)-3-t-butoxycarbonyl-2-(4-methoxyphenyl)-4-isobutyl-5-oxazolidine carboxylic acid

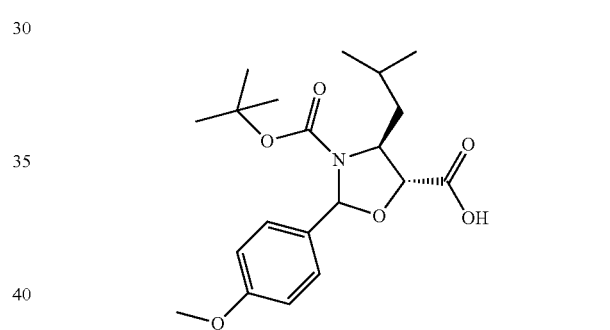

(4S,5R)-3-t-butoxycarbonyl-2-(4-methoxyphenyl)-4-isobutyl-5-oxazolidine carboxylic acid was prepared with the substantially same method as shown in Example 1, except for Step c. Other steps could be seen in the reaction of Example 1.

c. Preparation of N-t-butyl sulfinyl isobutyl carboxaenamine

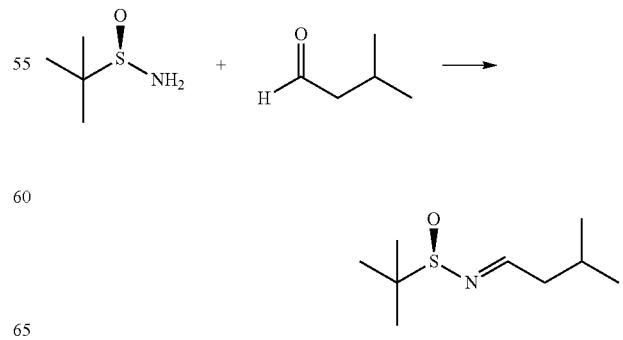

($S_R$)-t-butyl sulfinamide (5.22 g, 0.043 mol) and isovaleraldehyde (5.51 g, 0.052 mol) were dissolved in 20 ml of dichloromethane, into which magnesium sulfate (25.90 g, 0.22 mol) and PPTS (0.54 g, 2.20 mmol) were added. The reaction liquid was stirred for 24 hours at room temperature, filtered and the filter cake was rinsed with dichloromethane for 3 times (20 ml×3) and concentrated to give the crude product. The crude product was purified by column chromatography (petroleum ether/ethyl acetate=15:1) to give a colorless oil (7.26 g, 89.3%).

The preparation of 10-dimethylcarbamoyl-7-methoxy baccatin III in Step 2) and PCMI-25 in Step 3) had the same procedures as Step 2) and Step 3) in Example 1. The procedures could be seen particularly in Step 2) and Step 3) in Example 1 and the purity of the final product was 95% or higher.

PCMI-25: mp: 221-222° C.;

MS (m/z) ESI: 873.0 (M+H)$^+$;

$^1$H NMR (400 MHz, CDCl$_3$) δ 8.11 (d, J=7.5 Hz, 2H), 7.61 (t, J=7.4 Hz, 1H), 7.48 (t, J=7.7 Hz, 2H), 6.43 (s, 1H), 6.16 (t, J=8.7 Hz, 1H), 5.67 (d, J=7.0 Hz, 1H), 4.99 (d, J=8.2 Hz, 1H), 4.63 (d, J=9.7 Hz, 1H), 4.31 (d, J=8.4 Hz, 1H), 4.19 (d, J=8.0 Hz, 2H), 3.93-3.85 (m, 2H), 3.36 (s, 3H), 3.32 (d, J=6.0 Hz, 1H), 3.06 (s, 3H), 2.97 (s, 3H), 2.73 (ddd, J=15.9, 9.7, 6.6 Hz, 1H), 2.39 (s, 5H), 2.02 (s, 3H), 1.84-1.75 (m, 1H), 1.73 (s, 3H), 1.70-1.65 (m, 1H), 1.33 (s, 10H), 1.23 (s, 3H), 1.22 (s, 3H), 0.98 (dd, J=6.3, 2.8 Hz, 6H).

$^{13}$C NMR (101 MHz, CDCl$_3$) δ 203.78, 173.78, 170.09, 166.91, 155.56, 155.16, 140.08, 133.99, 133.62, 130.19, 129.27, 128.63, 84.17, 81.60, 80.52, 79.7, 78.74, 76.42, 75.75, 74.66, 73.05, 72.62, 57.77, 57.14, 51.34, 47.29, 43.28, 41.11, 36.73, 36.18, 35.39, 32.34, 29.70, 28.20, 26.45, 24.72, 23.31, 22.60, 21.91, 21.46, 21.06, 14.65, 14.20, 10.32.

Example 5

Preparation of PCMI-26

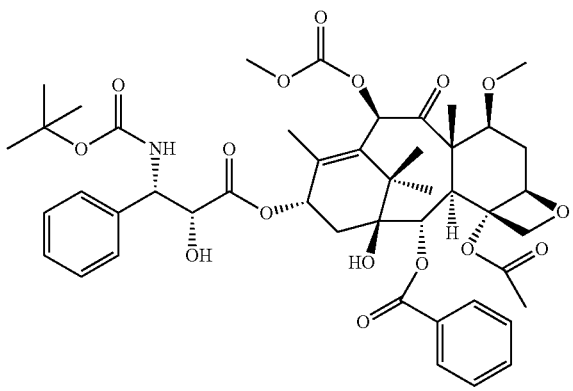

1) Preparation of (4S,5R)-3-t-butyloxy carbonyl-2-(4-methoxyphenyl)-4-phenyl-5-oxazolidine carboxylic acid The specific method was seen in Example 1.

2) Preparation of 10-methoxylcarbamoyl-7-methoxy baccatin III

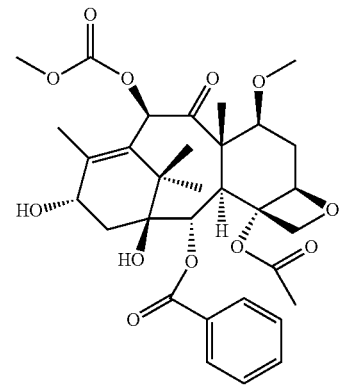

10-DAB (1 eq.) was used as raw material, dissolved in DMF and added successively with 2.5 equivalents of imidazole and 2.5 equivalents of triethyl chlorosilane. After post-treatment, the crude compound 1 as shown in the following reaction scheme was given.

The compound 1 (1 eq.) was dissolved in dry THF which was used as the solvent, into which 1.5 equivalents LHMDS was added at 0'C. After 1 hour of reaction, 2 equivalents of methoxyl formyl chloride was slowly added dropwise to the reaction liquid and reacted for 2 hours. By post-treatment of purification by column chromatography, the compound 6 was given in a yield of 62%.

The compound 6 (1 eq.) was dissolved in dry THEF into which 1.5 equivalents of tetrabutylammonium fluoride (which is in the form of a solution in THF) was added at room temperature. After 1 hour of reaction, the reaction was completed. By post-treatment of purification by column chromatography, the compound 7 was given in a yield of 90%.

The compound 7 was firstly reacted with p-toluenesulfonyl chloride in dichloromethane by using pyridine as an alkali to form the compound 8 at room temperature.

In anhydrous tetrahydrofuran, the compound 8 (1 eq.) was reacted with methyl magnesium bromide (2 eq.) for 3 hours at room temperature under the protection of nitrogen. By post-treatment of purification by column chromatography, the compound 9 was given in a yield of 71%.

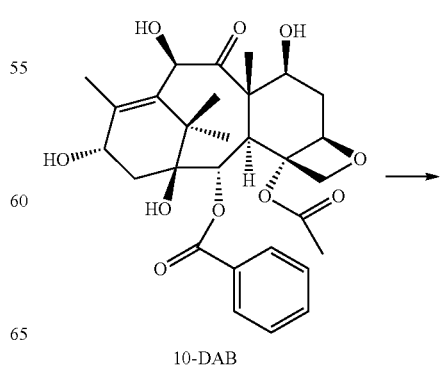

10-DAB

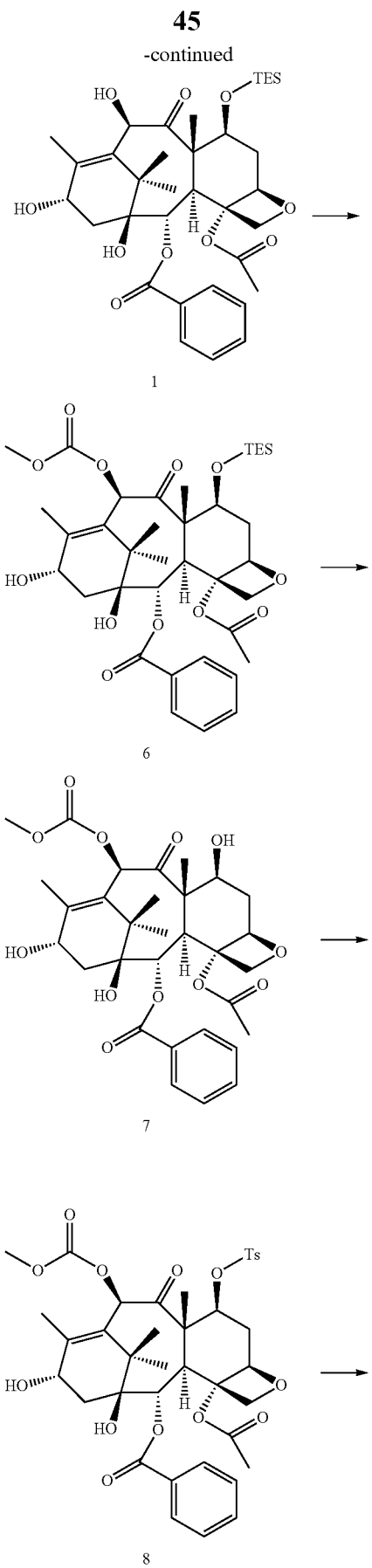
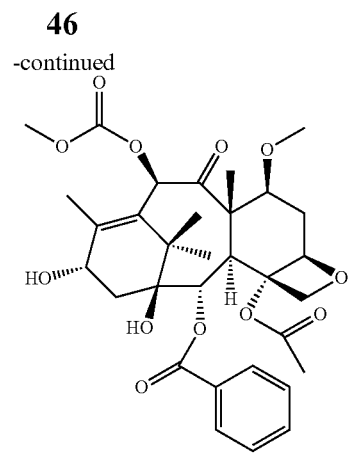
3) Preparation of PCMI-26
The specific method was seen in Step 3) in Example 1 and the purity of the final product was 95% or higher.
PCMI-26: mp: 227-228° C.;
MS (m/z) ESI: 902.4 (M+Na)$^+$;
$^1$H NMR (400 MHz, DMSO) δ 7.99 (d, J=7.4 Hz, 2H), 7.72 (t, J=7.4 Hz, 1H), 7.63 (t, J=7.5 Hz, 2H), 7.38 (m, 5H), 7.22 (t, J=7.2 Hz, 1H), 6.08 (s, 1H), 5.95 (d, J=8.8 Hz, 1H), 5.92-5.87 (m, 1H), 5.43 (d, J=7.1 Hz, 1H), 4.98 (d, J=9.9 Hz, 1H), 4.92 (dd, J=8.8, 6.8 Hz, 1H), 4.78 (s, 1H), 4.37 (t, J=7.1 Hz, 1H), 4.04 (s, 2H), 3.77 (s, 4H), 3.62 (d, J=6.9 Hz, 1H), 3.22 (s, 3H), 2.73-2.68 (m, 1H), 2.26 (s, 3H), 1.85 (s, 3H), 1.77-1.68 (m, 1H), 1.56 (s, 3H), 1.51 (d, J=9.8 Hz, 2H), 1.36 (s, 9H), 1.04 (s, 4H), 1.00 (s, 3H).
$^{13}$C NMR (101 MHz, DMSO) δ 202.12, 173.31, 170.54, 165.64, 155.59, 154.53, 141.23, 139.98, 133.95, 133.04, 130.30, 130.05, 129.18, 128.68, 127.69, 83.55, 80.56, 78.63, 78.06, 77.14, 74.45, 70.21, 57.43, 56.84, 55.51, 47.97, 46.83, 43.35, 35.02, 33.81, 32.33, 28.61, 26.81, 25.79, 24.92, 22.88, 21.60, 14.60, 10.59.
Example 6
Preparation of PCMI-27
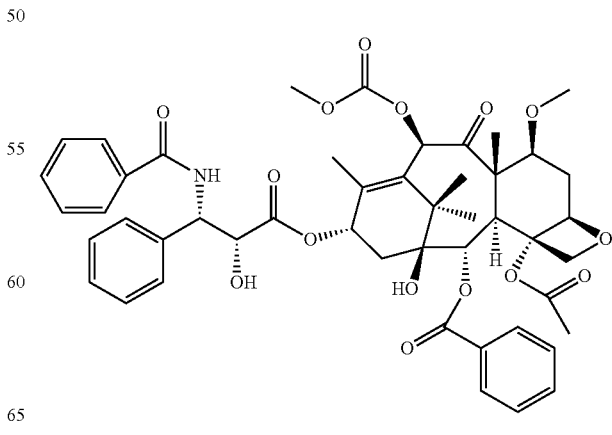

1) Preparation of (4S,5R)-3-benzoyl-2-(4-methoxyphenyl)-4-phenyl-5-oxazolidine carboxylic acid The specific method was seen in Step 1) in Example 2.

2) Preparation of 10-methoxylcarbamoyl-7-methoxy baccatin III

The specific method was seen in Step 2) in Example 5.

3) Preparation of PCMI-27

The specific method was seen in Step 3) in Example 1 and the purity of the final product was 95% or higher.

PCMI-27: mp: 223-224° C.;
MS (m/z) ESI: 906.3 (M+Na)+;
$^1$H NMR (400 MHz, CDCl$_3$) δ 8.14-8.08 (m, 2H), 7.81-7.74 (m, 2H), 7.62 (t, J=7.4 Hz, 1H), 7.50 (dd, J=12.7, 4.6 Hz, 5H), 7.40 (ddd, J=17.6, 10.5, 5.1 Hz, 5H), 7.23 (d, J=8.9 Hz, 1H), 6.22-6.13 (m, 2H, H-13), 5.79 (dd, J=8.9, 2.7 Hz, 1H), 5.69-5.62 (m, 1H), 4.97 (d, J=8.4 Hz, 1H), 4.80 (dd, J=4.7, 2.9 Hz, 1H), 4.30 (d, J=8.4 Hz, 1H), 4.18 (d, J=8.4 Hz, 1H), 3.91-3.82 (m, 5H), 3.80 (d, J=6.9 Hz, 1H), 3.36 (s, 3H), 2.73 (m, 1H), 2.39 (s, 3H), 2.35-2.28 (m, 2H), 1.83 (s, 3H), 1.78 (m, 1H), 1.76 (d, J=6.1 Hz, 3H), 1.20 (s, 6H).
$^{13}$C NMR (101 MHz, CDCl$_3$) δ 202.07, 172.42, 171.28, 170.64, 167.08, 166.87, 154.77, 140.51, 137.94, 133.69, 133.39, 131.97, 130.16, 129.04, 128.69, 128.33, 127.11, 84.06, 81.61, 80.47, 78.56, 77.98, 76.47, 74.33, 73.35, 72.12, 57.60, 57.19, 55.17, 47.22, 43.14, 35.40, 32.30, 26.63, 22.66, 20.98, 14.70, 10.33.

Example 7

Preparation of PCMI-28

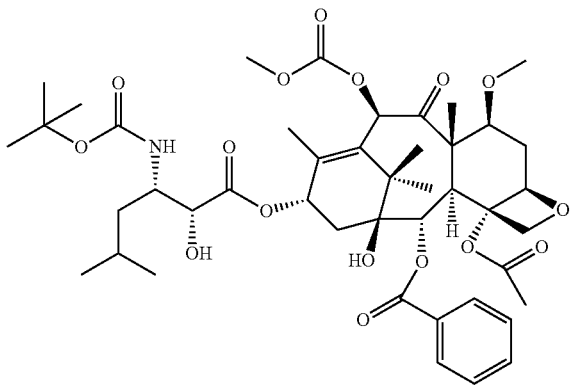

1) Preparation of (4S,5R)-3-t-butyloxycarbonyl-2-(4-methoxyphenyl)-4-isobutyl-5-oxazolidine carboxylic acid The specific method was seen in Step 1) in Example 4.

2) Preparation of 10-methoxylcarbamoyl-7-methoxy baccatin III

The specific method was seen in Step 2) in Example 5.

3) Preparation of PCMI-28

The specific method was seen in Step 3) in Example 1. The purity of the final product was 95% or higher.

PCMI-28: mp: 235-236° C.;
MS (m/z) ESI: 882.4 (M+Na)+;
$^1$H NMR (400 MHz, CDCl$_3$) δ 8.12 (d, J=7.5 Hz, 2H), 7.62 (t, J=7.4 Hz, 1H), 7.49 (t, J=7.7 Hz, 2H), 6.23 (s, 1H), 6.17 (t, J=8.8 Hz, 1H), 5.67 (d, J=7.0 Hz, 1H), 5.01 (d, J=8.3 Hz, 1H), 4.65 (d, J=9.7 Hz, 1H), 4.33 (d, J=8.4 Hz, 1H), 4.20 (d, J=7.8 Hz, 2H), 3.95-3.81 (m, 5H), 3.42-3.32 (m, 4H), 2.76 (ddd, J=15.9, 9.6, 6.5 Hz, 1H), 2.49-2.31 (m, 5H), 2.01 (s, 3H), 1.88-1.77 (m, 1H), 1.78-1.64 (m, 5H), 1.35 (s, 10H), 1.23 (d, J=7.0 Hz, 6H), 1.00 (dd, J=6.2, 3.2 Hz, 6H).
$^{13}$C NMR (101 MHz, CDCl$_3$) δ 202.10, 173.81, 170.17, 166.88, 155.57, 154.80, 141.15, 133.64, 133.12, 130.19, 129.23, 128.64, 84.08, 81.54, 80.43, 79.77, 78.70, 78.04, 76.41, 74.54, 73.05, 72.57, 57.60, 57.13, 55.17, 51.36, 47.22, 43.21, 41.10, 35.24, 32.25, 29.70, 28.19, 26.36, 24.71, 23.29, 22.58, 21.91, 14.79, 10.34.

Example 8

Preparation of PCMI-29

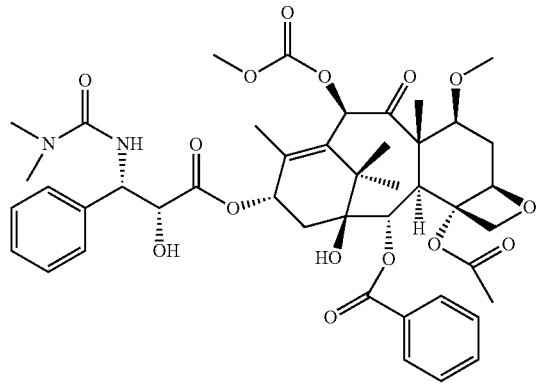

1) Preparation of (4S,5R)-3-dimethylcarbamoyl-2-(4-methoxy phenyl)-4-phenyl-5-oxazolidine carboxylic acid

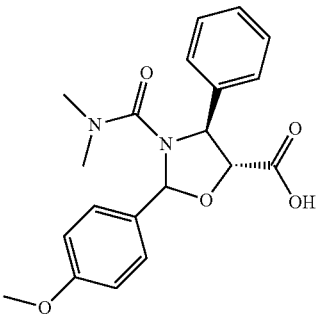 [SMILES: COc1ccc(C2O[C@@H](C(=O)O)[C@H](c3ccccc3)N2C(=O)N(C)C)cc1]

(4S,5R)-3-dimethylcarbamoyl-2-(4-methoxyphenyl)-4-phenyl-5-oxazolidine carboxylic acid was prepared with the substantially same method as shown in Step 1) of Example 1, except for Step g. Other steps could be seen in the reactions in Step 1) of Example 1.

g. Preparation of benzyl (4S,5R)-3-dimethylcarbamoyl-2-(4-methoxyphenyl)-4-phenyl-5-oxazolidine carboxylate

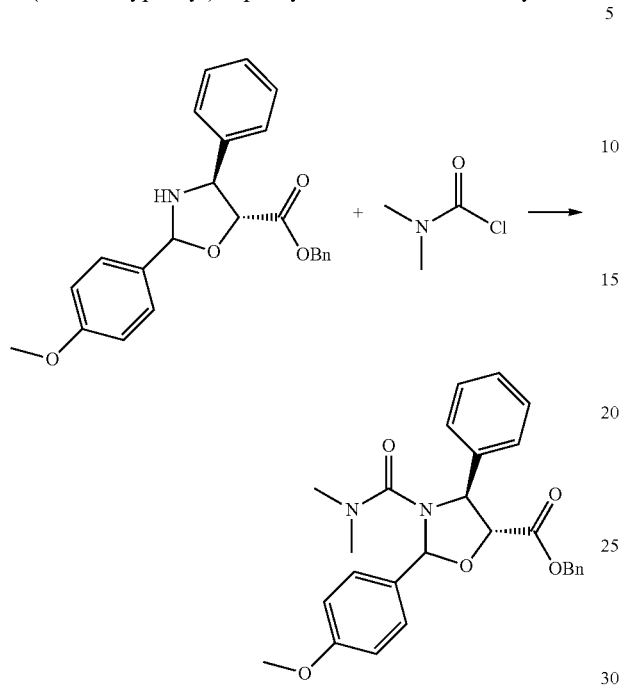

Benzyl (4S,5R)-2-(4-methoxyphenyl)-4-phenyl-5-oxazolidine carboxylate (1 eq.) was dissolved in dry tetrahydrofuran, into which 1.5 equivalents of LHMDS was added at −40° C. After 1 hour of reaction, the reaction liquid was added dropwise with 2 equivalents of dimethylcarbamoyl chloride, reacted for 3 hours before finishing the reaction. By post-treatment of purification by column chromatography, the product was obtained in a yield of 80%.

2) Preparation of 10-methoxyl formyl-7-methoxy baccatin III

The specific method was seen in step 2) in Example 5.

3) Preparation of PCMI-29

The specific method was seen in Step 3) in Example 1 and the purity of the final product was 95% or higher.

PCMI-29: mp: 227-228° C.;
MS (m/z) ESI: 873.0 (M+Na)$^+$;
$^1$H NMR (400 MHz, DMSO) δ 7.99 (d, J=7.4 Hz, 2H), 7.72 (t, J=7.4 Hz, 1H), 7.63 (t, J=7.5 Hz, 2H), 7.38 (m, 5H), 7.22 (t, J=7.2 Hz, 1H), 6.08 (s, 1H), 5.95 (d, J=8.8 Hz, 1H), 5.92-5.87 (m, 1H), 5.43 (d, J=7.1 Hz, 1H), 4.98 (d, J=9.9 Hz, 1H), 4.92 (dd, J=8.8, 6.8 Hz, 1H), 4.78 (s, 1H), 4.37 (t, J=7.1 Hz, 1H), 4.04 (s, 2H), 3.77 (s, 4H), 3.62 (d, J=6.9 Hz, 1H), 3.22 (s, 3H), 2.73-2.68 (m, 1H), 2.26 (s, 3H), 1.85 (s, 3H), 1.77-1.68 (m, 1H), 1.56 (s, 3H), 1.51 (d, J=9.8 Hz, 2H), 1.36 (s, 9H), 1.04 (s, 4H), 1.00 (s, 3H).
$^{13}$C NMR (101 MHz, DMSO) δ 202.12, 173.31, 170.54, 165.64, 155.59, 154.53, 141.23, 139.98, 133.95, 133.04, 130.30, 130.05, 129.18, 128.68, 127.69, 83.55, 80.56, 78.63, 78.06, 77.14, 74.45, 70.21, 57.43, 56.84, 55.51, 47.97, 46.83, 43.35, 35.02, 33.81, 32.33, 28.61, 26.81, 25.79, 24.92, 22.88, 21.60, 14.60, 10.59.

Example 9

Preparation of PCMI-30

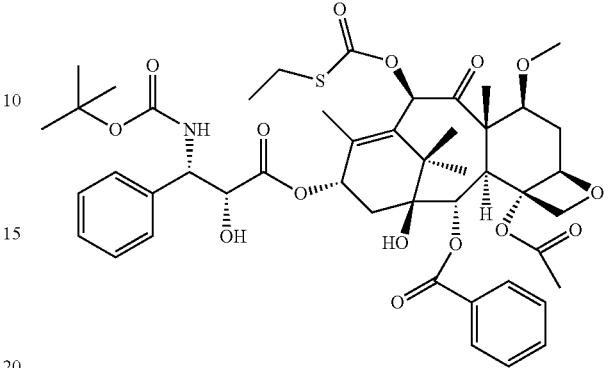

1) Preparation of (4S,5R)-3-t-butyloxycarbonyl-2-(4-methoxyphenyl)-4-phenyl-5-oxazolidine carboxylic acid The specific method was seen in Example 1.

2) Preparation of 10-ethylthioformyl-7-methoxy baccatin III

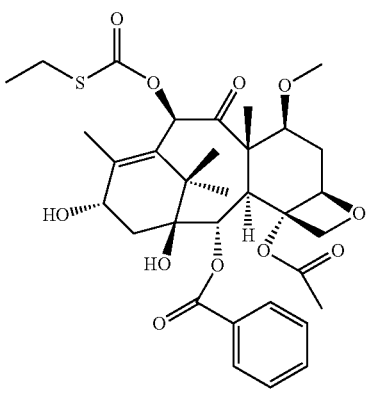

10-DAB (1 eq.) was used as raw material, dissolved in DMF and added successively with 2.5 equivalents of imidazole and 2.5 equivalents of triethyl chlorosilane. After post-treatment, the crude compound 1 as shown in the following reaction scheme was given.

The compound 1 (1 eq.) was dissolved in dry THF which was used as the solvent and firstly reacted with 2 equivalents of N,N-carbonyldiimidazole for 2 hours at room temperature. The reaction liquid was then added with 2 equivalents of ethanethiol and reacted for 4 hours. By post-treatment of purification by column chromatography, the compound 10 was given in a yield of 72%.

The compound 10 (1 eq.) was dissolved in dry THF, into which 1.5 equivalents of tetrabutylammonium fluoride (which is in the form of a solution in THF) was added at room temperature. After 1 hour of reaction, the reaction was completed. By post-treatment of purification by column chromatography, the compound 11 was given in a yield of 90%.

The compound 11 was firstly reacted with p-toluenesulfonyl chloride to form the compound 12.

In anhydrous tetrahydrofuran, the compound 12 (1 eq.) was reacted with methyl magnesium bromide (2 eq.) for 3 hours at room temperature under the protection of nitrogen. By post-treatment of purification by column chromatography, the compound 13 was given in a yield of 69%.

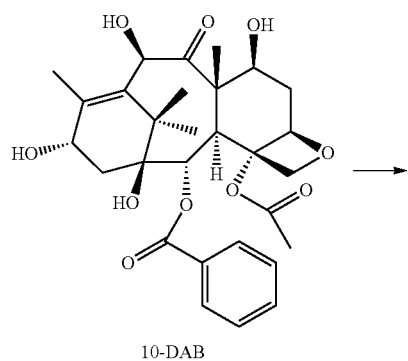

10-DAB

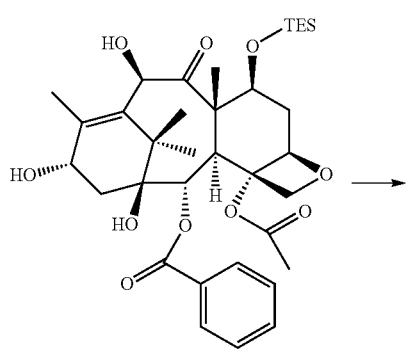

1

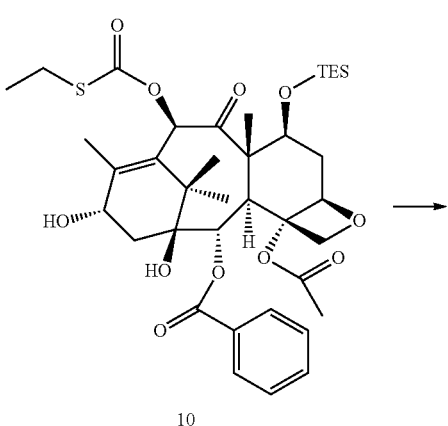

10

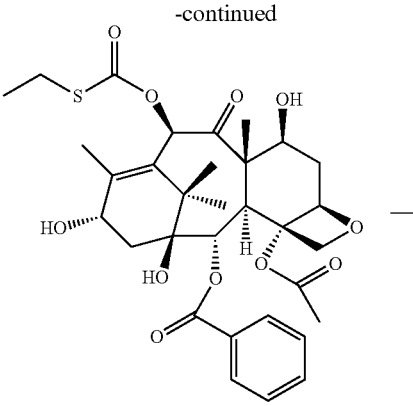

11

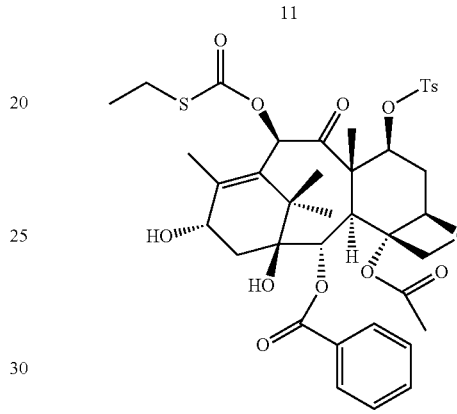

12

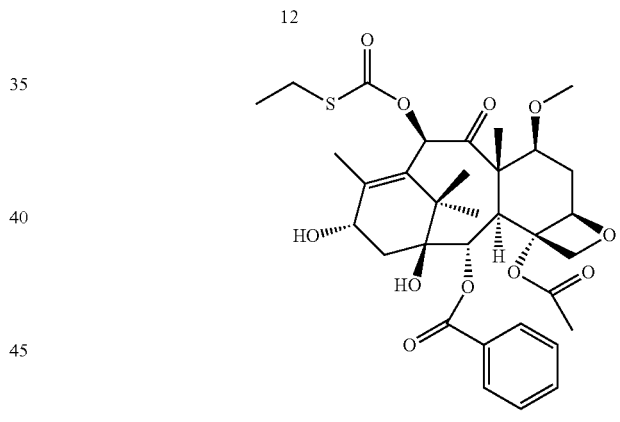

13

3) Preparation of PCMI-30

The specific method was seen in Step 3) in Example 1. The purity of the final product was 95% or higher.

PCMI-30: mp: 235-236° C.;
MS (m/z) ESI: 910.6 (M+H)$^+$:
$^1$H NMR (400 MHz, CDCl$_3$) δ 8.13-8.03 (m, 2H), 7.62 (t, J=7.4 Hz, 1H), 7.53-7.40 (m, 4H), 6.96 (d, J=8.7 Hz, 2H), 6.39 (s, 1H), 6.32 (t, J=8.8 Hz, 1H), 5.72 (d, J=7.0 Hz, 1H), 5.45 (dd, J=10.5, 7.3 Hz, 1H), 5.21 (s, 1H), 4.98 (d, J=9.1 Hz, 1H), 4.59 (s, 1H), 4.54-4.44 (m, 1H), 4.33 (d, J=8.4 Hz, 1H), 4.21 (d, J=8.4 Hz, 1H), 4.01 (d, J=6.9 Hz, 1H), 3.86 (s, 3H), 3.77 (s, 3H), 3.41 (s, 3H), 2.70-2.59 (m, 1H), 2.39-2.21 (m, 5H), 2.11 (s, 3H), 2.08-1.99 (m, 1H), 1.83 (s, 3H), 1.38 (s, 9H), 1.26 (s, 3H), 1.20 (s, 3H), 1.05 (dd, J=13.9, 5.9 Hz, 6H).

$^{13}$C NMR (101 MHz, CDCl$_3$) δ 202.12, 171.91, 171.24, 170.81, 164.68, 155.71, 154.81, 151.92, 138.16, 137.39, 134.64, 134.15, 129.93, 128.95, 128.12, 128.01, 126.63, 88.01, 84.02, 81.04, 80.60, 80.16, 79.68, 75.91, 75.00, 74.74, 74.34, 69.12, 57.81, 57.36, 46.68, 41.83, 36.81, 36.21, 32.12, 28.26, 25.87, 22.75, 22.62, 14.55, 10.39.

Example 10

Preparation of PCMI-31

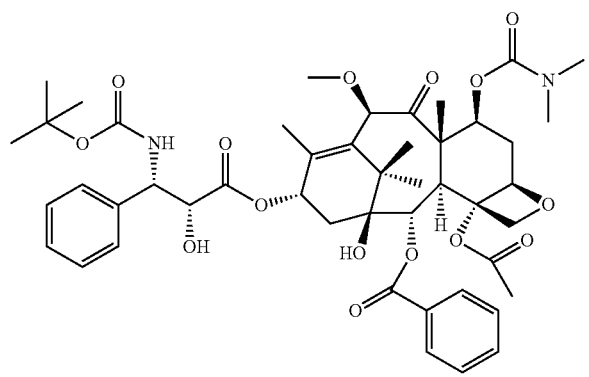

1) Preparation of (4S,5R)-3-t-butyloxycarbonyl-2-(4-methoxyphenyl)-4-phenyl-5-oxazolidine carboxylic acid The specific method was seen in Example 1.

2) Preparation of 7-dimethylcarbamoyl-10-methoxy baccatin III

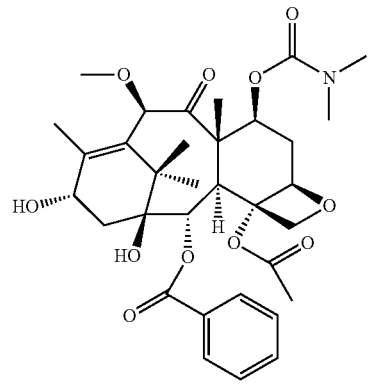

10-DAB (1 eq.) was used as raw material, dissolved in DMF and added successively with 2.5 equivalents of imidazole and 2.5 equivalents of triethyl chlorosilane. After post-treatment, the crude compound 1 as shown in the following reaction scheme was given.

The compound 1 was dissolved in dichloromethane which was used as the solvent, into which 2 equivalents of pyridine was added at 0° C. Then 2 equivalents of p-toluensulfonyl chloride was added dropwise into the reaction liquid. After 4 hours of reaction, by post-treatment of purification by column chromatography, the compound 14 was given in a yield of 90%.

The compound 14 (1 eq.) was dissolved in anhydrous tetrahydrofuran and reacted with methyl magnesium bromide (2 eq.) for 3 hours at room temperature under the protection of nitrogen. By post-treatment, the crude compound 15 was given after dried.

The compound 15 (1 eq.) was dissolved in dry THF, into which 1.5 equivalents of tetrabutylammonium fluoride (which is in the form of a solution in THF) was added at room temperature. After 1 hour of reaction, the reaction was completed. By post-treatment of purification by column chromatography, the compound 16 was given in a yield of 90%.

The compound 16 (1 eq.) was dissolved in dry THF solvent, into which 1.5 equivalents LHMDS was added at 0° C. After 1 hour of reaction, 2 equivalents of dimethylcarbamoyl chloride was slowly added dropwise to the reaction liquid and reacted for 2 hours. By post-treatment of purification by column chromatography, the compound 17 was given in a yield of 87%.

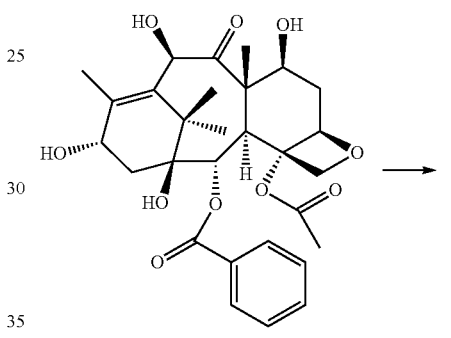

10-DAB

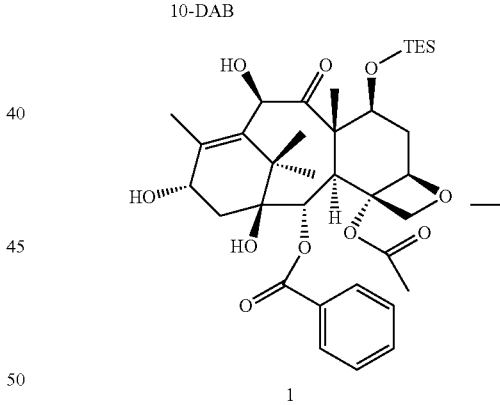

1

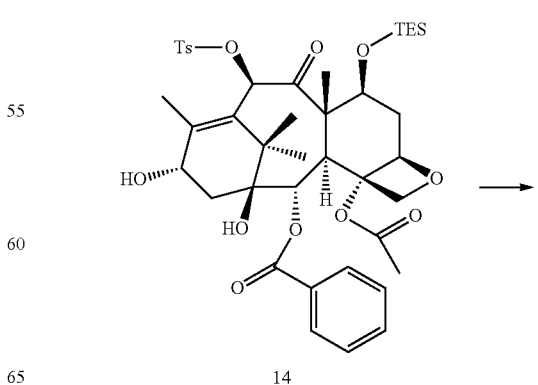

14

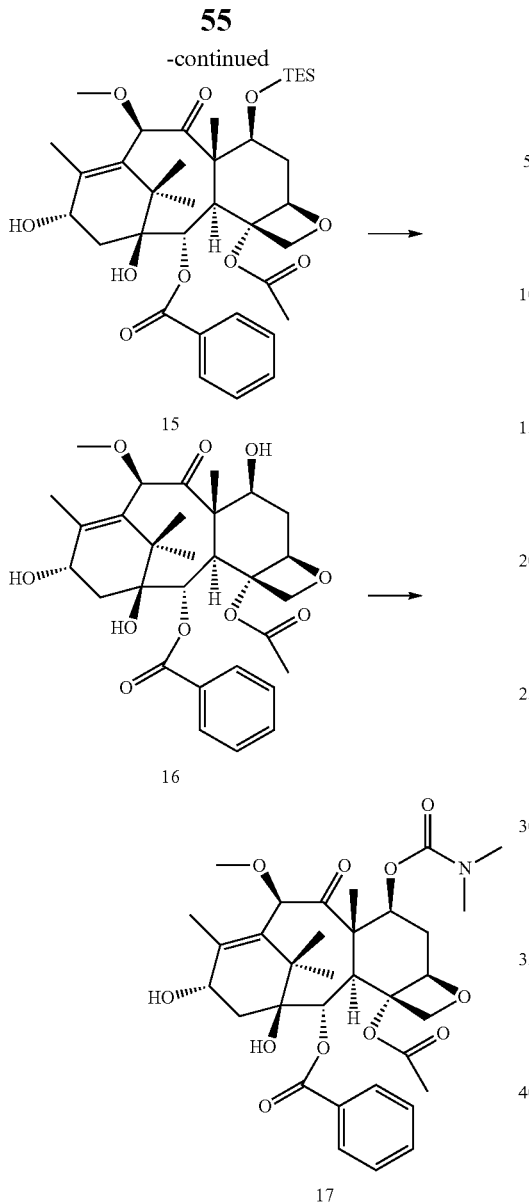

3) Preparation of PCMI-31

The specific method was seen in Step 3) in Example 1. The purity of the final product was 95% or higher.

PCMI-31: mp: 247-249° C.;

MS (m/z) ESI: 914.6 (M+Na)+;

$^1$H NMR (400 MHz, CDCl$_3$) δ 8.12 (d, J=7.4 Hz, 2H), 7.62 (t, J=7.4 Hz, 1H), 7.51 (t, J=7.7 Hz, 2H), 7.41 (d, J=4.6 Hz, 4H), 7.33 (dd, J=8.8, 4.4 Hz, 1H), 6.24 (t, J=8.4 Hz, 1H), 5.69 (d, J=6.9 Hz, 1H), 5.51 (d, J=9.2 Hz, 1H), 5.45 (dd, J=10.5, 7.4 Hz, 1H), 5.30 (d, J=9.2 Hz, 1H), 5.21 (s, 1H), 4.95 (d, J=8.3 Hz, 1H), 4.65 (s, 1H), 4.32 (d, J=8.4 Hz, 1H), 4.21 (d, J=8.3 Hz, 1H), 3.96 (d, J=6.9 Hz, 1H), 3.57 (d, J=4.0 Hz, 1H), 3.38 (s, 3H), 2.87 (d, J=4.5 Hz, 6H), 2.57 (m, 1H), 2.39 (s, 3H), 2.31 (d, J=9.0 Hz, 2H), 2.01-1.89 (m, 4H), 1.81 (s, 3H), 1.36 (s, 9H), 1.22 (s, 3H), 1.19 (s, 3H).

$^{13}$C NMR (101 MHz, CDCl$_3$) δ 206.26, 170.00, 167.03, 156.84, 155.32, 155.03, 139.40, 134.91, 133.66, 130.18, 129.20, 128.74, 127.98, 126.79, 84.06, 82.76, 80.95, 80.11, 78.78, 76.57, 74.75, 73.63, 72.74, 72.47, 60.42, 56.77, 49.17, 46.48, 43.18, 36.53, 35.89, 35.37, 33.95, 29.70, 28.21, 26.38, 25.61, 24.94, 22.58, 20.62, 14.44, 10.79.

Example 11

Preparation of PCMI-32

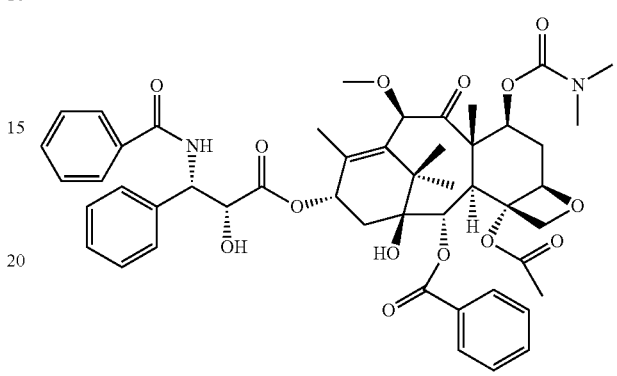

1) Preparation of (4S,5R)-3-benzoyl-2-(4-methoxy phenyl)-4-phenyl-5-oxazolidine carboxylic acid The specific method was seen in Step 1) in Example 2.

2) Preparation of 7-dimethylcarbamoyl-10-methoxy baccatin III

The specific method was seen in Step 2) in Example 10.

3) Preparation of PCMI-32

The specific method was seen in Step 3) in Example 1. The purity of the final product was 95% or higher.

PCMI-32: mp: 233-235° C.;

MS (m/z) ESI: 919.0 (M+Na)+;

$^1$H NMR (400 MHz, CDCl$_3$) δ 8.12 (d, J=7.2 Hz, 2H), 7.77 (d, J=7.2 Hz, 2H), 7.61 (t, J=7.4 Hz, 1H), 7.54-7.46 (m, 5H), 7.44-7.36 (m, 4H), 7.34 (d, J=7.3 Hz, 1H), 7.20 (d, J=8.8 Hz, 1H), 6.21 (t, J=8.7 Hz, 1H), 5.80 (dd, J=8.9, 2.4 Hz, 1H), 5.67 (d, J=6.9 Hz, 1H), 5.43 (dd, J=10.5, 7.4 Hz, 1H), 5.16 (s, 1H), 4.93 (d, J=8.7 Hz, 1H), 4.79 (dd, J=5.1, 2.7 Hz, 1H), 4.31 (d, J=8.4 Hz, 1H), 4.21 (d, J=8.4 Hz, 1H), 3.93 (d, J=6.8 Hz, 1H), 3.84 (d, J=5.2 Hz, 1H), 3.34 (s, 3H), 2.85 (d, J=3.1 Hz, 6H), 2.63-2.49 (m, 1H), 2.38 (s, 3H), 2.35-2.27 (m, 2H), 1.88 (s, 4H), 1.80 (s, 3H), 1.17 (d, J=5.6 Hz, 6H).

$^{13}$C NMR (101 MHz, CDCl$_3$) δ 206.21, 172.54, 171.18, 170.19, 166.97, 166.93, 155.03, 139.05, 138.17, 135.13, 133.78, 133.66, 131.85, 130.17, 129.25, 128.92, 128.69, 128.65, 128.21, 127.09, 126.92, 84.04, 82.76, 81.01, 78.68, 76.59, 74.70, 73.29, 72.77, 72.34, 56.84, 56.73, 54.94, 46.48, 43.14, 36.51, 35.88, 35.55, 34.00, 33.87, 29.69, 26.47, 25.58, 24.90, 22.58, 20.55, 14.43, 10.79.

Example 12

Preparation of PCMI-33

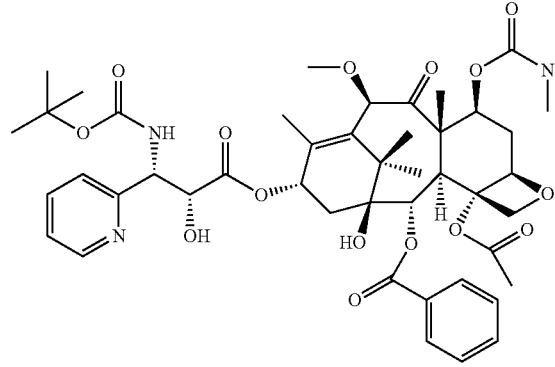

1) Preparation of (4S,5R)-3-t-butoxycarbonyl-2-(4-methoxyphenyl)-4-(2-pyridinyl)-5-oxazolidine carboxylic acid The specific method was seen in Step 1) in Example 3.

2) Preparation of 7-dimethylcarbamoyl-10-methoxy baccatin III

The specific method was seen in Step 2) in Example 10.

3) Preparation of PCMI-33

The specific method was seen in Step 3) in Example 1. The purity of the final product was 95% or higher.

PCMI-33: mp: 236-239° C.;

MS (m/z) ESI: 916.4 (M+Na)+;

$^1$H NMR (400 MHz, CDCl$_3$) δ 8.54 (dd, J=14.0, 4.6 Hz, 1H), 8.14-8.07 (m, 2H), 7.79-7.70 (m, 1H), 7.61 (t, J=7.4 Hz, 1H), 7.49 (t, J=7.8 Hz, 2H), 7.43-7.37 (m, 1H), 7.25 (d, J=9.4 Hz, 1H), 6.18 (t, J=8.9 Hz, 1H), 5.88 (d, J=9.6 Hz, 1H), 5.67 (d, J=7.1 Hz, 1H), 5.48 (dd, J=10.5, 7.4 Hz, 1H), 5.37 (d, J=8.9 Hz, 1H), 5.21 (s, 1H), 4.97 (d, J=8.2 Hz, 1H), 4.80 (d, J=2.6 Hz, 1H), 4.32 (d, J=8.3 Hz, 1H), 4.18 (d, J=8.3 Hz, 1H), 3.98 (d, J=7.0 Hz, 1H), 3.85 (d, J=5.3 Hz, 1H), 3.35 (s, 3H), 2.88-2.83 (d, 6H), 2.66-2.53 (m, 1H), 2.46 (s, 3H), 2.38-2.31 (m, 2H), 1.97 (s, 4H, H-6), 1.80 (s, 3H), 1.25 (s, 9H), 1.15 (d, J=5.6 Hz, 6H).

$^{13}$C NMR (101 MHz, CDCl$_3$) δ 206.43, 171.16, 170.28, 167.06, 158.81, 155.04, 148.51, 139.81, 137.51, 134.61, 133.65, 130.14, 130.07, 129.27, 128.66, 122.94, 121.82, 84.13, 82.72, 80.60, 80.20, 79.02, 74.89, 73.66, 72.75, 71.40, 56.09, 46.48, 43.15, 43.06, 36.53, 35.91, 35.47, 33.99, 31.93, 31.44, 29.70, 29.36, 28.29, 27.94, 26.25, 22.70, 22.18, 20.67, 14.38, 14.13, 10.79.

Example 13

Preparation of PCMI-34

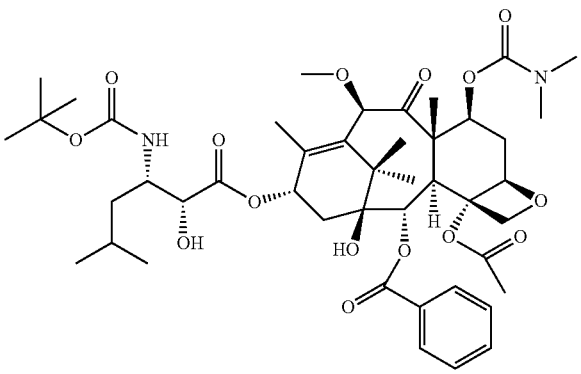

1) Preparation of (4S,5R)-3-t-butoxycarbonyl-2-(4-methoxyphenyl)-4-isobutyl-5-oxazolidine carboxylic acid The specific method was seen in Step 1) in Example 4.

2) Preparation of 7-dimethylcarbamoyl-10-methoxy baccatin III

The specific method was seen in Step 2) in Example 10.

3) Preparation of PCMI-34

The specific method was seen in Step 3) in Example 1. The purity of the final product was 95% or higher.

PCMI-34: mp: 229-231° C.;

MS (m/z) ESI: 895.4 (M+Na)+;

$^1$H NMR (400 MHz, CDCl$_3$) δ 8.12 (d, J=7.4 Hz, 2H), 7.61 (t, J=7.4 Hz, 1H), 7.48 (t, J=7.7 Hz, 2H), 6.19 (t, J=8.7 Hz, 1H), 5.68 (d, J=7.0 Hz, 1H), 5.47 (dd, J=10.5, 7.3 Hz, 1H), 5.22 (s, 1H), 4.97 (d, J=8.1 Hz, 1H), 4.67 (d, J=9.8 Hz, 1H), 4.32 (d, J=8.4 Hz, 1H), 4.26-4.14 (m, 3H), 3.97 (d, J=6.9 Hz, 1H), 3.38 (s, 3H), 3.34 (d, J=5.8 Hz, 1H), 2.86 (d, J=2.7 Hz, 6H), 2.57 (ddd, J=14.5, 9.4, 7.4 Hz, 1H), 2.40 (d, J=5.3 Hz, 5H), 2.02 (d, J=0.6 Hz, 3H), 1.92 (ddd, J=14.5, 10.9, 1.9 Hz, 1H), 1.81 (s, 3H), 1.69 (m, 1H), 1.33 (s, 1H), 1.19 (d, J=9.1 Hz, 6H), 0.99 (d, J=6.0 Hz, 6H).

$^{13}$C NMR (101 MHz, CDCl$_3$) δ 206.25, 173.76, 169.75, 166.93, 155.46, 155.05, 139.59, 134.86, 133.52, 130.18, 129.39, 128.60, 84.07, 82.81, 80.94, 79.57, 78.85, 76.53, 74.95, 73.02, 72.74, 72.65, 56.80, 56.68, 51.29, 46.49, 43.18, 41.26, 36.49, 35.86, 35.45, 33.97, 28.19, 26.23, 24.72, 23.27, 22.45, 21.91, 20.69, 14.43, 10.79.

Example 14

Preparation of PCMI-35

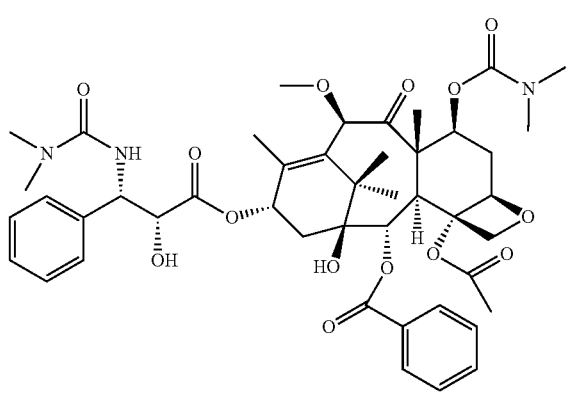

1) Preparation of (4S,5R)-3-dimethylcarbamoyl-2-(4-methoxyphenyl)-4-phenyl-5-oxazolidine carboxylic acid The specific method was seen in Step 1) in Example 8.

2) Preparation of 7-dimethylcarbamoyl-10-methoxy baccatin III

The specific method was seen in Step 2) in Example 10.

3) Preparation of PCMI-35

The specific method was seen in Step 3) in Example 1. The purity of the final product was 95% or higher.

PCMI-35: mp: 229-231° C.;

MS (m/z) ESI: 902.3 (M+K)$^+$;

$^1$H NMR (400 MHz, CDCl$_3$) δ 8.07-7.97 (m, 2H), 7.61 (t, J=7.4 Hz, 1H), 7.52-7.36 (m, 10H), 6.93 (d, J=8.7 Hz, 2H), 6.39 (s, 1H), 6.14 (s, 1H), 5.58 (d, J=7.1 Hz, 1H), 5.42 (s, 1H), 4.89 (d, J=8.7 Hz, 1H), 4.71 (s, 1H), 4.58 (d, J=4.9 Hz, 1H), 4.22 (d, J=8.4 Hz, 1H), 4.10 (d, J=8.4 Hz, 1H), 3.85-3.77 (m, 4H), 3.71 (d, J=7.1 Hz, 1H), 3.40 (s, 3H), 3.26 (s, 3H), 2.64 (ddd. J=14.4, 9.7, 6.4 Hz, 1H), 2.19 (dd, J=15.3, 9.1 Hz, 1H), 2.11-2.04 (m, 1H), 1.97-1.89 (m, 1H), 1.80 (s, 3H), 1.66 (s, 3H), 1.58 (s, 3H), 1.19 (s, 3H), 1.15 (s, 3H), 1.05 (s, 9H).

$^{13}$C NMR (101 MHz, CDCl$_3$) δ 204.87, 171.16, 169.91, 169.55, 166.88, 160.38, 156.99, 151.48, 139.05, 135.07, 133.68, 130.04, 129.29, 128.97, 128.68, 128.57, 128.17, 126.57, 113.87, 92.60, 84.09, 82.35, 81.23, 80.85, 80.56, 79.06, 76.27, 74.68, 71.83, 63.68, 57.10, 57.05, 56.70, 55.30, 49.12, 47.30, 43.18, 35.42, 33.88, 31.86, 29.68, 27.81, 26.65, 25.61, 24.93, 21.60, 20.89, 13.86, 10.34

Example 15

Preparation of PCMI-36

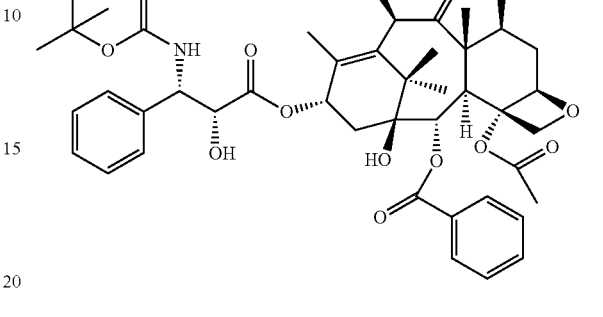

1) Preparation of (4S,5R)-3-t-butoxycarbonyl-2-(4-methoxyphenyl)-4-phenyl-5-oxazolidine carboxylic acid The specific method was seen in Example 1.

2) Preparation of 7-methoxyformyl-10-methoxy baccatin III

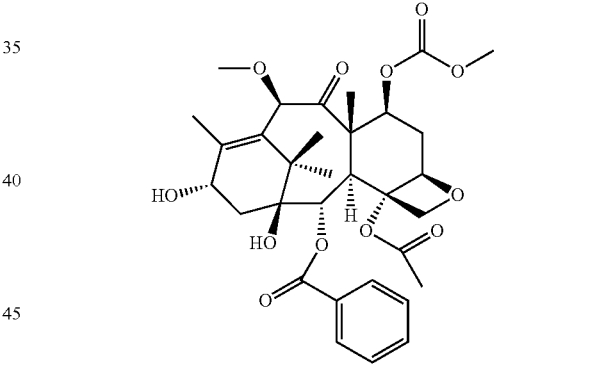

10-DAB (1 eq.) was used as raw material, dissolved in DMF and added successively with 2.5 equivalents of imidazole and 2.5 equivalents of triethyl chlorosilane. After post-treatment, the crude compound 1 as shown in the following reaction scheme was given.

The compound 1 (1 eq.) was dissolved in dichloromethane which was used as the solvent, into which 2 equivalents of pyridine was added at 0° C. Successively, the reaction liquid was added dropwise with 2 equivalents of p-toluenesulfonyl chloride. After 4 hours of reaction, by post-treatment of purification by column chromatography, the compound 14 was given in a yield of 90%.

The compound 14 (1 eq.) was dissolved in anhydrous tetrahydrofuran and reacted with methyl magnesium bromide (2 eq.) for 3 hours at room temperature under the protection of nitrogen. After post-treatment, the crude compound 15 was obtained after dried.

The compound 15 (1 eq.) was dissolved in dry THF, into which 1.5 equivalents of tetrabutylammonium fluoride (which is in the form of a solution in THF) was added at room temperature. After 1 hour of reaction, the reaction was completed. By post-treatment of purification by column chromatography, the compound 16 was given in a yield of 90%.

The compound 16 (1 eq.) was dissolved in a solvent dry THF, into which 1.5 equivalents LHMDS was added at 0° C. After 1 hour of reaction, 2 equivalents of methoxyformyl chloride was slowly added dropwise to the reaction liquid and reacted for 2 hours. By post-treatment of purification by column chromatography, the compound 18 was given in a yield of 71%.

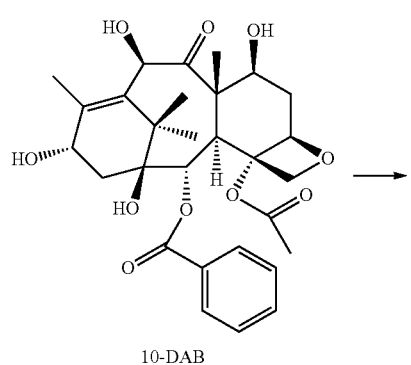

10-DAB

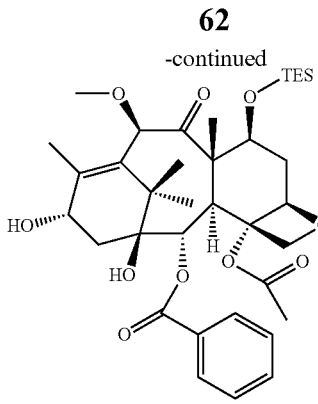

15

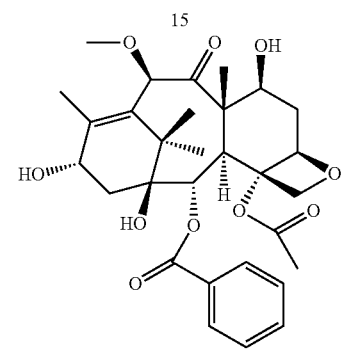

16

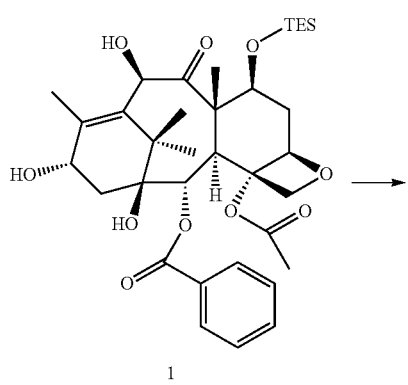

1

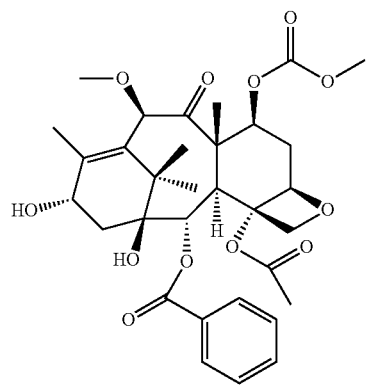

18

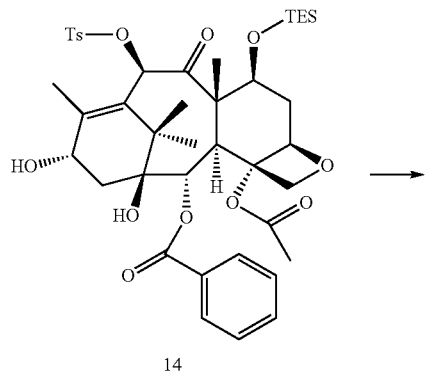

14

3) Preparation of PCMI-36

The specific method was seen in Step 3) in Example 1. The purity of the final product was 95% or higher.

PCMI-36: mp: 232-234° C.;
MS (m/z) ESI: 902.3 (M+Na)$^+$;
$^1$H NMR (400 MHz, DMSO) δ 8.00 (d, J=7.4 Hz, 2H), 7.71 (t, J=7.4 Hz, 1H), 7.63 (q, J=7.4 Hz, 2H), 7.47-7.28 (m, 5H), 7.21 (t, J=7.1 Hz, 1H), 5.92 (t, J=9.6 Hz, 2H), 5.46 (d, J=7.1 Hz 1H), 5.28 (dd, J=10.5, 7.4 Hz, 1H), 4.95 (t, J=11.3 Hz, 2H), 4.90 (s, 1H), 4.67 (s, 1H), 4.39 (t, J=7.1 Hz, 1H), 4.08 (s, 2H), 3.75 (d, J=7.0 Hz, 1H), 3.68 (s, 3H), 3.25 (s, 3H), 2.54-2.46 (m, 1H), 2.27 (s, 3H), 1.83 (s, 3H), 1.87-1.68 (m, 6H), 1.63 (s, 3H), 1.37 (s, 9H), 1.03 (s, 3H), 0.99 (s, 3H).
$^{13}$C NMR (101 MHz, DMSO) δ 205.78, 173.22, 170.65, 165.68, 155.56, 154.87, 140.02, 138.98, 135.26, 133.88, 130.17, 129.12, 128.61, 127.68, 83.21, 82.77, 80.15, 79.73, 79.40, 79.07, 78.58, 77.33, 76.22, 75.82, 74.78, 74.38, 70.24, 60.18, 57.76, 57.18, 56.04, 55.57, 46.27, 43.25, 35.30, 33.82, 33.36, 28.61, 26.67, 24.93, 22.79, 21.48, 21.17, 14.42, 10.85.

Example 16

Preparation of PCMI-37

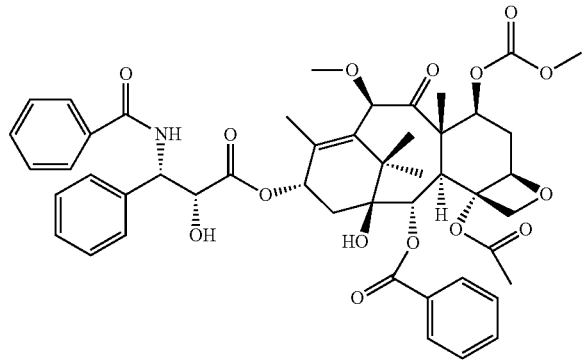

1) Preparation of (4S,5R)-3-benzoyl-2-(4-methoxyphenyl)-4-phenyl-5-oxazolidine carboxylic acid The specific method was seen in Step 1) in Example 2.

2) Preparation of 7-methoxyformyl-10-methoxy baccatin III

The specific method was seen in Step 2) in Example 15.

3) Preparation of PCMI-37

The specific method was seen in Step 3) in Example 1. The purity of the final product was 95% or higher.

PCMI-37: mp: 222-224° C.;
MS (m/z) ESI: 906.4 (M+Na)$^+$;
$^1$H NMR (400 MHz, CDCl$_3$) δ 8.16-8.09 (m, 2H), 7.80-7.73 (m, 2H), 7.63 (t, J=7.4 Hz, 1H), 7.56-7.46 (m, 5H), 7.46-7.32 (m, 5H), 7.16 (d, J=8.9 Hz, 1H), 6.22 (t, J=8.6 Hz, 1H), 5.81 (dd, J=8.9, 2.5 Hz, 1H), 5.69 (d, J=7.0 Hz, 1H), 5.36 (dd, J=10.5, 7.4 Hz, 1H), 5.11 (s, 1H), 4.94 (d, J=8.3 Hz, 1H), 4.80 (dd, J=5.3, 2.8 Hz, 1H), 4.33 (d, J=8.4 Hz, 1H), 4.21 (d, J=8.5 Hz, 1H), 3.93 (d, J=6.8 Hz, 1H), 3.80-3.73 (m, 4H), 3.38 (s, 3H), 2.59 (m, 1H), 2.40 (s, 3H), 2.32 (dd, J=8.9, 3.3 Hz, 2H), 2.05-1.96 (m, 1H), 1.87 (s, 3H), 1.81 (s, 3H), 1.18 (d, J=7.7 Hz, 6H).
$^{13}$C NMR (101 MHz, CDCl$_3$) δ 205.31, 172.62, 170.47, 166.99, 154.99, 139.01, 138.02, 135.17, 133.71, 131.95, 130.19, 129.07, 128.72, 128.31, 127.08, 83.68, 82.62, 80.85, 78.74, 76.56, 76.06, 74.56, 73.27, 72.37, 56.92, 56.61, 55.23, 55.03, 46.44, 43.08, 35.54, 33.44, 26.45, 22.58, 20.66, 14.28, 10.66.

Example 17

Preparation of PCMI-38

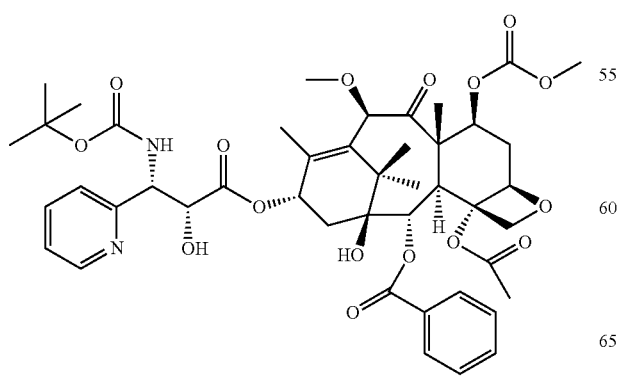

1) Preparation of (4S,5R)-3-t-butoxycarbonyl-2-(4-methoxyphenyl)-4-(2-pyridinyl)-5-oxazolidine carboxylic acid The specific method was seen in Step 1) in Example 3.

2) Preparation of 7-methoxyformyl-10-methoxy baccatin III

The specific method was seen in Step 2) in Example 15.

3) Preparation of PCMI-38

The specific method was seen in Step 3) in Example 1. The purity of the final product was 95% or higher.

PCMI-38: mp: 235-237° C.;
MS (m/z) ESI: 903.4 (M+Na)$^+$;
$^1$H NMR (400 MHz, CDCl$_3$) δ 8.53 (d, J=4.4 Hz, 1H), 8.12 (d, J=7.2 Hz, 2H), 7.78 (td, J=7.7, 1.6 Hz, 1H), 7.63 (t, J=7.4 Hz, 1H), 7.51 (t, J=7.7 Hz, 2H), 7.44 (d, J=7.9 Hz, 1H), 7.31-7.26 (m, 1H), 6.20 (t, J=8.8 Hz, 1H), 5.88 (d, J=9.9 Hz, 1H), 5.70 (d, J=7.0 Hz, 1H), 5.47-5.36 (m, 2H), 5.17 (s, 1H), 4.98 (d, J=8.1 Hz, 1H), 4.82 (s, 1H), 4.35 (d, J=8.4 Hz, 1H), 4.20 (d, J=8.4 Hz, 1H), 3.99 (d, J=7.0 Hz, 1H), 3.77 (s, 3H), 3.39 (s, 3H), 2.68-2.56 (m, 1H), 2.50 (s, 3H), 2.31 (dd, J=14.3, 8.9 Hz, 2H), 2.06-1.93 (m, 4H), 1.82 (s, 3H), 1.46 (s, 9H), 1.19 (d, J=6.1 Hz, 6H).
$^{13}$C NMR (101 MHz, CDCl$_3$) δ 205.49, 170.61, 167.01, 154.97, 148.46, 139.76, 137.57, 134.71, 133.70, 130.14, 129.20, 128.69, 122.97, 121.89, 83.77, 82.59, 80.51, 79.03, 76.08, 74.73, 71.33, 56.87, 56.61, 55.18, 54.38, 54.32, 46.47, 43.09, 35.47, 33.45, 31.93, 31.44, 30.19, 29.70, 29.37, 28.30, 26.24, 22.70, 22.18, 20.74, 14.35, 14.13, 10.64.

Example 18

Preparation of PCMI-39

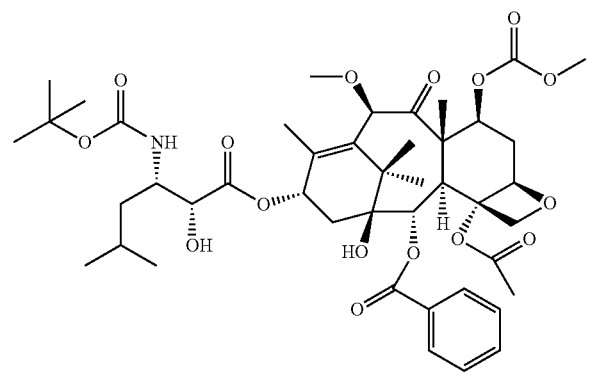

1) Preparation of (4S,5R)-3-t-butoxycarbonyl-2-(4-methoxy phenyl)-4-isobutyl-5-oxazolidine carboxylic acid The specific method was seen in Step 1) in Example 4.

2) Preparation of 7-methoxyformyl-10-methoxy baccatin III

The specific method was seen in Step 2) in Example 15.

3) Preparation of PCMI-39

The specific method was seen in Step 3) in Example 1. The purity of the final product was 95% or higher.

PCMI-39: mp: 237-239° C.;

MS (m/z) ESI: 882.4 (M+Na)$^+$;

$^1$H NMR (400 MHz, CDCl$_3$) δ 8.11 (d, J=7.5 Hz, 2H), 7.61 (t, J=7.4 Hz, 1H), 7.48 (t, J=7.7 Hz, 2H), 6.19 (t, J=8.8 Hz, 1H), 5.68 (d, J=7.0 Hz, 1H), 5.38 (dd, J=10.6, 7.4 Hz, 1H), 5.15 (s, 1H), 4.95 (d, J=8.2 Hz, 1H), 4.60 (d, J=9.7 Hz, 1H), 4.32 (d, J=8.5 Hz, 1H), 4.26-4.13 (m, 3H), 3.95 (d, J=6.9 Hz, 1H), 3.75 (s, 3H), 3.39 (s, 3H), 3.25 (d, J=5.9 Hz, 1H), 2.68-2.52 (m, 1H), 2.39 (s, 5H), 1.99 (s, 4H), 1.80 (s, 3H), 1.69 (dd, J=17.2, 7.1 Hz, 2H), 1.33 (s, 10H), 1.20 (s, 3H), 1.17 (s, 3H), 1.02-0.95 (m, 6H).

$^{13}$C NMR (101 MHz, CDCl$_3$) δ 205.35, 173.90, 170.06, 166.91, 155.00, 130.21, 128.66, 83.70, 82.65, 80.80, 78.86, 76.02, 74.75, 73.02, 72.72, 56.85, 56.59, 55.20, 51.31, 46.43, 43.13, 41.23, 33.44, 29.71, 28.19, 26.18, 24.72, 23.29, 22.49, 21.92, 20.77, 14.40, 10.68.

Example 19

Preparation of PCMI-40

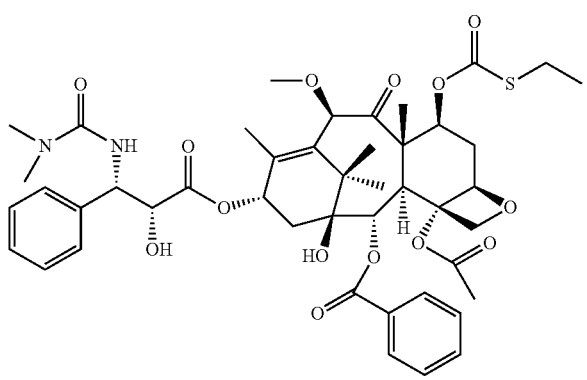

1) Preparation of (4S,5R)-3-dimethylcarbamoyl-2-(4-methoxyphenyl)-4-phenyl-5-oxazolidine carboxylic acid The specific method was seen in Step 1) in Example 8.

2) Preparation of 7-ethylthioformyl-10-methoxy baccatin III

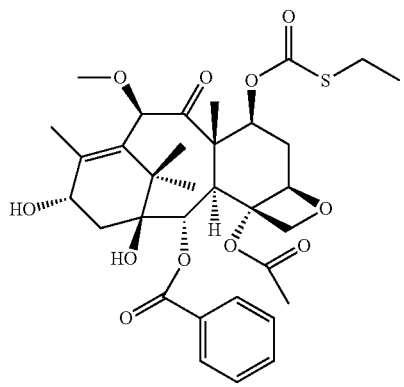

10-DAB (1 eq.) was used as raw material, dissolved in DMF and added successively with 2.5 equivalents of imidazole and 2.5 equivalents of triethyl chlorosilane. After post-treatment, the crude compound 1 was given.

The compound 1 was dissolved in dichloromethane which was used as the solvent, into which 2 equivalents of pyridine was added at 0° C. Successively, the reaction liquid was added dropwise with 2 equivalents of p-toluenesulfonyl chloride. After 4 hours of reaction, by post-treatment of purification by column chromatography, the compound 14 was given in a yield of 90%.

The compound 14 (1 eq.) was dissolved in anhydrous tetrahydrofuran and reacted with methyl magnesium bromide (2 eq.) for 3 hours at room temperature under the protection of nitrogen. After post-treatment, the crude compound 15 was obtained by dried.

The compound 15 (1 eq.) was dissolved in dry THF, into which 1.5 equivalents of tetrabutylammonium fluoride (which is in the form of a solution in THF) was added at room temperature. After 1 hours of reaction, the reaction was completed. By post-treatment of purification by column chromatography, the compound 16 was given in a yield of 90%.

The compound 16 (1 eq.) was dissolved in dry THF which was used as the solvent and firstly reacted with 2 equivalents of N,N'-carbonyldiimidazole for 2 hours. The reaction liquid was then added with 2 equivalents of ethanethiol. After 4 hours of reaction, by post-treatment of purification by column chromatography, the compound 19 was given in a yield of 78%.

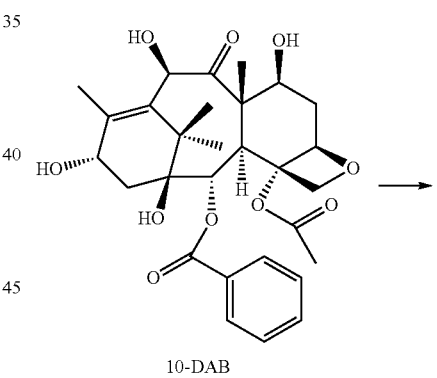

10-DAB

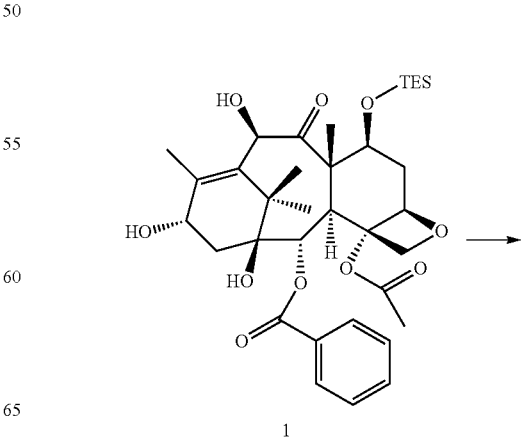

1

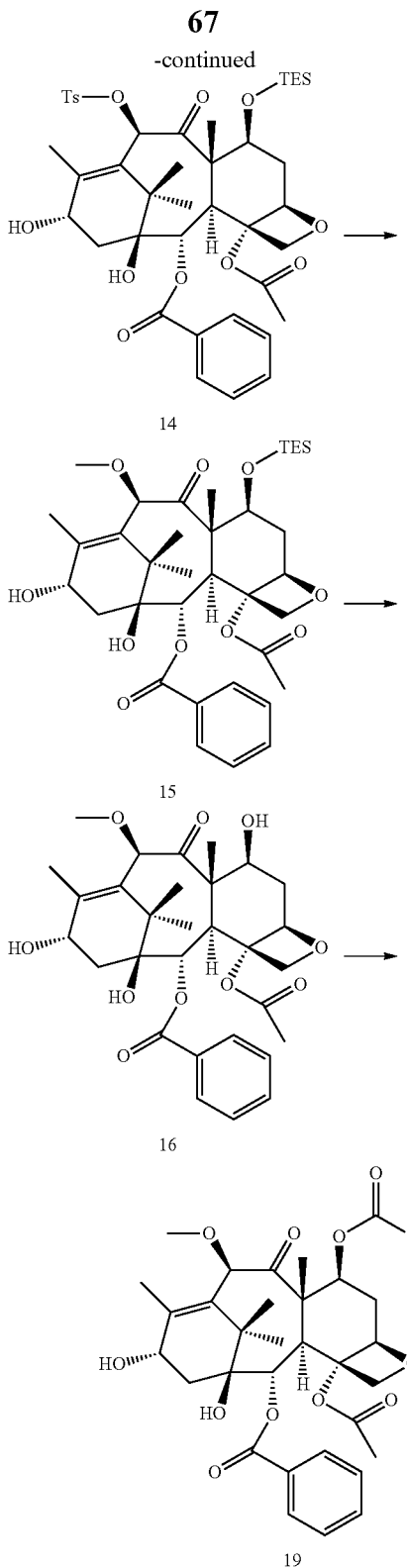

3) Preparation of PCMI-40

The specific method was seen in Step 3) in Example 1. The purity of the final product was 95% or higher.

PCMI-40: mp: 241-242° C.;
MS (m/z) ESI: 882.4 (M+H)+;

$^1$H NMR (400 MHz, CDCl$_3$) δ 8.08-8.00 (m, 2H), 7.64 (t, J=7.5 Hz, 1H), 7.50 (t, J=7.8 Hz, 2H), 6.11 (d, J=7.2 Hz, 1H), 5.41 (dd, J=10.7, 7.2 Hz, 1H), 5.19 (s, 1H), 5.06 (t, J=5.0 Hz, 1H), 5.00-4.93 (m, 1H), 4.82 (d, J=5.8 Hz, 1H), 4.34 (d, J=8.4 Hz, 1H), 4.23 (d, J=8.6 Hz, 1H), 3.88 (d, J=7.1 Hz, 1H), 3.77 (s, 3H), 3.43 (s, 3H), 3.36 (d, J=5.5 Hz, 1H), 2.60 (ddd, J=14.5, 9.5, 7.2 Hz, 1H), 2.34 (s, 3H), 2.17 (d, J=1.1 Hz, 3H), 2.06-1.98 (m, 1H), 1.83 (s, 3H), 1.26 (s, 3H), 1.16 (s, 3H).

$^{13}$C NMR (101 MHz, CDCl$_3$) δ 204.92, 170.54, 164.78, 155.00, 152.90, 141.17, 134.24, 129.85, 128.96, 128.07, 88.53, 84.18, 83.50, 82.74, 80.01, 76.01, 75.52, 71.84, 69.37, 57.32, 56.86, 55.29, 46.16, 41.28, 33.24, 25.61, 22.24, 21.41, 14.82, 10.74.

Example 20

Preparation of PCMI-41

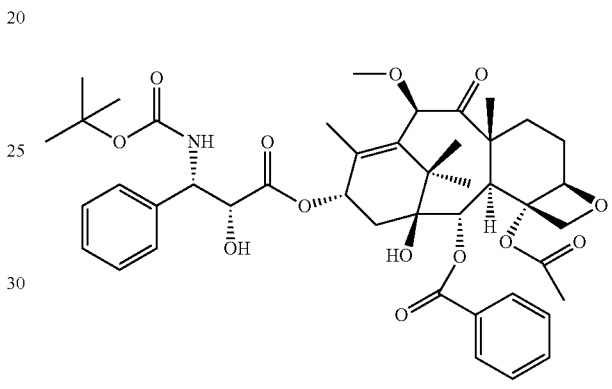

1) Preparation of (4S,5R)-3-t-butoxycarbonyl-2-(4-methoxyphenyl)-4-phenyl-5-oxazolidine carboxylic acid The specific method was seen in Example 1.

2) Preparation of 10-methoxy-7-dihydrobaccatin III

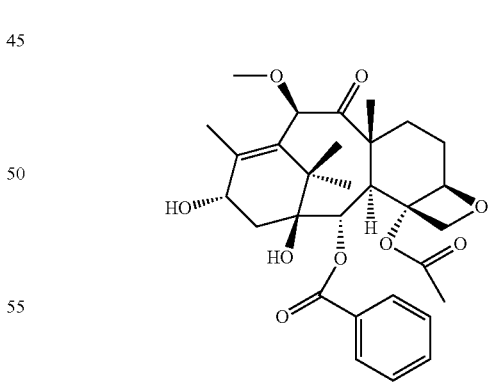

10-DAB (1 eq.) was used as raw material, dissolved in DMF and added successively with 2.5 equivalents of imidazole and 2.5 equivalents of triethyl chlorosilane. After post-treatment, the crude compound 1 as shown in the following reaction scheme was given.

The compound 1 was dissolved in dichloromethane which was used as the solvent, into which 2 equivalents of pyridine was added at 0° C. Successively, the reaction liquid was added dropwise with 2 equivalents of p-toluenesulfonyl chloride. After 4 hours of reaction, by post-treatment of purification by column chromatography, the compound 14 was given in a yield of 90%.

The compound 14 (1 eq.) was dissolved in anhydrous tetrahydrofuran and reacted with methyl magnesium bromide (2 eq.) for 3 hours at room temperature under the protection of nitrogen. After post-treatment, the crude compound 15 was obtained by dried.

The compound 15 (1 eq.) was dissolved in dry THF, into which 1.5 equivalents of tetrabutylammonium fluoride (which is in the form of a solution in THF) was added at room temperature. After 1 hour of reaction, the reaction was completed. By post-treatment of purification by column chromatography, the compound 16 was given in a yield of 92%.

The compound 16 (1 eq.) was dissolved in dry THF solution and the reaction liquid was added with 6 equivalents of N,N'-thiocarbonyldiimidazole. After 2 hours of reaction, the reaction was completed. By post-treatment of purification by column chromatography, the compound 21 was given in a yield of 86%.

The compound 21 (1 eq.) was dissolved in a solution of dioxane/tetrahydrofuran (10:1). 0.2 equivalents of azobisisobutyronitrile were added as a catalyst to induce free radical reaction at 100'C. Afterward, the reaction liquid was added with 4 equivalents of n-butyl tin hydride and after 1 hour of reaction, cooled overnight at room temperature. After purification by column chromatography, the compound 22 was given in a yield of 52%.

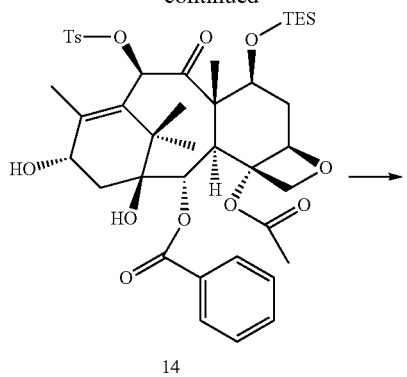

14

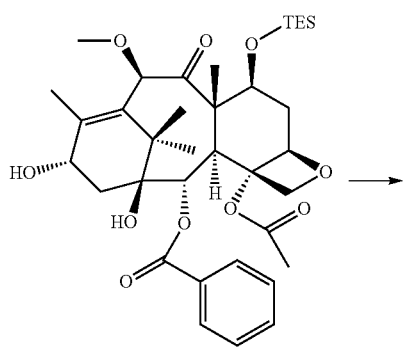

15

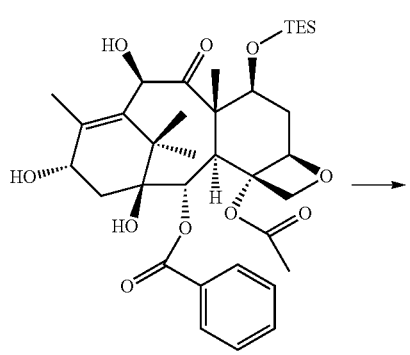

10-DAB

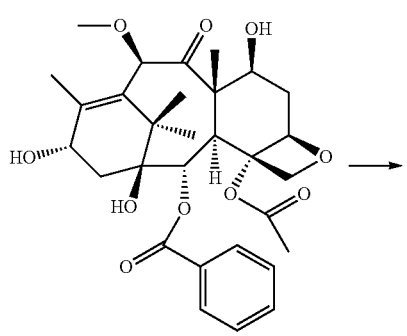

16

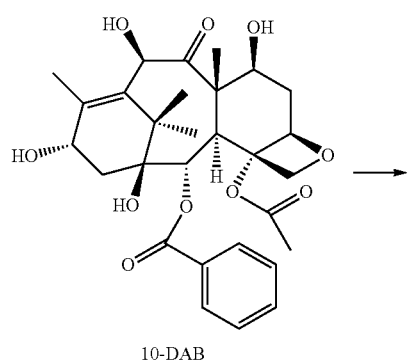

1

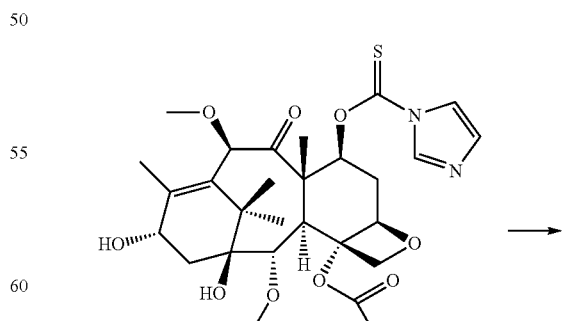

21

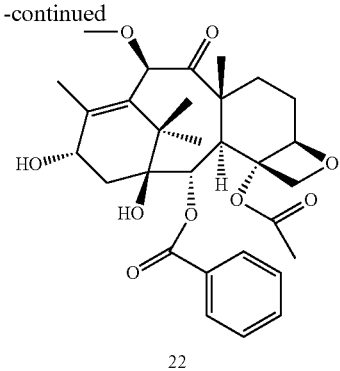

22

3) Preparation of PCMI-41

The specific method was seen in Step 3) in Example 1. The purity of the final product was 95% or higher.

PCMI-41: mp: 217-219° C.;
MS (m/z) ESI: 844.2 (M+K)$^+$;
IR: 3384, 2977, 2927, 2850, 1712, 1627, 1367, 1313, 1269, 1245, 1170, 1097, 987, 711.
$^1$H NMR (400 MHz, CDCl$_3$) δ 8.13 (d, J=7.4 Hz, 2H), 7.61 (t, J=7.4 Hz, 1H), 7.50 (t, J=7.6 Hz, 3H), 7.39 (q, J=7.9 Hz, 4H), 7.35-7.29 (m, 1H), 6.27 (t, J=8.7 Hz, 1H), 5.66 (d, J=7.4 Hz, 1H), 5.41 (d, J=9.4 Hz, 1H), 5.29 (s, 1H), 4.98-4.88 (n, 2H), 4.61 (s, 1H), 4.31 (d, J=8.4 Hz, 1H), 4.21 (d, J=8.4 Hz, 1H), 3.77 (d, J=7.3 Hz, 1H), 3.42 (d, J=8.2 Hz, 4H), 2.32 (m, 4H), 2.23 (dd, J=13.3, 9.4 Hz, 1H), 2.04-1.93 (m, 1H), 1.87 (s, 3H), 1.75 (s, 3H), 1.60-1.52 (m, 1H), 1.32 (s, 9H), 1.22 (s, 3H), 1.16 (s, 3H).
$^{13}$C NMR (101 MHz. CDCl$_3$) δ 209.18, 171.19, 170.14, 167.23, 155.31, 139.05, 138.44, 134.72, 133.59, 130.23, 129.36, 128.85, 128.67, 128.05, 126.72, 84.46, 82.27, 81.39, 80.19, 79.02, 75.85, 73.75, 72.43, 56.49, 53.08, 45.22, 43.02, 35.58, 29.70, 28.17, 27.20, 26.09, 22.74, 20.87, 14.82.

Example 21

Preparation of PCMI-42

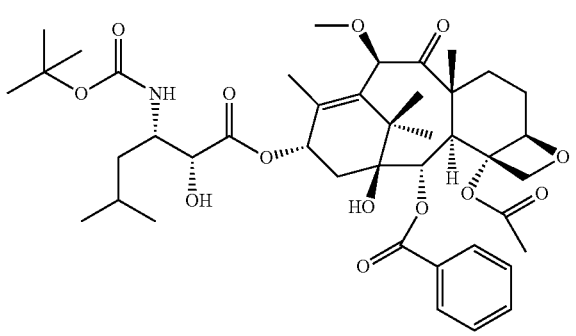

1) Preparation of (4S,5R)-3-t-butoxycarbonyl-2-(4-methoxyphenyl)-4-isobutyl-5-oxazolidine carboxylic acid The specific method was seen in Step 1) in Example 4.

2) Preparation of 10-methoxy-7-dihydrobaccatin III

The specific method was seen in Step 2) in Example 20.

3) Preparation of PCMI-42

The specific method was seen in Step 3) in Example 1. The purity of the final product was 95% or higher.

PCMI-42: mp: 213-215° C.;
MS (m/z) ESI: 808.4 (M+Na)$^+$;
$^1$H NMR (400 MHz, CDCl$_3$) δ 8.14 (d, J=7.4 Hz, 2H), 7.60 (t, J=7.4 Hz, 1H), 7.47 (t, J=7.7 Hz, 2H), 6.21 (dd, J=9.1, 7.9 Hz, 1H), 5.66 (d, J=7.4 Hz, 1H), 5.00-4.90 (m, 2H), 4.62 (d, J=9.8 Hz, 1H), 4.31 (d, J=8.5 Hz, 1H), 4.25 (d, J=8.4 Hz, 1H), 4.18 (d, J=5.6 Hz, 1H), 4.14 (m, 1H), 3.79 (d, J=7.7 Hz, 1H), 3.43 (s, 3H), 3.29 (d, J=6.1 Hz, 1H), 2.49-2.31 (m, 5H), 2.29-2.18 (m, 1H), 2.04-1.93 (m, 1H), 1.91 (d, J=0.9 Hz, 3H), 1.76 (s, 3H), 1.72-1.64 (m, 1H), 1.62-1.50 (m, 1H), 1.48-1.36 (m, 2H), 1.31 (s, 9H), 1.20 (s, 3H), 1.16 (s, 3H), 0.99 (d, J=6.4 Hz, 6H).
$^{13}$C NMR (101 MHz, CDCl$_3$) δ 209.29, 173.95, 169.98, 167.13, 155.44, 139.36, 134.55, 133.50, 130.24, 129.50, 128.62, 84.45, 82.23, 81.41, 79.65, 79.07, 75.96, 73.05, 72.67, 56.44, 53.03, 51.26, 45.21, 42.98, 41.28, 35.68, 29.70, 28.17, 27.20, 25.92, 24.71, 23.27, 22.63, 21.92, 20.89, 14.89, 14.28.

Example 22

Preparation of PCMI-43

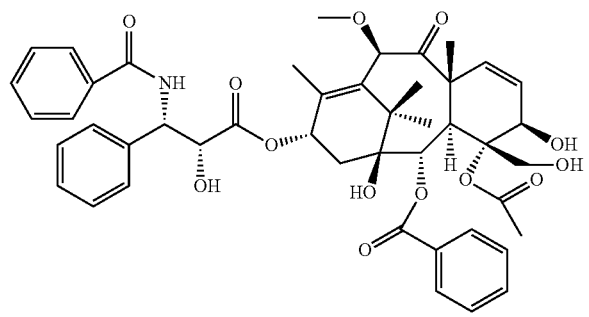

1) Preparation of (4S,5R)-3-benzoyl-2-(4-methoxy phenyl)-4-phenyl-5-oxazolidine carboxylic acid The specific method was seen in Step 1) in Example 2.

2) Preparation of 10-methoxy-6,7-double-bond baccatin III

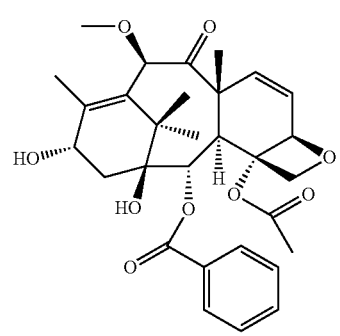

10-DAB (1 eq.) was used as raw material, dissolved in DMF and added successively with 2.5 equivalents of imidazole and 2.5 equivalents of triethyl chlorosilane. After post-treatment, the crude compound 1 was given.

The compound 1 was dissolved in dichloromethane which was used as the solvent, into which 2 equivalents of pyridine was added at 0° C. Successively, the reaction liquid was added dropwise with 2 equivalents of p-toluenesulfonyl chloride. After 4 hours of reaction, by post-treatment of purification by column chromatography, the compound 14 was given in a yield of 90%.

The compound 14 (1 eq.) was dissolved in anhydrous tetrahydrofuran and reacted with methyl magnesium bromide (2 eq.) for 3 hours at room temperature under the protection of nitrogen. After post-treatment, the crude compound 15 was obtained by dried.

The compound 15 (1 eq.) was dissolved in dry THF, into which 1.5 equivalents of tetrabutylammonium fluoride (which is in the form of a solution in THF) was added at room temperature. After 1 hour of reaction, the reaction was completed. By post-treatment of purification by column chromatography, the compound 16 was given in a yield of 92%.

The compound 16 (1 eq.) was dissolved in dry dichloromethane. The reaction liquid was firstly added with 2 equivalents of pyridine in an ice bath and then was added dropwise with 2 equivalents of trifluoromethanesulfonic anhydride. After 2 hours of reaction, by post-treatment of purification by column chromatography, the compound 23 was given in a yield of 78%.

The compound 23 (1 eq.) was dissolved in a solution of dioxane/tetrahydrofuran (10:1). 2 equivalents of DBU was added at 100° C. and the elimination reaction of the sulfonate was performed for 0.5 hours. By post-treatment of purification by column chromatography, the compound 24 was given in a yield of 64%.

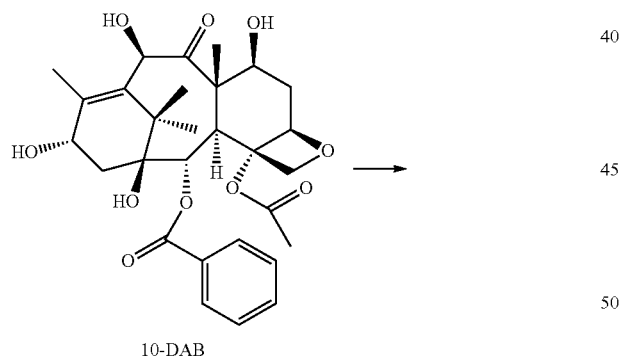

10-DAB

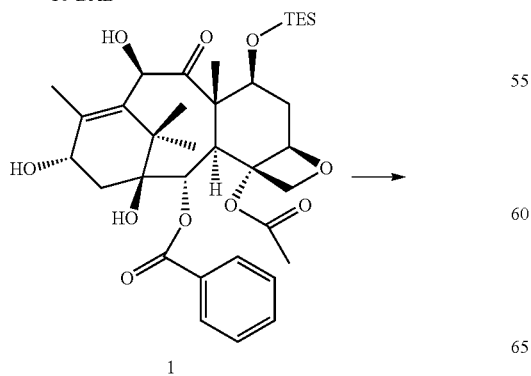

1

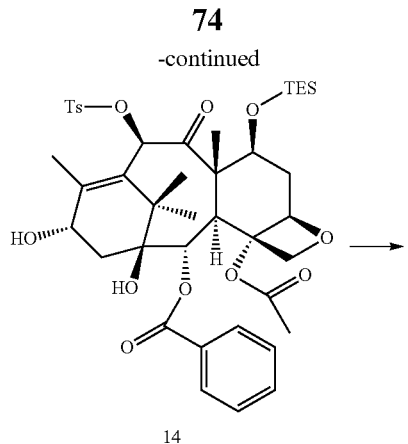

14

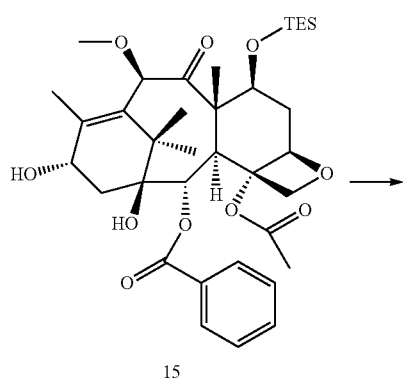

15

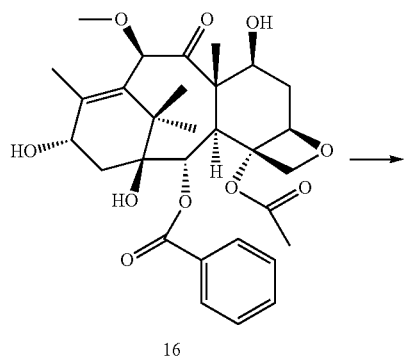

16

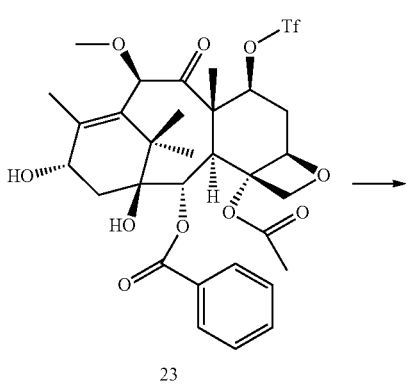

23

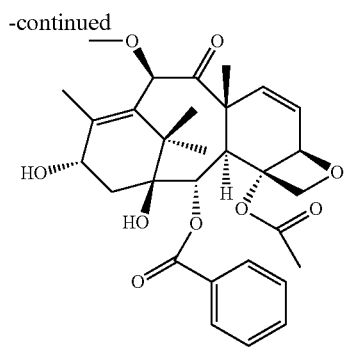

24

3) Preparation of PCMI-43

The specific method was seen in Step 3) in Example 1. The purity of the final product was 95% or higher.

PCMI-43: mp: 198-200° C.;

MS (m/z) ESI: 848.4 (M+Na)$^+$;

$^1$H NMR (400 MHz, CDCl$_3$) δ 8.12 (d, J=7.3 Hz, 2H), 7.81-7.75 (m, 2H), 7.58-7.47 (m, 4H), 7.47-7.32 (m, 5H), 7.26 (t, J=7.9 Hz, 2H), 7.11 (d, J=9.6 Hz, 1H), 6.17 (t, J=7.6 Hz, 1H), 6.08 (d, J=9.6 Hz, 1H), 5.94-5.86 (m, 2H), 5.52 (dd, J=10.6, 7.9 Hz, 2H), 4.80 (dd, J=3.2, 1.6 Hz, 1H), 4.72 (s, 1H), 4.44 (s, 1H), 4.25 (d, J=5.5 Hz, 1H), 3.71 (d, J=3.1 Hz, 1H), 3.50 (s, 3H), 3.42 (d, J=10.3 Hz, 1H), 3.25 (t, J=10.7 Hz, 1H), 3.05 (dd, J=15.4, 7.5 Hz, 1H), 2.47 (d, J=10.6 Hz, 1H), 2.15 (s, 3H), 2.13 (s, 3H), 1.52 (s, 3H), 1.24 (s, 3H), 1.18 (s, 3H).

Example 23

Preparation of PCMI-44

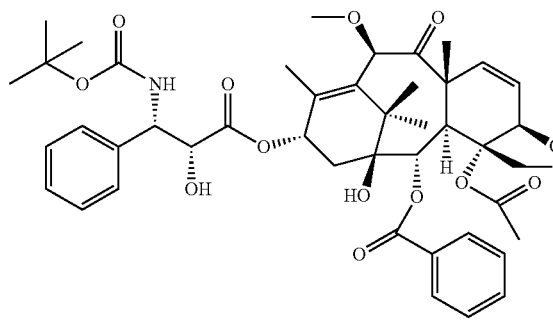

1) Preparation of (4S,5R)-3-t-butoxycarbonyl-2-(4-methoxyphenyl)-4-phenyl-5-oxazolidine carboxylic acid The specific method was seen in Example 1.

2) Preparation of 10-methoxy-6,7-double-bond baccatin III

The specific method was seen in Example 22.

3) Preparation of PCMI-44

The specific method was seen in Step 3) in Example 1. The purity of the final product was 95% or higher.

PCMI-44: mp: 186-187° C.;

MS (m/z) ESI: 844.4 (M+Na)$^+$;

$^1$H NMR (400 MHz, CDCl$_3$) δ 8.24 (t. 2H), 7.61 (t, 1H), 7.42 (m, 7H), 6.25 (t, J=7.9 Hz, 1H), 5.88 (d, 2H), 5.54 (d, 2H), 5.40 (d, 1H), 4.72 (s, 1H), 4.58 (d, J=2.6 Hz, 1H), 4.31 (d, 1H), 3.47 (d, 4H), 3.30 (t, 1H), 3.00 (d, 1H), 2.41-2.34 (m, 1H), 2.07 (s, 3H), 1.51 (s, 3H), 1.35 (s, 9H), 1.28 (s, 3H), 1.23 (s, 3H), 1.18 (s, 3H).

What is claimed is:

1. A taxane compound having the structure represented by the following formula I:

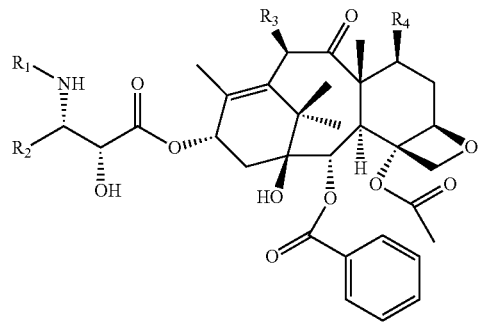

wherein,

R$_1$ is benzoyl, t-butyloxycarbonyl or N,N'-dimethylcarbamoyl;

R$_2$ is phenyl,

![2-pyridyl or isobutyl structures]

and either:

a. R$_3$ is —OMe, —OCOOCH$_3$, —OCON(CH$_3$)$_2$ or —OCOSC$_2$H$_5$; R$_4$ is —OCOOCH$_3$, —OCON(CH$_3$)$_2$, —OCOSC$_2$H$_5$ or H or b. R$_3$ is —OCOOCH$_3$, —OCON(CH$_3$)$_2$ or —OCOSC$_2$H$_5$; R$_4$ is —OMe, —OCOOCH$_3$, —OCON(CH$_3$)$_2$, —OCOSC$_2$H$_5$ or H.

2. The taxane compound according to claim 1, wherein the compound is selected from the compounds having the following structures:

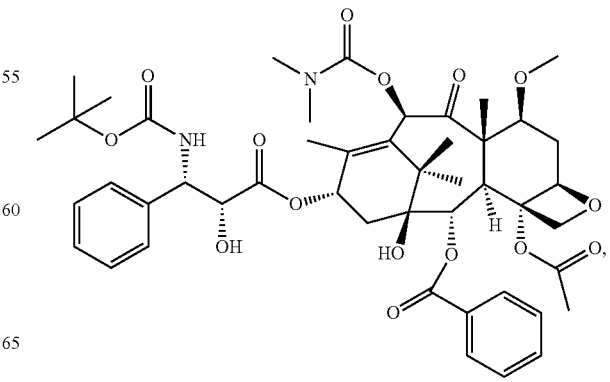

77
-continued
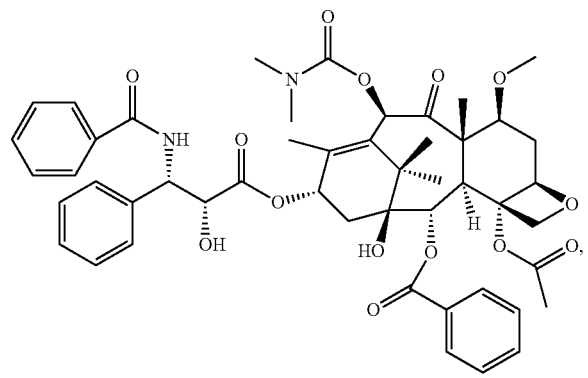
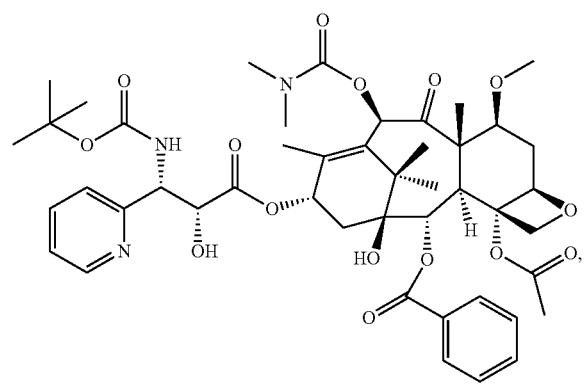
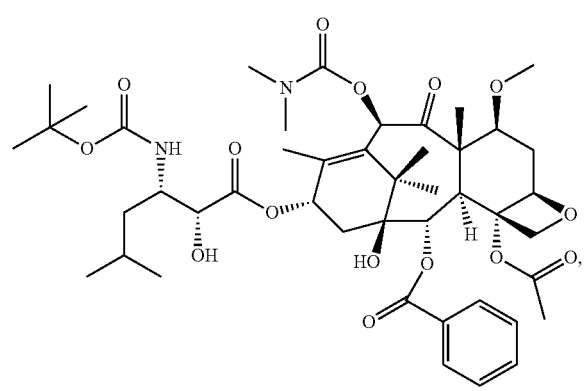
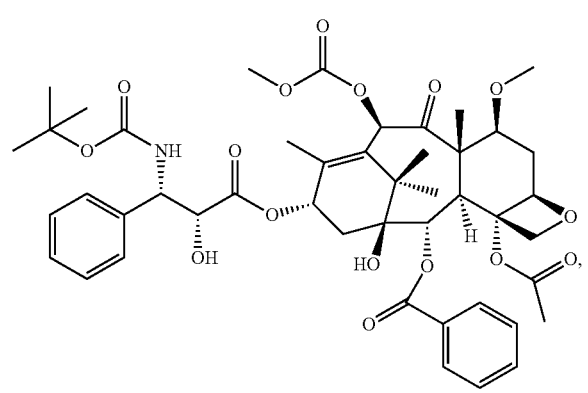
78
-continued
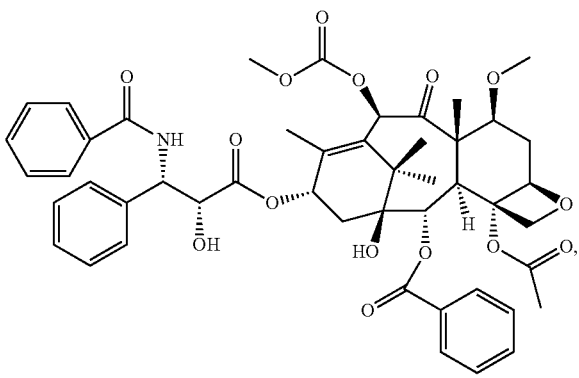
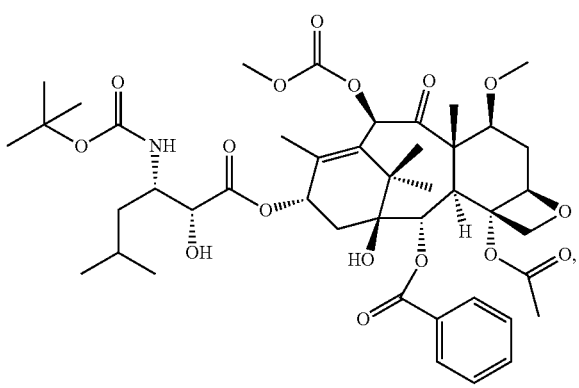
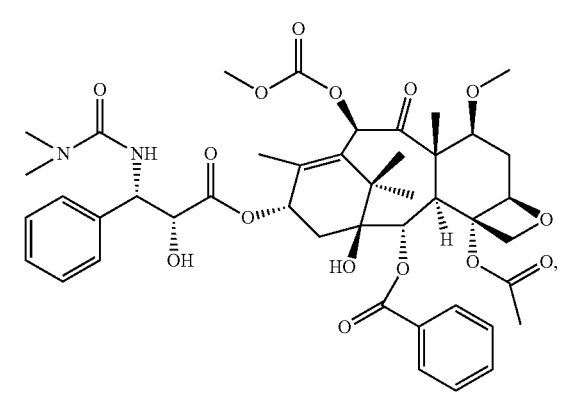
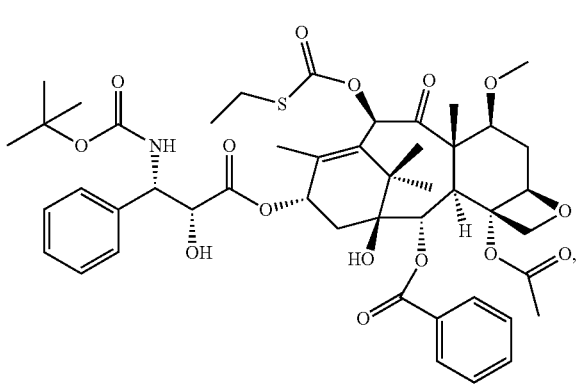

79
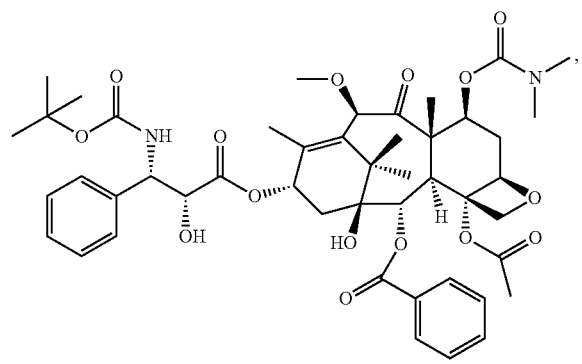
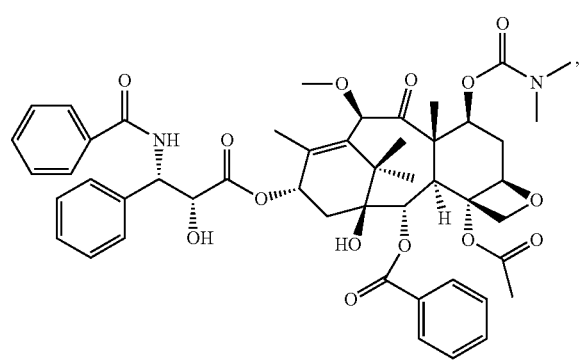
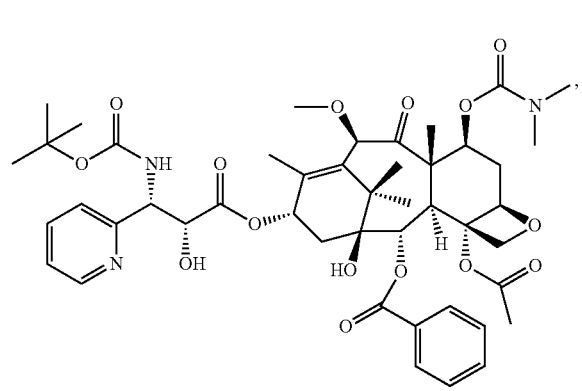
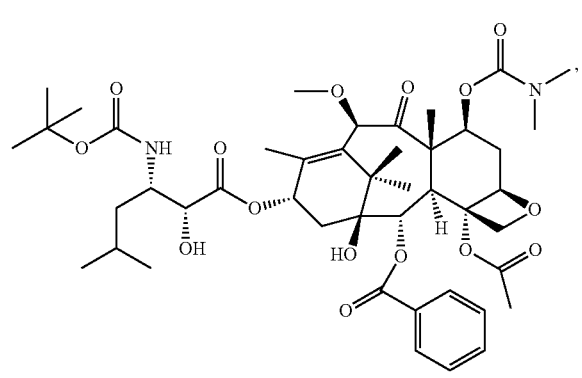
80
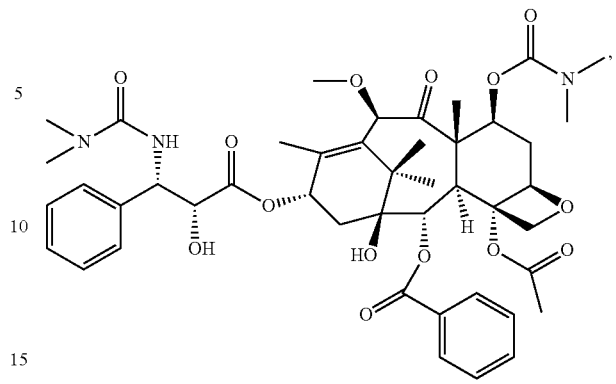
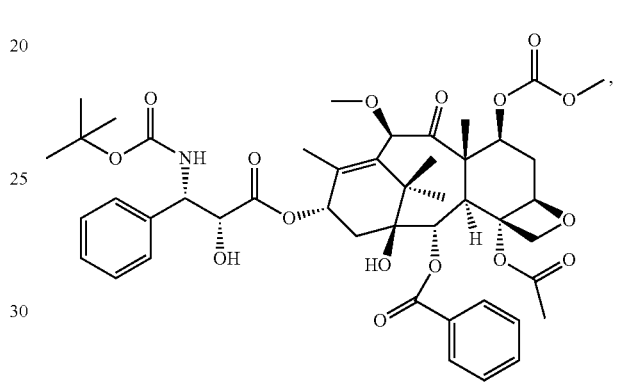
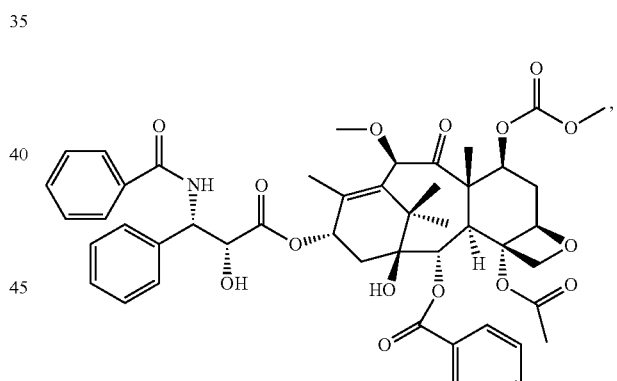
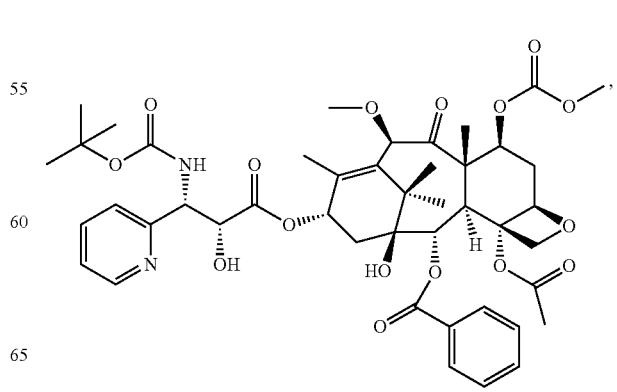

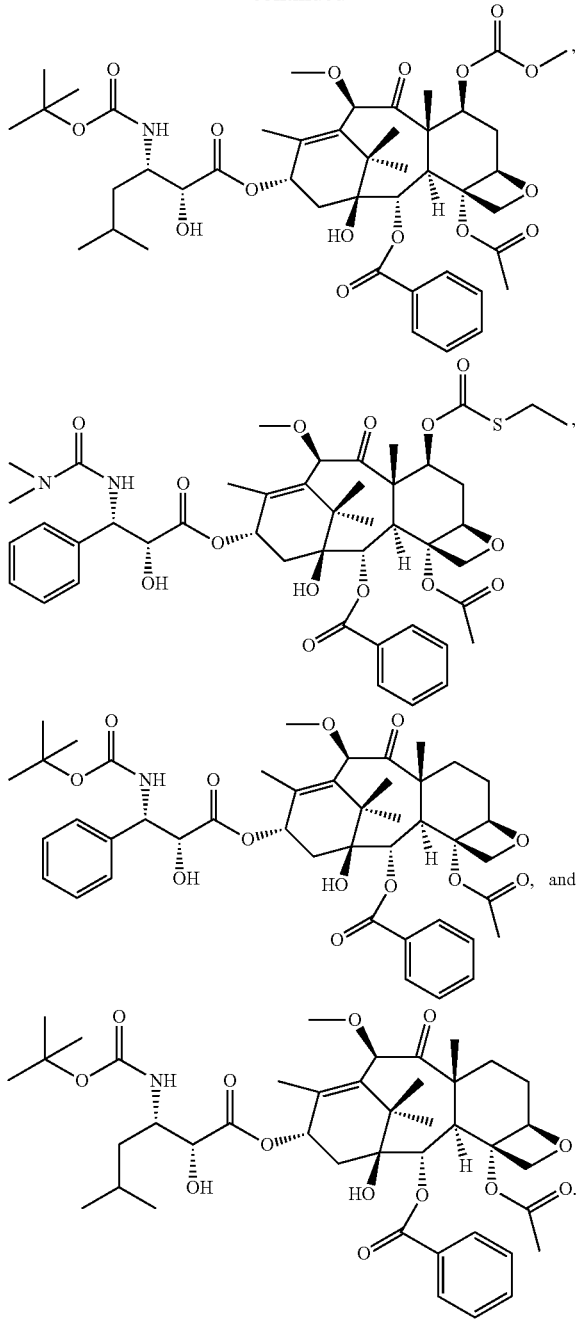

3. The taxane compound according to claim 1, wherein the taxane compound is formed into a pharmaceutically acceptable non-toxic salt.

4. The taxane compound according to claim 1, wherein the taxane compound exists in the form of a solvate.

5. An antitumor pharmaceutical composition, wherein the composition contains the taxane compound according to claim 1, or a pharmaceutically acceptable salt or solvate thereof, as an active ingredient.

6. A method comprising: administering to a subject in need thereof a pharmaceutical composition comprising an effective amount of a taxane compound according to claim 1, a pharmaceutically acceptable salt or solvate thereof.

7. A preparation method for a taxane compound according to claim 1, the method comprising:

reacting an oxazolidine acid side chain precursor with a taxane mother nucleus part by an esterification reaction; and an acid hydrolysis reaction to remove the protective group on the side chain, to give the taxane compound.

8. A preparation method for a taxane compound according to claim 7, wherein, synthesis of the oxazolidine acid side chain precursor, comprises the following steps:
a) glycolic acid is protected with a benzyl group and a t-butyloxycarbonyl group to generate the corresponding Boc-protected benzyl glycolate;
b) a substituted aldehyde is condensed with $(S_R)$-t-butyl sulfinamide to form an enamine compound;
c) addition reaction of Boc-protected benzyl glycolate from step a) and the enamine compound from step b) in the presence of a lithium salt;
d) acid hydrolysis to provide a chiral amine;
e) reaction of the chiral amine with 1,1'-(dimethoxymethyl) p-methoxybenzene via an aldol condensation reaction, catalyzed by pyridinium p-toluenesulfonate to obtain an oxazolidine compound;
f) substitution of the amino group of the oxazolidine compound from step e); and
g) catalytic hydrogenation to give the oxazolidine acid side chain precursor.

9. The preparation method according to claim 8, wherein the substituted aldehyde in step b) is selected from the group consisting of C1-C6 hydrocarbyl aldehydes, C1-C6 substituted hydrocarbyl aldehydes, aromatic aldehydes, substituted aromatic aldehydes and hetero aromatic aldehydes;

the amino group of the oxazolidine compound in step f) is substituted with an acyl chloride under alkaline conditions in a solvent selected from tetrahydrofuran, dichloromethane or dioxane and at a temperature from room temperature to −70° C.; and the catalytic hydrogenation reaction in step g) is catalyzed by palladium-charcoal or palladium hydroxide with hydrogen at normal pressure or pressurized conditions in a solvent selected from the group consisting of alcohols, tetrahydrofuran and dichloromethane.

10. A preparation method for a taxane compound according to claim 7, wherein, synthesis of the taxane mother nucleus part comprises the following steps:
a) C7-hydroxyl group of 10-deacetyl baccatin III is protected with a silyl group;
b) C10-hydroxyl group of 10-deacetyl baccatin III is protected with a substituent;
c) the silyl group at the C7 position is removed; and
d) the hydroxy group at the C7 position is substituted to give the taxane mother nucleus part.

11. The preparation method according to claim 10, wherein in step a) and/or b):
(1) When $R_3$ and $R_4$ are —$OR_6$, the reaction involved is: firstly, the hydroxyl group is reacted with TsCl at room temperature to 0° C. in tetrahydrofuran or dichloromethane as the solvent and pyridine is used as the alkali, to give p-toluenesulfonate, which is further reacted with a Grignard reagent to give the corresponding ether —$OR_6$;
(2) When $R_3$ and $R_4$ are —$OCOOR_6$ or —$OCONR_{7a}R_{7b}$, the reaction involved is: under alkaline conditions, the hydroxyl group is reacted with the corresponding acyl chloride in tetrahydrofuran as the solvent at room temperature to −70° C.;

(3) When $R_3$ and $R_4$ are —OCOSR$_6$, the reaction involved is: the hydroxyl group is reacted with N,N'-carbonyldiimidazole in tetrahydrofuran as the solvent at room temperature, and the obtained product is further reacted with mercaptan via substitution reaction; or
(4) When $R_4$ is hydrogen, the reaction involved is: C7-hydroxyl group is reacted with a solution of N,N'-thiocarbonyldiimidazole in tetrahydrofuran at room temperature to give xanthate; and the obtained xanthate is subjected to Barton dioxygen free radical reaction in the mixed solution of dioxane/tetrahydrofuran at 80-100° C., catalyzed by azobisisobutyronitrile under the action of n-butyl tin hydrides;
wherein $R_6$ is —CH$_3$, —C$_2$H$_5$, —C(CH$_3$)$_3$ or phenyl; and $R_{7a}$ and $R_{7b}$ is —CH$_3$.

12. The preparation method according to claim 11, wherein
(1) When R3 and R4 are —OR6, dichloromethane is used as the solvent, the temperature is at 0° C. and the Grignard reagent includes R6MgBr;
(2) When R3 and R4 are —OCOOR6 or —OCONR7aR7b, lithium hexamethyldisilazide is used as the alkali and the temperature is at −40° C.; the acyl chloride includes R6OCOCl and R7aR7bNCOCl; or
(3) When R3 and R4 are —OCOSR6, the mercaptan includes R6SH.

13. The preparation method according to claim 9, wherein in step f), lithium hexamethyldisilazide is used as the alkali, tetrahydrofuran is used as the solvent, the temperature is at −40° C., the acyl chloride is selected from R$_6$COCl, R$_6$OCOCl and R$_{7a}$R$_{7b}$NCOCl; and
In step g) palladium hydroxide is used as the catalyst, hydrogen is introduced at 20 psi and the reaction is carried out in an alcoholic solution;
wherein $R_6$ is —CH$_3$, —C$_2$H$_5$, —C(CH$_3$)$_3$ or phenyl; and $R_{7a}$ and $R_{7b}$ is —CH$_3$.

14. The preparation method according to claim 11, wherein when $R_4$ is hydrogen, the reaction involved is: C7-hydroxyl group is reacted with a solution of N,N'-thiocarbonyldiimidazole in tetrahydrofuran at room temperature to give xanthate; and the obtained xanthate is subjected to Barton dioxygen free radical reaction in the mixed solution of dioxane/tetrahydrofuran at 85° C., catalyzed by azobisisobutyronitrile under the action of n-butyl tin hydride.

* * * * *

UNITED STATES PATENT AND TRADEMARK OFFICE
CERTIFICATE OF CORRECTION

PATENT NO. : 10,253,007 B2
APPLICATION NO. : 15/038264
DATED : April 9, 2019
INVENTOR(S) : Wei Zhou et al.

It is certified that error appears in the above-identified patent and that said Letters Patent is hereby corrected as shown below:

In the Specification

Please replace "ma" with -- may -- at Line 24, Column 19;

Please replace "THEF" with -- THF -- at Line 37, Column 44;

Please replace "100'C" with -- 100°C -- at Line 28, Column 69;

In the Claims

Please replace Claim 12 with
-- The preparation method according to claim 11, wherein
(1) When $R_3$ and $R_4$ are -$OR_6$, dichloromethane is used as the solvent, the temperature is at 0°C and the Grignard reagent includes $R_6MgBr$;
(2) When $R_3$ and $R_4$ are -$OCOOR_6$ or -$OCONR_{7a}R_{7b}$, lithium hexamethyldisilazide is used as the alkali and the temperature is at -40°C; the acyl chloride includes $R_6OCOCl$ and $R_{7a}R_{7b}NCOCl$; or
(3) When $R_3$ and $R_4$ are -$OCOSR_6$, the mercaptan includes $R_6SH$. --.

Signed and Sealed this
Thirtieth Day of July, 2019

Andrei Iancu
*Director of the United States Patent and Trademark Office*